(12) United States Patent  
Kaplan et al.

(10) Patent No.: US 8,986,380 B2  
(45) Date of Patent: Mar. 24, 2015

(54) MULTILAYERED SILK SCAFFOLDS FOR MENISCUS TISSUE ENGINEERING

(75) Inventors: David L. Kaplan, Concord, MA (US); Biman B. Mandal, Kolkata (IN)

(73) Assignee: Trustees of Tufts College, Medford, MA (US)

(*) Notice: Subject to any disclaimer, the term of this patent is extended or adjusted under 35 U.S.C. 154(b) by 0 days.

(21) Appl. No.: 13/702,606

(22) PCT Filed: Jun. 9, 2011

(86) PCT No.: PCT/US2011/039786  
§ 371 (c)(1),  
(2), (4) Date: Mar. 20, 2013

(87) PCT Pub. No.: WO2011/156586  
PCT Pub. Date: Dec. 15, 2011

(65) Prior Publication Data  
US 2013/0172999 A1    Jul. 4, 2013

Related U.S. Application Data

(60) Provisional application No. 61/352,937, filed on Jun. 9, 2010.

(51) Int. Cl.  
*A61F 2/30* (2006.01)  
*A61L 27/36* (2006.01)  
(Continued)

(52) U.S. Cl.  
CPC ......... *A61F 2/30756* (2013.01); *A61L 27/3604* (2013.01); *A61L 27/3654* (2013.01); *A61L 27/3834* (2013.01); *A61L 27/54* (2013.01); *A61L 27/56* (2013.01); *C12N 5/0068* (2013.01); *C12N 5/0655* (2013.01); *A61L 2300/252* (2013.01); *A61L 2300/30* (2013.01); *A61L 2300/414* (2013.01); *C12N 2533/90* (2013.01); *C12N 2533/50* (2013.01)  
USPC ....................................................... 623/14.12

(58) Field of Classification Search  
CPC ..... A61K 9/7007; A61K 38/17; A61K 47/42; A61K 9/0002; A61K 47/46; A61F 2/30756; A61F 2210/0004; A61F 2002/30062; A61F 2/0063; A61F 2/02; A61F 2002/30011  
See application file for complete search history.

(56) References Cited

U.S. PATENT DOCUMENTS

2006/0153815 A1    7/2006  Seyda et al.  
2006/0273279 A1*  12/2006  Kaplan et al. ...................... 252/1  
(Continued)

OTHER PUBLICATIONS

Wang et al., Biomaterials, 26:7082-7094 (2005). "In vitro cartilage tissue engineering with 3D porous aqueous-derived silk scaffolds and mesenchymal stem cells."

(Continued)

*Primary Examiner* — David Isabella  
*Assistant Examiner* — Ann Schillinger  
(74) *Attorney, Agent, or Firm* — Brenda Herschbach Jarrell; Brian E. Reese; Elizabeth M. Rohlfs

(57) ABSTRACT

Provided herein is a biocompatible implant for meniscus tissue engineering. Particularly, the biocompatible implant comprises a multi-layered crescent-shaped silk fibroin scaffold, in which each layer comprises distinct pore size and/or pore orientation, e.g., to mimic native meniscus complex architecture. Accordingly, the biocompatible implant can be used for repairing any meniscal defect or promoting meniscal regeneration in a subject.

26 Claims, 31 Drawing Sheets

(51) Int. Cl.
*A61L 27/38* (2006.01)
*A61L 27/54* (2006.01)
*A61L 27/56* (2006.01)
*C12N 5/00* (2006.01)
*C12N 5/077* (2010.01)

(56) References Cited

U.S. PATENT DOCUMENTS

| | | | |
|---|---|---|---|
| 2007/0041952 A1 | 2/2007 | Guilak et al. | |
| 2007/0212730 A1 | 9/2007 | Vepari et al. | |
| 2008/0085272 A1* | 4/2008 | Kaplan et al. | 424/130.1 |
| 2009/0171467 A1* | 7/2009 | Mann et al. | 623/23.63 |
| 2009/0234332 A1* | 9/2009 | Borenstein et al. | 604/891.1 |
| 2010/0279112 A1 | 11/2010 | Kaplan et al. | |

OTHER PUBLICATIONS

Verdonk et al., OsteoArthritis and Cartilage, 13:548-560 (2005). "Characterisation of human knee meniscus cell phenotype."
Wang et al., Biomaterials, 27:4434-4442 (2006). "Cartilage tissue engineering with silk scaffolds and human articular chondrocytes."
Wang et al., Biomaterials, 27:6064-6082 (2006). "Stem cell-based tissue engineering with silk biomaterials."
Zhang et al., Adv Drug Deliv Rev. 61(12):988-1006 (2009). "Electrospun Silk Biomaterial Scaffolds for Regenerative Medicine."
Altman et al, Biomaterials, 24:401-416(2003). "Silk-based biomaterials."
Altman et al, Biomaterials, 23:4131 (2002). "Silk matrix for tissue engineered anterior cruciate ligaments."
Angele et al., Journal of Biomedical Materials Research Part A, 85A:445-455 (2008). "Stem cell based tissue engineering for meniscus repair."
Athanasiou et al., Biomaterials, 17:93-102 (1996). "Sterilization, toxicity, biocompatibility and clinical applications of polylactic acid/ polyglycolic acid copolymers."
Baker et al., Osteoarthritis Cartilage, 17(3):336-345 (2009). "Tissue Engineering with Meniscus Cells Derived from Surgical Debris."
Baker et al., Biomaterials, 28(11):1967-1977 (2007). "The Effect of Nanofiber Alignment on the Maturation of Engineered Meniscus Constructs."
Buma et al., Biomaterials, 25:1523-1532 (2004). "Tissue engineering of the meniscus."
Cancedda et al., Matrix Biology 22:81-91 (2003). "Tissue engineering and cell therapy of cartilage and bone."
Chatain et al., Arthroscopy: The Journal of Arthroscopic and Related Surgery, 19(8):842-849 (2003). "A Comparative Study of Medial Versus Lateral Arthroscopic Partial Meniscectomy on Stable Knees: 10-Year Minimum Follow-up."
Cheung, Connective Tissue Research, 16:343-356 (1987). "Distribution of Type I, II, III and V in the Pepsin Solubilized Collagens in Bovine Menisci."
Chia et al, Journal of Orthopaedic Research, 26(7):951-956 (2008). "Compressive Moduli of the Human Medial Meniscus in the Axial and Radial Directions at Equilibrium and at a Physiological Strain Rate."
Cole et al., AAOS Instructional Course Lectures, 52:383-396 (2003). "Allograft Meniscal Transplantation: Background, Techniques, and Results."
Cook et al, J Knee Surg, 19:159-167 (2006). "Evaluation of Small Intestinal Submucosa Grafts for Meniscal Regeneration in a Clinically Relevant Posterior Meniscectomy Model in Dogs."
Cook et al,The American Journal of Sports Medicine, 34(1):32-42 (2006). "Long-term Outcome for Large Meniscal Defects Treated With Small Intestinal Submucosa in a Dog Model."
Coutts et al, Clinical Orthopaedics and Related Research, 391S:S271-S279 (2001). "Matrices for Cartilage Repair."

Englund et al., Arthritis & Rheumatism, 48(8):2178-2187 (2003). "Impact of Type of Meniscal Tear on Radiographic and Symptomatic Knee Osteoarthritis."
Eyre et al., Federation of European Biochemical Societies, 158(2):265-70 (1983). "Collagen of fibrocartilage: A distinctive molecular phenotype in bovine meniscus."
Fairbank, The Journal of Bone and Joint Surgery, 30B:664-670 (1948). "Knee Joint Changes After Meniscectomy."
Freed et al., Journal of Biomedical Materials Research, 27:11-23 (1993). "Neocartilage formation in vitro and in vivo using cells cultured on synthetic biodegradable polymers."
Freed et al., Journal of Cellular Biochemistry, 51:257-264 (1993). "Cultivation of Cell-Polymer Cartilage Implants in Bioreactors."
Ghadially et al., J. Anat.136:773-791 (1983). "Ultrastructure of normal and torn menisci of the human knee joint."
Ghosh et al., Clin Orthop Relat Res 224:52-63 (1987). "The Knee Joint Meniscus. A Fibrocartilage of Some Distinction."
Grande et al., Journal of Biomedical Materials Research, 34:211-220 (1997). "Evaluation of matrix scaffolds for tissue engineering of articular cartilage grafts."
Gunja et al., Biotechnology and Bioengineering, 103(4):808-816 (2009). "Effects of Co-Cultures of Meniscus Cells and Articular Chondrocytes on PLLA Scaffolds."
Heijkants et al., Journal of Materials Science: Materials in Medicine, 15:423-427 (2004). "Design, synthesis and properties of a degradable polyurethane scaffold for meniscus regeneration."
Herwig et al., Annals of the Rheumatic Diseases, 43:635-640 (1984). "Chemical changes of human knee joint menisci in various stages of degeneration."
Hofmann et al., Tissue Engineering, 12(10):2729-38 (2006). "Cartilage-like Tissue Engineering Using Silk Scaffolds and Mesenchymal Stem Cells."
Izuta et al., The Knee, 12:217-223 (2005). "Meniscal repair using bone marrow-derived mesenchymal stem cells: experimental study using green fluorescent protein transgenic rats."
Kang et al., J Biomed Mater Res, 77A:659-671 (2006). "Regeneration of whole meniscus using meniscal cells and polymer scaffolds in a rabbit total meniscectomy model."
Kelly et al., The American Journal of Sports Medicine, 35(1):43-52 (2007). "Hydrogel Meniscal Replacement in the Sheep Knee."
Kim et al., Biomaterials, 26:2775-2785 (2005). "Three-dimensional aqueous-derived biomaterial scaffolds from silk fibroin."
Kobayashi et al., Biomaterials, 26:3243-3248 (2005). "A two year in vivo study of polyvinyl alcohol-hydrogel (PVA-H) artificial meniscus."
Kohn et al., Scandinavian Journal of Medicine & Science in Sports, 9:141-145 (1999). "Meniscal substitutes- animal experience."
Ma et al., J Biomed Mater Res 64A:273-81 (2003). "Chondrogenesis of human mesenchymal stem cells encapsulated in alginate beads."
Mandal et al., Biomaterials, 32(2):639-651 (2011). "Multilayered silk scaffolds for meniscus tissue engineering."
Mandal et al., Tissue Engineering: Part A, 17(21-22):2749-61 (2011). "Stem Cell-Based Meniscus Tissue Engineering."
Marijnissen et al., Biomaterials, 23:1511-1517 (2002). "Alginate as a chondrocyte-delivery substance in combination with a non-woven scaffold for cartilage tissue engineering."
Mauck et al., The Anatomical Record, 290:48-58 (2007). "Regional Multilineage Differentiation Potential of Meniscal Fibrochondrocytes: Implications for Meniscus Repair."
McDevitt et al., Clin Orthop, 252:8-18 (1990). "The Ultrastructure and Biochemistry of Meniscal Cartilage."
Meinel et al., Biotechnol Bioeng, 88:379-91 (2004). "Engineering Cartilage-Like Tissue Using Human Mesenchymal Stem Cells and Silk Protein Scaffolds."
Meinel et al., J Biomed Mater Res 71A:25-34 (2004). "Engineering bone-like tissue in vitro using human bone marrow stem cells and silk scaffolds."
O'Connor, Am. J. Anat., 147:407-418 (1976). "The Histological Structure of Dog Knee Menisci with Comments on Its Possible Significance."

(56) References Cited

OTHER PUBLICATIONS

Peretti et al., The American Journal of Sports Medicine, 32(1):146-158 (2004). "Cell-Based Therapy for Meniscal Repair. A Large Animal Study."

Petersen et al., Anat Embryol, 197:317-324 (1998). "Collagenous fibril texture of the human knee join menisci."

Port et al., The American Journal of Sports Medicine, 24(4):547-555 (1996). "Meniscal Repair Supplemented With Exogenous Fibrin Clot and Autogenous Cultured Marrow Cells in the Goat Model."

Proctor et al., Journal of Orthopaedic Research, 7:771-782 (1989). "Material Properties of the Normal Medial Bovine Meniscus."

Setton et al., Clinical Orthopaedics and Related Research, 367S:S254-S272 (1999). "Biomechanical Factors in Tissue Engineered Meniscal Repair."

Temenoff et al., Biomaterials 21:431-440 (2000). "Review: tissue engineering for regeneration of articular cartilage."

Tissakht et al., J. Biomechanics, 28(4):411-422 (1995). "Tensile Stress-Strain Characteristics of the Human Meniscal Material."

Van Tienen et al, Biomaterials, 23:1731-1738 (2002). "Tissue ingrowth and degradation of two biodegradable porous polymers with different porosities and pore sizes."

* cited by examiner

MULTILAYERED SILK SCAFFOLDS FOR MENISCUS TISSUE ENGINEERING

CROSS-REFERENCE TO RELATED APPLICATIONS

This application is a 35 U.S.C. §371 National Phase Entry Application of International Application No. PCT/US2011/039786 filed Jun. 9, 2011, which designates the U.S., and which claims benefit under 35 U.S.C. §119(e) of the U.S. Provisional Application No. 61/352,937 filed Jun. 9, 2010, the contents of which are incorporated herein by reference in their entireties.

GOVERNMENT SUPPORT

This invention was made with federal funding under Grant No. P41 EB002520, awarded by the National Institutes of Health. The U.S. government has certain rights in the invention.

FIELD OF INVENTION

The present invention generally relates to scaffolds for meniscus tissue engineering.

BACKGROUND OF THE INVENTION

There is a constant rise in demand for artificial meniscal grafts mimicking native articular tissue to be used for surgical treatment of meniscal lesions. In Europe alone over 400,000 surgical cases involving the meniscus are being performed annually, and over 1 million similar cases are treated in the United States. By far meniscectomy is known to be the most common surgical procedure performed in the orthopedic field today. The current therapeutic strategy for this type of meniscus tears is either partial or subtotal meniscectomy, with only a small percentage being successfully repaired but finally leading to osteoarthritis of the knee with time (Fairbank, 1948; Englund et al., 2003).

A functional intact meniscus is of paramount importance for homeostasis of the knee joint. It helps perform complex knee joint biomechanics, in load bearing, load transmission, shock absorption, joint stability and joint lubrication. However, due to lack of vasculature, human meniscus has a poor healing potential. Blood vessels are reported to be present only in the outer 10-30% of the meniscal body and can be sutured successfully with a high success rate (Englund et al., 2003; Buma et al., 2004). In contrast, majority of these meniscal tears are situated in the inner avascular zone lacking spontaneous healing process and hence be resected (Kohn et al., 1999). Removal and/or damage of all this important anatomical structure eventually leads to degenerative changes of the articular cartilage, osteoarthritis and subsequent clinical symptoms due to increased peak stresses (Fairbank, 1948; Cole et al., 2003; Chatain et al., 2003; Englund et al., 2003). It has been estimated that cartilage volume loss after meniscectomy is at 4% per year and is known to be more pronounced in the lateral compartment as compared to medial compartment (Verdonk and Kohn, 1999).

To this problem, meniscus allo/autograft transplantation represents a potential tissue engineering solution for the symptomatic, meniscus deficient patient to substitute for lost meniscal tissue to prevent cartilage degeneration, relieve pain and to improve function. The strategies included delivery of potent cells to the defect site for repair including chondrocytes, fibrochondrocytes and stem cells (Peretti et al., 2004; Izuta et al., 2005; Port et al., 1996). The other strategy being direct replacement of defective tissue in part or as a whole has also been carried out using both natural and synthetic scaffolds, including collagen-based grafts, subintestinal submucusa, cell free hydrogels, degradable porous foams, macro- and microporous polymeric meshes to improve immediate or long term outcomes (Buma et al., 2004; Stone et al., 1992; Cook et al., 2006 a; Setton et al., 1999; Sweigart et al., 2001; Kobayashi et al., 2005; Kelly et al., 2007; Van Tienen et al., 2002; Heijkants et al., 2004; Cook et al., 2006 (a, b). In the past, a variety of these materials have already been reported for cartilage tissue engineering including, poly-glycolic acid (PGA), poly-L-lactic acid (PLA), copolymer poly-lactic-co-glycolic acid (PLGA) and alginate (Grande et al., 1997; Freed et al., 1993 a,b; Paige et al., 1996; Marijnissen et al., 2002; Ma et al., 2003). However, these materials have intrinsic limitations, including inflammation in vivo in the case of the polyesters and rapid degradation and high swelling in the case of collagen, which can limit their use (Cancedda et al., 2003; Athanasiou et al., 1996; Wakitani et al., 1994; Meinel et al., 2004 a,b). In terms of meniscus shape, a PGA spun matrix was used in a rabbit model but failed to recapitulate the complex internal meniscus architecture (Kang et al., 2006). Additional efforts have focused on mimicking the native mesh-like meniscus architecture using cell alignment on biodegradable electrospun fibers for enhanced biomechanics (Baker and Mauck; 2007; Baker et al., 2009). Many of the above studies employed in vivo animal models to show chondroprotection by the implant, but with a low success rate due to failure to mimic the complex internal architecture and biomechanics of the native meniscus.

In order to develop a functional tissue engineered meniscus, mimicking its complex internal architecture is most important. In this regard, none of the approaches previously reported have successfully recapitulated the complex native meniscal multiporous and aligned structure as a single meniscus wedge shaped unit to completely and/or partially eliminate cartilage degeneration. Thus, in order to mimic the meniscus in a tissue engineered approach, understanding its structural and functional components is important. Menisci are wedge-shaped semi-lunar discs present in duplicate in each knee joint which are attached to the transverse ligaments, the joint capsule, the medial collateral ligament (medially) and the menisco-femoral ligament (laterally) (McDevitt and Webber, 1990; Sweigart and Athanasiou, 2001). An extensive scanning electron micrograph study of the human meniscus by Peterson and Tillmann showed 3 distinct zones comprising of outer finer meshwork, middle broader mesh like fibrous structure and bottom most aligned collagen bundles in laminar orientation (Petersen and Tillmann, 1998). This particular aligned laminar orientation of fibers along with mesh structure within was reported to contribute maximally for its high intrinsic tensile and compressive properties of native meniscus (Sweigart and Athanasiou, 2001; Tissakht and Ahmed, 1995; Petersen and Tillmann, 1998). As a fibrocartilaginous structure, the meniscus has characteristic of both fibrous (outer region) and cartilaginous (inner region) properties (O'Connor, 1976; Petersen and Tillmann, 1998). Knee meniscal fibrocartilaginous tissue contains mainly water (72%), collagens (22%) and glycosaminoglycans (0.8%) (Proctor et al, 1989; Herwig et al, 1984). Of the total collagen content, Type I collagen accounts for over 90%. The remaining 10% are meniscal collagens Type II, III and V collagen (Eyre and Wu, 1983; McDevitt and Webber, 1990). It has been shown that peripheral two-thirds of the meniscus solely consist of type I collagen, whereas type II collagen comprises a large portion of the fibrillar collagen on the inner side (Cheung, 1987). Proteoglycans make for 2-3% of the dry weight and are mainly concentrated in the inner cartilaginous region of the meniscus (McDevitt and Webber, 1990; Buma et al., 2004). Also, the cellular component of the meniscus further reflects its fibrocartilaginous nature, the main cell type being meniscus fibrochondrocytes (McDevitt and Webber, 1990). Regarding cell types, at least two cell populations are present within the human meniscus (Ghadially et al., 1983). The fibrochondrocytes being the main cell type are reported within the inner and middle part of the meniscus having a rounded or oval shaped cell structure surrounded by an abundant ECM deposition (McDevitt and Webber, 1990; Ghadially et al., 1983). The outer one-third meniscus is reported to be populated mainly by spindle shaped fibroblast like cells with a dense connective tissue (Ghadially et al., 1983).

Over the years, newer improvised methods such as meniscus allograft or autograft transplantation have been constantly searched for substituting the resected meniscus in case of either total or partial meniscectomy. However, none to date have generally been able to recapitulate and recreate the native meniscal multiporous and aligned structure as a single meniscus wedge shaped unit to completely and/or partially eliminate cartilage regeneration. As such, there is still a strong need to develop a scaffold that can mimic heterogeneous architecture and functions of native meniscal tissue.

SUMMARY OF THE INVENTION

Removal of injured/damaged meniscus, a vital fibrocartilaginous load-bearing tissue, impairs normal knee function and predisposes patients to osteoarthritis. Meniscus tissue engineering solution is one option to improve outcomes and relieve pain. The inventors have engineered a three-layered wedge-shaped silk meniscal scaffold system to mimic native meniscus architecture. Such multiporous silk construct can be used as a micro-patterned template for directed tissue growth with respect to form and function of meniscus-like tissue. Thus, the inventors' findings provide multilayered silk fibroin-based meniscal implants for treatment of meniscal repair and/or regeneration, and methods of making such implant.

Accordingly, provided herein is a biocompatible implant comprising a multi-layered silk fibroin scaffold that mimics native meniscus architecture and methods of making the same. The silk fibroin scaffold comprises at least a first layer and a second layer, wherein each of the first layer and the second layer has a distinct pore size distribution and pore orientation. The silk fibroin scaffold can be adapted for meniscus repair and/or regeneration, e.g., each layer of the silk fibroin scaffold can be crescent-shaped or C-shaped.

In some embodiments, the silk fibroin scaffold can further comprise at least one mammalian cell (e.g., human cells). Non-limiting examples of mammalian cells that can be used in the scaffold include fibroblasts, chondrocytes, stem cells, bone marrow cells, embryonic stem cells, mesenchymal stem cells, induced pluripotent stem cells, differentiated stem cells, tissue-derived cells, and any combinations thereof.

Different types of mammalian cells can be distributed within the silk fibroin scaffold in a spatial manner in order to mimic the native tissue. In some embodiments, the outer region or the periphery of the silk fibroin scaffold can comprise one or more fibroblasts. In other embodiments, the inner region of the silk fibroin scaffold can comprise one or more chondrocytes. In some embodiments, the silk fibroin scaffold can comprise one or more stem cells, which are differentiated over time to chondrogenic phenotypes.

In some embodiments, the first layer of the silk fibroin scaffold comprises circular or approximately circular pores. The circular or approximately pores can be interconnected. In some embodiments, the pore size distribution of the first layer can range from about 100 microns to about 1000 microns, from about 200 microns to about 700 microns, or from about 300 microns to about 600 microns.

In some embodiments, the first layer of the silk fibroin scaffold comprises circular or approximately circular pores distributed in a gradient of pore size. For example, in one embodiment, the circular or approximately circular pores can be distributed within the first layer such that two or more distinct sub-layers, each of which has a distinct pore size distribution, are formed. In such embodiment, the sub-layer closer to the second layer as described herein can have a larger pore size distribution than other sub-layers, e.g., having a pore size distribution ranging from about 400 microns to about 700 microns, or from about 500 microns to about 600 microns.

In some embodiments, when the first layer of the silk fibroin scaffold comprises one pore size distribution, the silk fibroin scaffold can further comprise a third layer. In such embodiments, the third layer can comprise circular or approximately circular pores with a pore size distribution ranging from about 400 microns to about 700 microns, or from about 500 microns to about 600 microns. In another embodiment, the third layer can comprise circular or approximately circular pores with a pore size distribution ranging from about 300 microns to about 600 microns, or from about 350 microns to about 500 microns.

In some embodiments, the second layer of the silk fibroin scaffold described herein can comprise laminar channels. In such embodiments, the laminar channels can be aligned. In some embodiments, the laminar channels can have a pore width distribution ranging between about 30 microns and about 100 microns or between about 60 microns and about 80 microns.

In various embodiments, the porosity of each individual layer, e.g., the first layer, the second layer, or the third layer, can be independently at least about 30%.

In some embodiments, each layer, e.g., the first layer, the second layer, or the third layer can be individually formed. Each individual layer can remain separate as long as possible, e.g., until they are ready for implantation, or they can be stacked together into a single unit. Each individual layer can be stacked together to form a single silk fibroin scaffold, for example, by stitching (e.g., with at least one silk fibroin fiber), by riveting (e.g., with at least one silk fibroin plug), or by a biocompatible and/or biodegradable glue (e.g., fibrin, silk fibroin, collagen or any combinations thereof.)

In some embodiments, the biocompatible implant and/or the silk fibroin scaffold can further comprise at least one extracellular matrix, e.g., exogenously added, or produced by any mammalian cells present in the silk fibroin scaffold.

In some embodiment, the biocompatible implant and/or the silk fibroin scaffold can further comprise at least one active agent. Examples of the active agents include, but are not limited to, TGF-β1, TGF-β2, TGF-β3, BMP-2, BMP-4, BMP-6, BMP-12, BMP-13, fibroblast growth factor-1, fibroblast growth factor-2, platelet-derived growth factor-AA, platelet-derived growth factor-BB, platelet rich plasma, IGF-I, IGF-II, GDF-5, GDF-6, GDF-8, GDF-10, vascular endothelial cell-derived growth factor, pleiotrophin, endothelin, nicotinamide, glucagon like peptide-I, glucagon like peptide-II, parathyroid hormone, tenascin-C, tropoelastin, thrombin-derived peptides, laminin, biological peptides containing cell-binding domains and biological peptides containing heparin-binding domains, therapeutic agents, and any combinations thereof.

Another aspect provided herein is a method of producing the biocompatible implant described herein. The method comprises forming a silk fibroin scaffold having at least a first layer and a second layer, wherein each of the first layer and the second layer has a distinct pore size distribution and orientation.

When the biocompatible implant is for use in meniscus repair and/or regeneration, each layer of the silk fibroin scaffold can be fabricated in a shape of a meniscus, e.g., crescent-shaped or C-shaped. In one embodiment, the silk fibroin scaffold is wedge-shaped.

In particular embodiments, the method comprises forming circular or approximately circular pores within the first layer of the silk fibroin scaffold, e.g., by salt-leaching method. In some embodiments, the method comprises forming circular or approximately circular pores in a gradient of pore size within the first layer, e.g., forming two or more distinct sub-layers within the first layer, each of which has a distinct pore size distribution as described herein.

In some embodiments, the method comprises forming laminar channels within the second layer of the silk fibroin scaffold, e.g., with a freeze-drying method.

In some embodiments, the method can further comprise forming at least a third layer, for example, containing circular or approximately circular pores with a defined pore size distribution as described herein, e.g., using a salt-leaching method.

In some embodiments, the silk fibroin scaffold or any individual layer can be subjected to at least one post-treatment, e.g., to enhance the mechanical property. Exemplary post-treatment include, without limitations, heat treatment, stretching, methanol or ethanol immersion, and any combinations thereof.

In some embodiments, the method can further comprise forming an immobilized active-agent gradient within the silk fibroin scaffold or each individual layer, e.g., to facilitate spatial arrangement of cells within the silk fibroin scaffold. For example, one or more mammalian cells (e.g., human cells) as described herein can be placed within any porous layer. In some embodiments, one or more fibroblasts can be placed around the periphery or the outer region of the silk fibroin scaffold or each individual layer. In some embodiments, one or more chondrocytes can be placed in the non-periphery region or the inner region of the silk fibroin scaffold or each individual layer. In some embodiments, stem cells can be placed anywhere throughout the silk fibroin scaffold or individual layers. The stem cells can then be differentiated into a chondrogenic phenotype.

In some embodiments of the silk fibroin scaffold or the individual layers containing mammalian cells, the method can further comprise culturing the silk fibroin scaffold in vitro for a period of time, e.g., for at least about 6 hours. In some embodiments, in vitro culture can be independently performed on any of the individual layers For separate individual layers, the method can further comprise stacking the individual layers together into a single unit of a silk fibroin scaffold, e.g., by stitching the individual layers (e.g., with at least one silk fibroin fiber), by riveting (e.g., with at least one silk fibroin plug), or with a biocompatible and/or biodegradable glue such as fibrin, silk fibroin, collagen or any combinations thereof.

In some embodiments, the method can further comprise adding into the silk fibroin scaffold or the biocompatible implant at least one active agent described herein.

Any biocompatible implant described herein can be implanted into a subject in need thereof for a meniscus repair or regeneration. Accordingly, methods of repairing a meniscal defect or promoting mensical regeneration in a subject are also provided herein. In one embodiment, the method comprises implanting a biocompatible implant described herein into a defect site in need of meniscus repair or regeneration.

When the individual layers of the silk fibroin scaffold are separate and are not assembled together as a single unit, they can be stacked together using any of the methods described herein before implanting it into the subject. In some embodiments, the treatment method can further comprise securing the biocompatible implant in the defect site. In some embodiments, the treatment method can further comprise removing at least a portion of a defective meniscus from the subject.

In some embodiments, the treatment method can further comprise placing one or more mammalian cells (e.g., chondrocytes, fibroblasts, and/or stem cells) in the defect site, e.g., after implanting the biocompatible implant into the subject, or by placing the cells into the silk fibroin scaffold before implantation.

In various embodiments, the treatment method can further comprise administering to the subject or to the defect site at least one active agent described herein.

BRIEF DESCRIPTION OF THE DRAWINGS

FIGS. 3A to 3C show initial cell attachment on day 1, and FIGS. 3D to 3E show confluent cell covering scaffold pores on day 28. FIGS. 3G to 3I show close-up images showing cell alignment and spreading within pores and laminas. Top 102A scaffold layer is represented by FIGS. 3A, 3D, and 3G; middle 102B layer (FIGS. 3B, 3E, 3H) and bottom 104 layer (FIGS. 3C, 3F, and 3I). Scale bar represents 300 microns.

FIGS. 4A to 4C show initial cell attachment on day 1, and FIGS. 4D to 4E show confluent cell covering scaffold pores on day 28. FIGS. 4G to 4I show close-up images showing cell alignment and spreading within pores and laminas. Top 102A scaffold layer is represented by FIGS. 4A, 4D, and 4G; Middle 102B layer (FIGS. 4B, 4E, 4H) and Bottom 104 layer (FIGS. 4C, 4F, and 4I). Scale bar represents 300 microns.

FIG. 9A shows the DNA content; FIG. 9B shows the total collagen; FIG. 9C shows the amount of collagen in µg per ng of DNA and FIG. 9D shows the amount of collagen in µg per mg of scaffold estimated in 3 scaffolds layers individually seeded with primary human chondrocytes and fibroblasts in chondrogenic medium after day 1 and 28. Data represents Mean±standard deviation (n=4, **p<0.01).

FIG. 10A shows the total GAG content; FIG. 10B shows the amount of GAG in µg per ng of DNA; FIG. 10C shows the amount of GAG in µg per mg of scaffold and FIG. 10D shows the total GAG in medium, estimated in 3 scaffold layers individually seeded with primary human chondrocytes and fibroblasts in chondrogenic medium after day 1 and 28. Data represents Mean±standard deviation (n=4, *p<0.05, **p<0.01).

FIG. 11A shows a representative image of fabricated meniscus shaped scaffold in three stacked layers. FIGS. 11B to 11D show SEM images showing porosity and interconnectivity within individual fabricated silk layers without cells: top layer 102A with 350-400 micron pores (FIG. 11B); middle layer 102B with 500-600 micron pores (FIG. 11C); bottom layer 104 with 60-80 micron pores (FIG. 11D). Scale bar represents 300 microns.

FIG. 15A shows the total collagen; FIG. 15B shows the amount of collagen in µg per ng of DNA; FIG. 15C shows the amount of collagen in µg per mg of scaffold and the total DNA content, estimated in 3 scaffolds layers individually seeded with hMSCs in chondrogenic medium after day 1, 14 and 28. Data represents Mean±standard deviation (n=4, **p<0.01).

FIG. 16A shows the total GAG content; FIG. 16B shows the total GAG in medium; FIG. 16C shows the amount of GAG in µg per mg of scaffold and FIG. 16D shows the amount of GAG in µg per ng of DNA, estimated in 3 scaffold layers individually seeded with hMSCs in chondrogenic medium after day 1, 14 and 28. Data represents Mean±standard deviation (n=4, **p<0.01).

FIG. 17A shows the fold increase of collagen 1-a1; FIG. 17B shows the fold increase of aggrecan; FIG. 17C shows the fold increase of Sox9 and FIG. 17D shows the fold increase of collagen X genes of differentiating hMSCs within individual scaffold layers in chondrogenic medium after day 14 and 28. Data represents Mean±standard deviation (n=4, **p<0.01).

DETAILED DESCRIPTION OF THE INVENTION

Removal of injured/damaged meniscus, a vital fibrocartilaginous load-bearing tissue, impairs normal knee function and predisposes patients to osteoarthritis. Meniscus tissue engineering solution is one option to improve outcomes and relieves pain. Accordingly, described herein are biocompatible implants comprising a multi-layered silk fibroin scaffold that mimics heterogeneous, native meniscus tissue structures for meniscus tissue engineering. and methods of making the same. Methods for repairing a meniscal defect and/or promoting meniscal regeneration in a subject in need thereof are also provided herein.

Silks have been employed for applications in biomedical and biotechnological fields. See Hofmann et al., 111 J Control Release 219 (2006); Lawrence et al., 30 Biomaterials 1299 (2009); Soffer et al., 19 Biomater Sci Polym Ed 653 (2008); and Sofia et al., 54 J. Biomed. Mater. Res. 139 48 (2001). Silk is popular because of its availability, the ease of purification (Sofia et al., 54 J. Biomed. Mater. Res. 139 48 (2001); Sohn et al., 5 Biomacromol. 751-57 (2004); and Um et al., 29 Int. J. Biol. Macromol. 91-97 (2001)), and its attractive properties. See Kaplan et al., in ACS SYMPOSIUM SERIES, Vol. 544, 2-16 (McGrath & Kaplan, eds., Birkhauser, Boston, Mass., 1994); Kaplan et al., PROTEIN BASED MATS. 103-31 (McGrath & Kaplan, eds., Birkhauser, Boston, Mass., 1998); and Wang et al., 27 Biomats. 6064-82 (2006).

Silk has an unusual amino acid sequence: the bulk of the silk fibroin protein is organized into hydrophobic domains that are rich of alanine and glycine residues, and amino acids with large side chains that are clustered in chain-end hydrophilic blocks. See Bini et al., 335 J. Mol. Biol. 27-40 (2004). Structurally, the hydrophobic blocks assemble into crystalline regions while the hydrophilic blocks form less ordered regions. Zhou et al., 44 Proteins: Struct. Funct. Bioinf. 119 22 (2001). The large hydrophobic regions of silk fibroin are capable of assembling into crystalline β sheet structures via intra- and inter-molecular hydrogen bonding and hydrophobic interactions, thus conferring unique features to the silk fibroin protein.

Biocompatible Implants Comprising a Multi-Layered Silk Fibroin Scaffold

The unique properties of silk fibroin (mechanical strength, biodegradability, biocompatibility, sequence variants and/or crystallization domains to influence properties) provide unique and versatile features for tissue engineering. In one aspect, provided herein is a biocompatible implant comprising a silk fibroin scaffold having at least a first layer and a second layer, wherein each of the first layer and the second layer has a distinct pore size distribution and pore orientation or pore structure.

Figure 1:
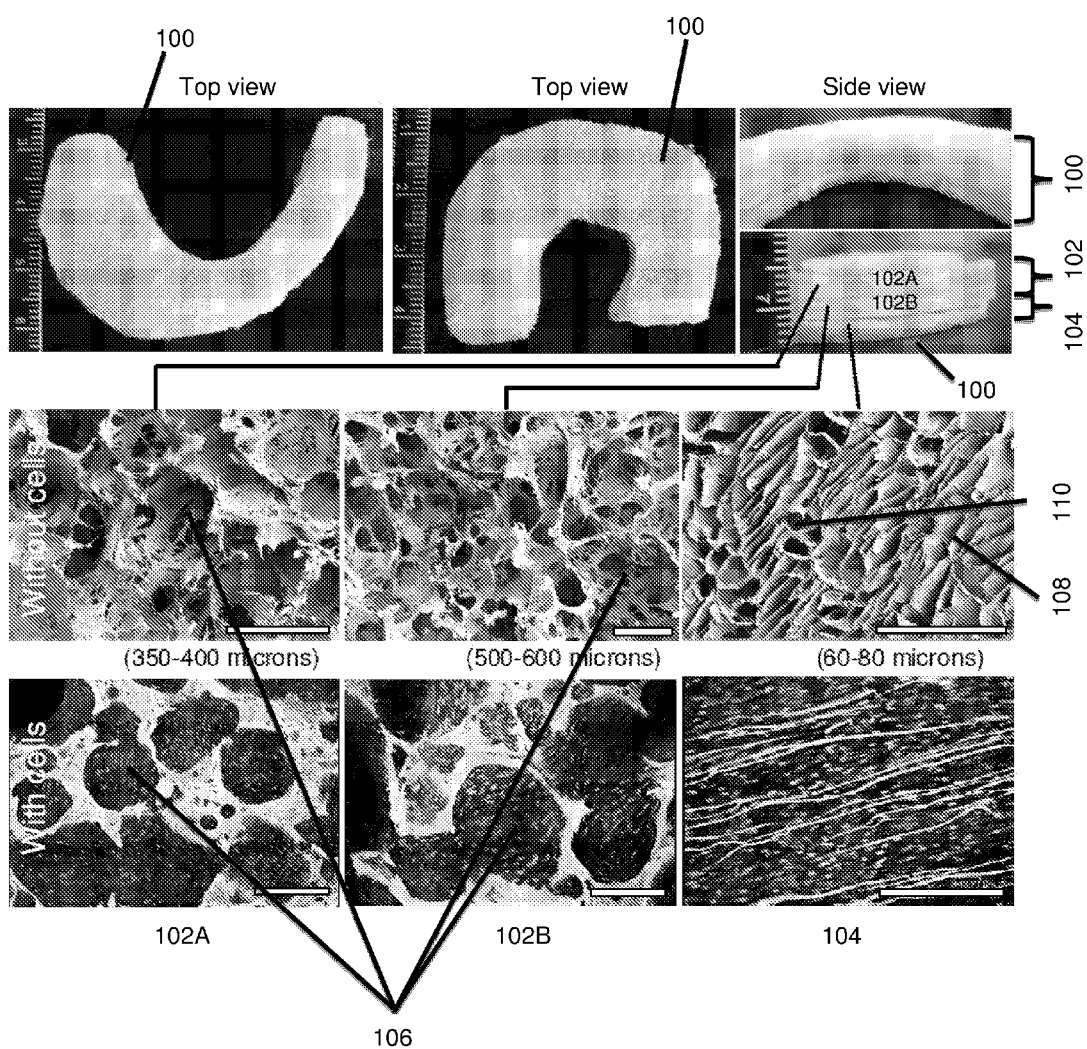
FIG. 1 show representative images of regenerated silk scaffolds according to one embodiment of the invention for functional meniscus engineering. Representative images of fabricated meniscus shaped scaffolds with three stacked layers (Top). SEM images showing porosity and interconnections within pores of individual silk layers without cells (middle) and confocal images of layers with confluent cells (bottom). Scale bar represents 300 microns.

By way of example only, FIG. 1 shows a silk fibroin scaffold 100 according to one or more embodiments of the invention. The silk fibroin scaffold 100 comprises a first layer 102 and a second layer 104, wherein the first layer 102 and the second layer 104 each have a distinct pore size and pore orientation.

In some embodiments, the first layer 104 of the silk fibroin scaffold can comprise circular (round) or approximately circular pores 106. However, the pores 106 can also have other cross-sectional shapes. In some embodiments, the pores 106 can have a size distribution ranging from about 100 microns to about 1000 microns, from about 200 microns to about 700 microns, or from about 300 microns to about 600 microns, or a portion of any thereof. In one embodiment, the pores of the first layer 102 have a pore size distribution of about 350 microns to about 600 microns, or a portion thereof. As used herein, the term "pore size" refers to a diameter or an effective diameter of the cross-sections of the pores. The term "pore size" can also refer to an average diameter or an average effective diameter of the cross-sections of the pores, based on the measurements of a plurality of pores. The effective diameter of a cross-section that is not circular equals the diameter of a circular cross-section that has the same cross-sectional area as that of the non-circular cross-section. In some embodiments, the silk fibroin can be swellable when the silk fibroin scaffold is hydrated. The sizes of the pores can then change depending on the water content in the silk fibroin. The pores 106 can be filled with a fluid such as water or air.

The pores 106 can be randomly distributed within the first layer 102. Some of the pores 106 can be closed pores, meaning that they are not connected or joined with other pores or open to the surfaces of the silk fibroin scaffold. In some embodiments, at least the pores 106 can be interconnected. As used herein, the term "interconnected" is used in reference to open pores which are connected to one another and communicate with one another within a scaffold, such that, e.g., a cell present in a pore can migrate from one pore to the other within the scaffold. The phrase "at least partially interconnected" as used herein refers to at least about 10%, at least about 20%, at least about 30%, at least about 40%, at least about 50%, at least about 60%, at least about 70%, at least about 80%, at least about 90%, at least about 95%, at least about 98%, at least about 99% or more, of all the pores can be connected to one another to form one or more continuous networks and communicate with each other to within a scaffold. Stated other way, in some embodiments, the phrase "at least partially interconnected" as used herein can refer to at least about 1%, at least about 2%, at least about 5%, at least about 10%, at least about 20%, at least about 30%, at least about 40%, at least about 50%, at least about 60%, at least about 70%, at least about 80%, at least about 90%, of all the pores can be closed and not communicate with the adjacent pores. Methods of measuring the pore size and/or pore interconnectivity are well known in the art, e.g., liquid expulsion (or liquid displacement) porometry method, mercury porosimetry method and gas adsorption. Scanning electron microscopy or light scattering microscopy can also be used to determine pore size and/or pore interconnectivity as described in the Examples.

In some embodiments, the circular or approximately circular pores 106 can be distributed within the first layer 102 as a gradient of pore size. A "gradient of pore size" can refer to a progressive change in the pores size, either gradually, in stages or in steps, across the thickness of a scaffold. In some embodiments, the pore size can increase gradually from about 100 microns to about 1000 microns, from about 200 microns to about 700 microns, or from about 300 microns to about 600 microns, across the thickness of the first layer. In some embodiments, the pore size can decrease gradually from about 1000 microns to about 100 microns, from about 700 microns to about 200 microns, or from about 600 microns to about 300 microns, across the thickness. In some embodiments, the pore size can increase in stages, e.g., at least two stages, at least three stages, at least four stages, or more, within the first layer, wherein each stage or each sub-layer has a distinct pore size distribution. For example, as shown in FIG. 1, the circular or approximately circular pores 106 can be distributed within the first layer 102 to form two or more (e.g., 2, 3, 4, 5 or more) distinct sub-layers 102A and 102B, each of which has a distinct pore size distribution. In such embodiments, the sub-layer 102B closer to the second layer 104 can have a larger pore size distribution than the other sub-layers 102A. For example, the larger pore size distribution within the sub-layer 102B can range from about 600 microns to about 700 microns, or about 550 microns to about 650 microns, or from about 500 microns to about 600 microns. In one embodiment, the sub-layer 102B can have a pore size distribution of about 500 microns to about 600 microns, while the sub-layer 102A can have a smaller pore size distribution, e.g., from about 300 microns to about 500 microns, or about 350 microns to about 400 microns. The sub-layers 102A and 102B can be integral to the first layer 102 and form a monolith or they can be separate entities. As shown in FIG. 1, the sub-layers 102A and 102B are separate entities.

In some embodiments, the silk fibroin scaffold can further comprise a third layer. The third layer can comprise circular or approximately circular pores with a pore size distribution ranging from about 100 microns to about 1000 microns, from about 200 microns to about 700 microns, from 300 microns to about 600 microns, or a portion of any thereof. In such embodiments, the third layer can be located between the first layer and the second layer or it can be located on top of the first layer. In one embodiment where the first layer has only one pore size distribution, the third layer can be also referred as a sub-layer 102A or 102B, as shown in FIG. 1. In such embodiment, depending on the pore size distribution of the first layer, e.g., a pore size distribution of about 500 microns to 600 microns, the third layer can be referred as a sub-layer 102A with a pore size distribution of about from about 300 microns to about 500 microns, or about 350 microns to about 400 micron. If the pore size distribution of the first layer is about 350 microns to about 400 microns, the third layer can be referred as a sub-layer 102B with a pore distribution of about 400 microns to about 600 microns or about 500 microns to about 600 microns.

In accordance of the invention, the silk fibroin scaffold comprises a second layer. In some embodiments, the second layer can comprise laminar channels. The term "laminar channels" as used herein refer to channels or microchannels arranged in laminae, e.g., channels or microchannels arranged in layer-by-layer. Exemplary laminar channels 108 are shown in FIG. 1. In some embodiments, the laminar channels can be at least partially aligned. The term "aligned" as used herein refers to laminar channels arranged with their channel lumens 110 facing the same direction or laminar channels arranged in parallel to each other. The phrase "at least partially aligned" as used herein refers to at least some laminar channels having their channel lumens 110 facing the same direction or arranged in parallel to each other, e.g., at least about 10%, at least about 20%, at least about 30%, at least about 40%, at least about 50%, at least about 60%, at least about 70%, at least about 80%, at least about 90%, at least about 95%, at least about 98%, at least about 99% or more, of the laminar channels can have their channel lumens facing the same direction or arranged in parallel to each other.

The lumen of the laminar channels can be of any shape, e.g., square, round, or rectangular. The cross-sections of the laminar channel can vary in size along the channel length. In some embodiments, the laminar channels can have a pore width distribution ranging between about 30 microns and about 100 microns, between about 60 microns and about 80 microns, or a portion of any thereof. In one embodiment, the pore width distribution is between about 60 microns and about 80 microns. As used herein, the term "pore width" can refer to, in one embodiment, an average of a characteristic length (e.g., any side, a diagonal, or an average of two sides) of any cross-sectional lumen of the channels, based on the measurement of a plurality of the channels. In another embodiment, the term "pore width" as used herein can refer to a characteristic length of any cross-sectional lumen of a channel. In some embodiments, when the cross-section of the channel lumen is circular, the pore width can be a pore diameter.

As described herein, the first layer and the second layer of the silk fibroin scaffold each comprises distinct pore size distribution and pore orientation, e.g., to mimic native meniscus complex architecture. As used herein, "pore orientation" can be characterized by pore structure and/or pore shape. By way of example only, the first layer can comprise at least partially interconnected pore structures, while the second layer can comprise laminar pore structures. In some embodiments, interconnected pore structures can be randomly distributed. In some embodiments, the laminar pore structures can be aligned. In terms of the pore shape, the first layer can comprise circular or approximately circular pores, while the second layer can comprise channel-like pores as described herein.

In some embodiments, each layer of the silk fibroin scaffold can independently have a porosity of at least about 30%, at least about 40%, at least about 50%, at least about 60%, at least about 70%, at least about 80%, at least about 90%, or higher. Too high porosity can yield a silk fibroin scaffold with lower mechanical properties. However, too low porosity can decrease the number of cells allowed inside the pores of the scaffold and/or cell motility, and/or decrease the nutrient/active agent transport within a scaffold. One of skill in the art can adjust the porosity accordingly, based on a number of factors such as, but not limited to, pre-determined mechanical properties of the scaffold, cell seeding number, and/or transport kinetics of nutrients or any active agents. The term "porosity" as used herein is a measure of void spaces in a material, e.g., a matrix such as silk fibroin, and is a fraction of volume of voids over the total volume, as a percentage between 0 and 100% (or between 0 and 1). Determination of a matrix or scaffold porosity is well known to a skilled artisan, e.g., using standardized techniques, such as mercury porosimetry and gas adsorption, e.g., nitrogen adsorption.

In some embodiments, any individual layer described herein (e.g., the first layer, including sub-layers, the second layer and/or the third layer) can be individually informed and remain separate until it is ready for use, e.g., for implantation. In such embodiments, any individual layer can be stored dried or hydrated, e.g., in their original packaging. In one embodiment, any individual layer that comprises mammalian cells can be maintained and/or cultured in cell culture media for any period of time, e.g., at least about 6 hours.

Figure 2:
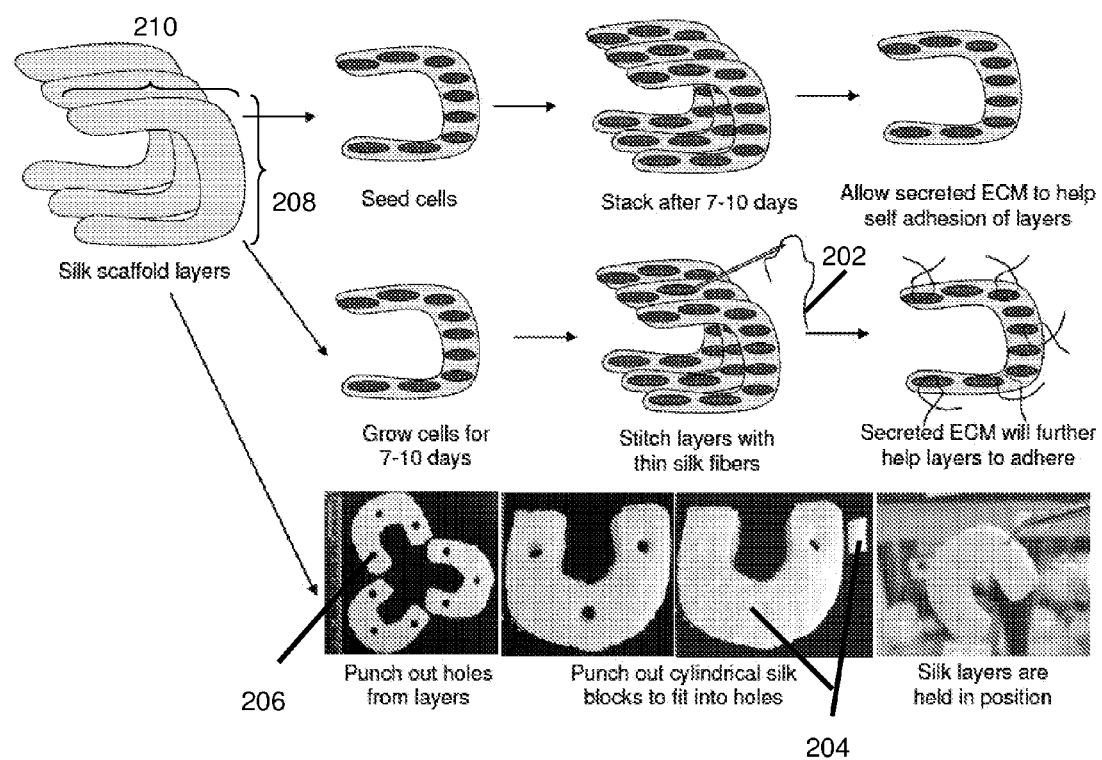
FIG. 2 show exemplary strategies for aligning and integrating individual silk scaffold layers to reconstruct functional meniscus for graft applications.
Figure 3A:
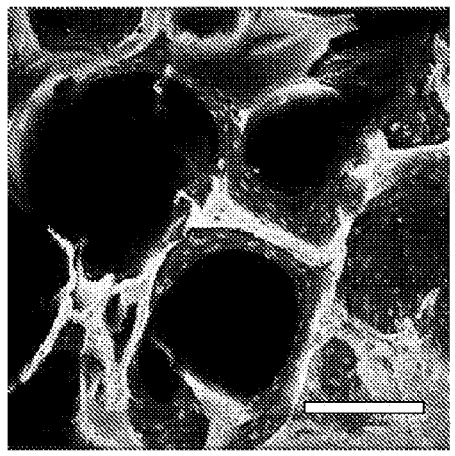
FIGS. 3A to 3I show confocal laser microscopic images of primary human fibroblast cell attachment, growth and proliferation on individual 3D meniscus silk scaffolds layers in chondrogenic medium.
Figure 3B:
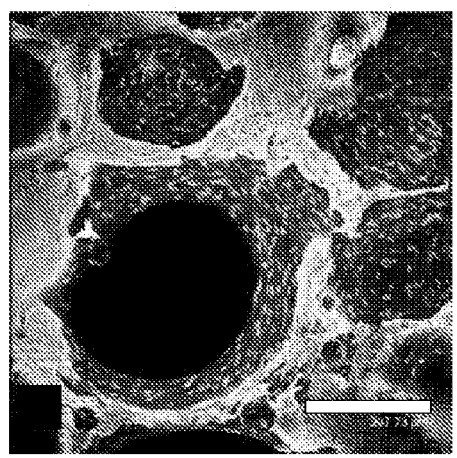
Figure 3C:
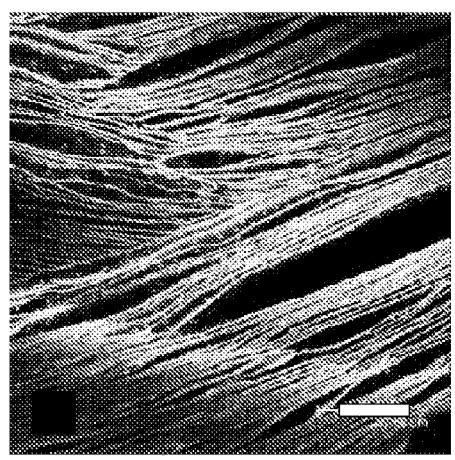
Figure 3D:
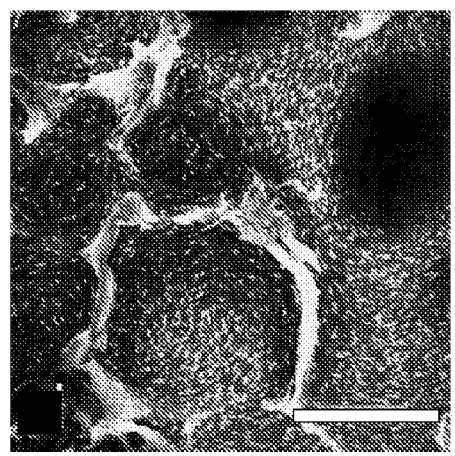
Figure 3E:
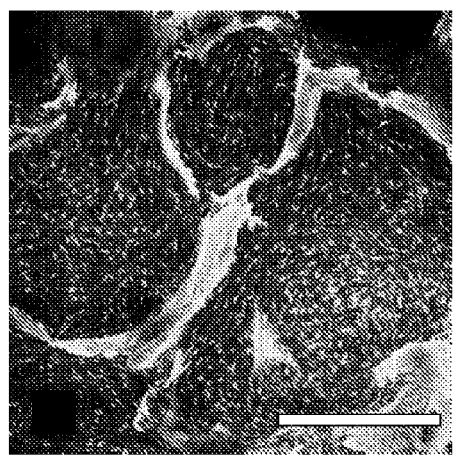
Figure 3F:
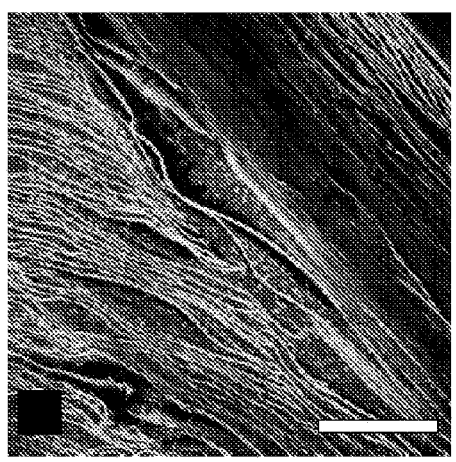
Figure 3G:
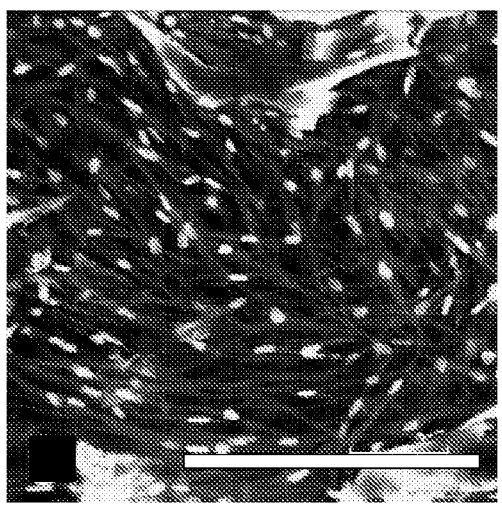
Figure 3H:
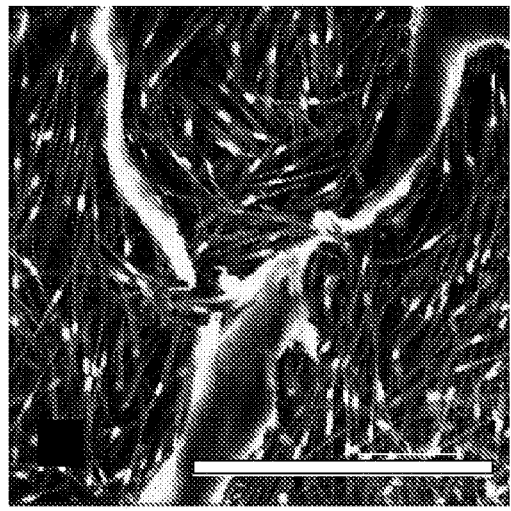
Figure 3I:
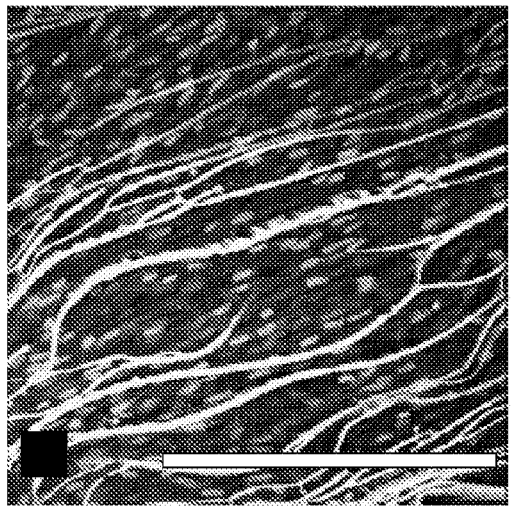
Figure 4A:
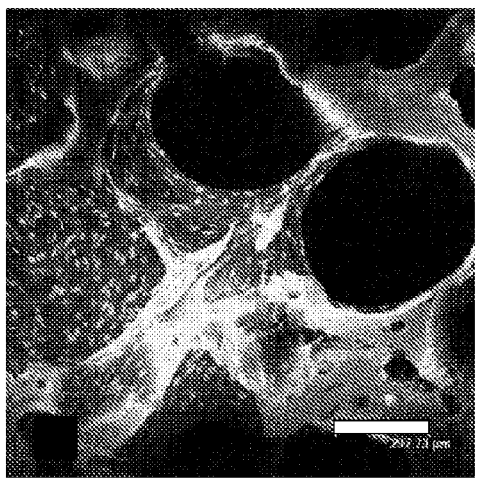
FIGS. 4A to 4I show confocal laser microscopic images of primary human chondrocyte cell attachment, growth and proliferation on individual 3D meniscus silk scaffolds layers in chondrogenic medium.
Figure 4B:
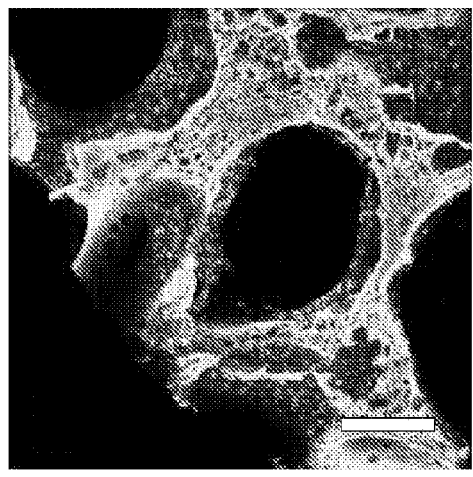
Figure 4C:
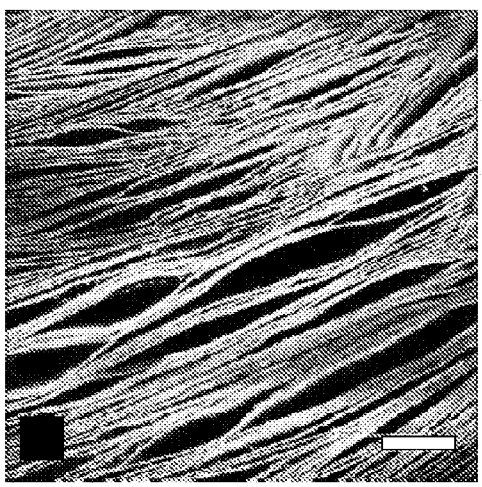
Figure 4D:
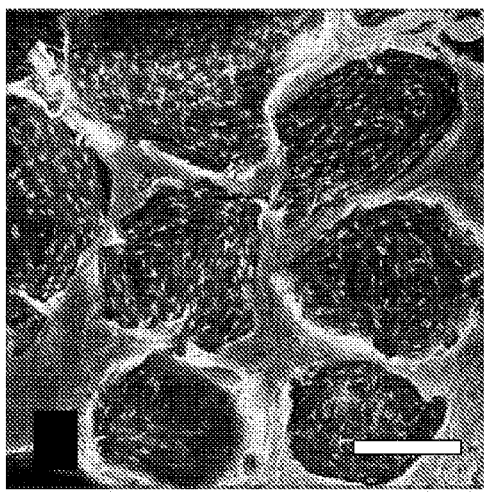
Figure 4E:
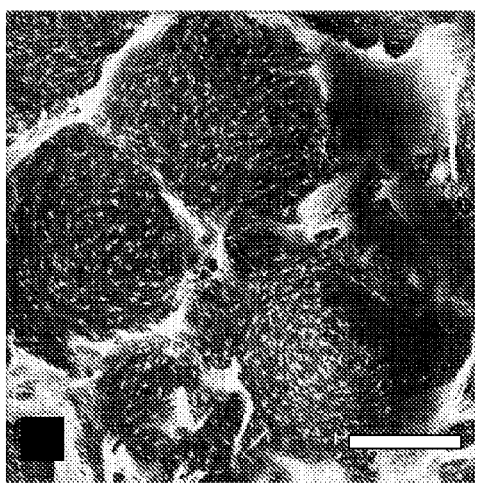
Figure 4F:
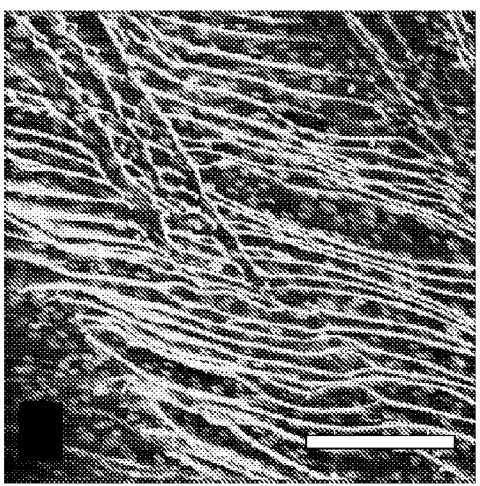
Figure 4G:
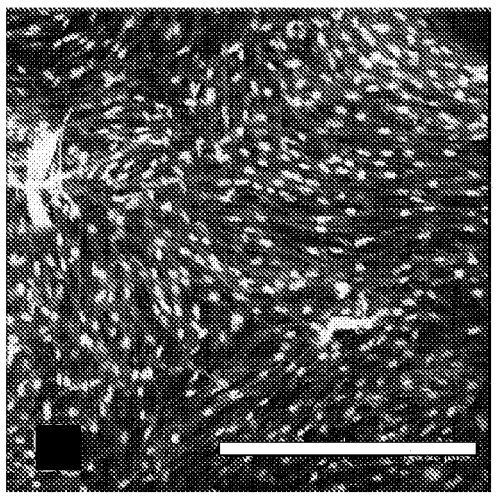
Figure 4H:
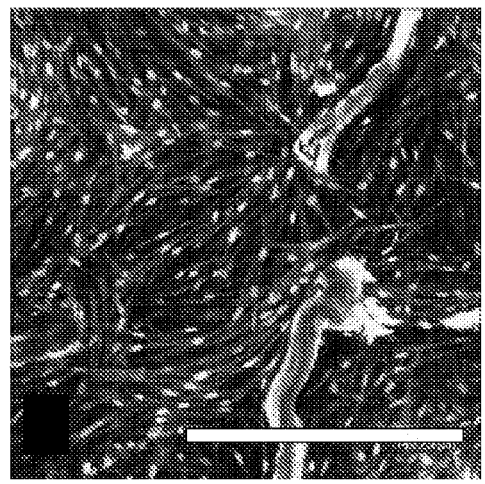
Figure 4I:
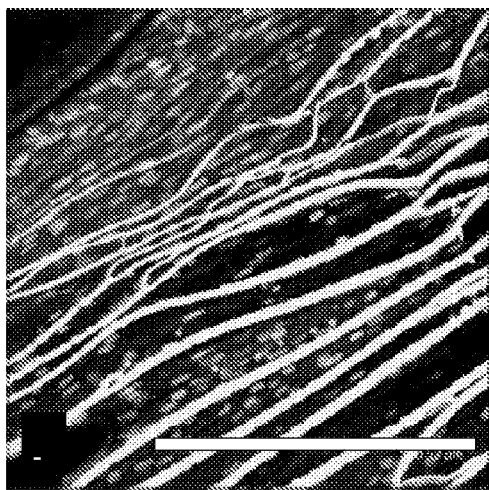

In some embodiments, separate individual layers (e.g., the first layer, the second layer, and/or optionally the third layer) can be stacked together to form a single composite unit. In such embodiments, the separate individual layers can be stacked together by any appropriate methods known in the art. For example, the individual layers can be stitched together, e.g., with at least one, at least two, or more biocompatible and/or biodegradable strings or fibers 202 (e.g., fibrin fibers, collagen fibers, silk fibroin fibers, or any combination thereof), as shown in FIG. 2. At least one stitch can be applied anywhere on any individual layer, e.g., around the periphery of the scaffold layer, or in the inner region of the scaffold layer. In some embodiments, the separate individual layers can be stacked together by a rivet approach, e.g., pushing at least one biocompatible and/or biodegradable plug (e.g., silk fibroin plug 204) into at least one hole 206, including at least two holes, or at least three holes, punched in each individual layers, wherein the hole(s) in each layer align with the hole(s) in the other layers, as shown in FIG. 2. In alternative embodiments, the separate individual layers can be glued together, e.g., with a biocompatible and/or biodegradable glue, e.g., without limitations, fibrin, silk fibroin, collagen, any other extracellular matrix molecules, and any combinations thereof. In some embodiments, the separate individual layers containing mammalian cells can be initially stacked and cultured together for a period of time, e.g., at least 3 days, to allow cell-secreted extracellular matrix to help self-adhesion between individual layers.

The silk fibroin scaffold can be adapted for meniscus repair or regeneration. In such embodiments, each silk fibroin scaffold layer can be crescent-shaped or C-shaped, as shown in FIGS. 1 and 2. In some embodiments, the silk fibroin scaffold can be wedge-shaped. The size of the crescent-shaped silk fibroin scaffold layer can vary with individual's knee size. Accordingly, the length 208 of a crescent-shaped silk fibroin scaffold described herein can vary from about 20 mm to about 60 mm, from about 30 mm to about 50 mm, or from about 35 mm to about 45 mm. The width 210 of a crescent-shaped silk fibroin scaffold described herein can vary from about 10 mm to about 40 mm, from about 15 mm to about 35 mm, or from about 20 mm to about 30 mm.

In some embodiments, the thickness of any individual silk fibroin scaffold layer can vary from 0.1 mm to about 5 mm, from about 0.5 mm to about 3 mm, or from about 1 mm to about 3 mm. In one embodiment, the thickness of any individual silk fibroin scaffold layer is about 2 mm.

Methods for Forming the Porous Silk Fibroin Scaffold Layers

As used herein, the term "silk fibroin" includes silkworm fibroin and other insect or spider silk protein. Lucas et al., 13 Adv. Protein Chem. 107-242 (1958). Silk fibroin can be obtained from a solution containing a dissolved silkworm silk or spider silk. The silkworm silk fibroins are obtained, for example, from the cocoon of *Bombyx mori*, and the spider silk fibroins are obtained, for example, from *Nephila clavipes*. In the alternative, the silk fibroins suitable for use in the present invention can be obtained from a solution containing a genetically engineered silk harvested from bacteria, yeast, mammalian cells, transgenic animals or transgenic plants. See, e.g., WO 97/08315; U.S. Pat. No. 5,245,012.

Any silk fibroin scaffold layers described herein can be prepared from an aqueous silk fibroin solution, which can be prepared from the silkworm cocoons using techniques known in the art. See, e.g., U.S. patent application Ser. No. 11/247,358; WO/2005/012606; WO/2008/127401. The silk aqueous solution can then be processed into silk fibroin matrices. Several processing techniques for preparing silk fibroin matrix have been reported, such as electrospinning (Jin et al., 3 Biomacromol. 1233-39 (2002)), sonication (Wang et al., 29 Biomats. 1054-64 (2008)) or chemical modification through covalent binding (Murphy et al., 29 Biomats. 2829-38 (2008)). These processes yield silk biomaterials that are formed and/or stabilized through β sheet assembly, with the mechanical properties and enzymatic degradation rates of silks depending on the size and distribution of these crystalline β sheet regions. See, e.g., Asakura et al., 42 Magn. Reson. Chem. 258-66 (2004). Such fibroin matrices can be used in conjunction with the silk fibroin-based ionomers of the present invention.

Silk polymer or silk fibroin solution can be prepared by any conventional method known to one skilled in the art. For example, *B. mori* cocoons are boiled for about 30 minutes in an aqueous solution. In one embodiment, the aqueous solution is about 0.02M $Na_2CO_3$. The cocoons are rinsed, for example with water, to extract the sericin proteins and the extracted silk is dissolved in an aqueous salt solution. Salts useful according to the present invention include, lithium bromide, lithium thiocyanate, calcium nitrate or other chemical capable of solubilizing silk. In one embodiment, the extracted silk is dissolved in about 9-12M LiBr solution. The salt is consequently removed using, for example, dialysis.

The silk polymer/fibroin solution is formed by mixing about 5% to 35% by weight of the silk fibroin with a solvent. In one embodiment, about 9% (w/v) of silk fibroin solution can be used. Solvents that can be used herein include hexafluoro-iso-propanyl (HFIP), N-methyl morpholine N-oxide and calcium nitrate-methanol. In one embodiment, the solvent is HFIP.

To form the first layer and/or the third layer as described herein, salt-porogen leaching method can be used, for example. The salt leaching method is detailed in the U.S. Patent Application No.: US 2010/0279112, the content of which is incorporated herein by reference in its entirety. The silk fibroin solution can be placed into a form, or mold, e.g., a crescent-shaped or C-shaped mold, containing water-soluble particles, or porogens, that are insoluble in organic solvents. Alternatively, the porogens can be mixed with the silk polymer solution prior to placement in the mold. The diameter of the particles (porogens) varies with the pre-determined pore sizes of the first layer and optionally the third layer described herein, e.g., between about 100 microns and about 1000 microns, between about 200 microns and about 700 microns, between 300 microns and about 600 microns, or a portion of any thereof. In one embodiment, the diameter of the particles (porogens) is about 350 microns to about 400 microns. In another embodiment, the diameter of the particles (porogens) is about 500 microns to about 600 microns. Examples of water-soluble porogens can be used herein include, NaCl, alkali metals, alkali earth metal halides, phosphates, and sulfates, sugar crystals, water-soluble microspheres, polysaccharides and protein microspheres.

In some embodiments, the solvent is removed using, for example, sublimation or evaporation.

In some embodiments, the silk fibroin mold/scaffold layers can be immersed in water or other solvent in which the particles, or porogens are soluble but silk fibroin is insoluble, to remove the particles (porogens), resulting in a porous three-dimensional first layer structure described herein.

To form the second layer as described herein, freeze-drying can be used, for example. The freeze-drying method is detailed in the U.S. Patent Application No.: US 2010/0279112, the content of which is incorporated herein by reference in its entirety. The silk fibroin solution put in a crescent-shaped or C-shaped mold can be frozen at sub-zero temperatures, e.g., from about −80° C. to about −20° C., for at least about 12 hours, at least about 24 hours, or longer, followed by lyophilization. In one embodiment, the silk fibroin solution is frozen from one direction. In some embodiments, the silk fibroin solution contains no salt. In some embodiments, alcohol such as 15%-25% of methanol or propanol can be added to the silk fibroin solution.

In some embodiments, the separate silk fibroin scaffold layers or a composite thereof can be subjected to post-treatment, e.g., to induce β-sheet structure and/or insolubility in aqueous solution. Such post-treatment include, but are not limited to, heat treatment, stretching, methanol or ethanol immersion, and any combinations thereof.

In some embodiments, silk fibroin can be modified for producing scaffold layers. One of skill in the art can select appropriate methods to modify silk fibroins, e.g., depending on the side groups of the silk fibroins, desired reactivity of the silk fibroin and/or desired charge density on the silk fibroin. In one embodiment, modification of silk fibroin can use the amino acid side chain chemistry, such as chemical modifications through covalent bonding, or modifications through charge-charge interaction. Exemplary chemical modification methods include, but are not limited to, carbodiimide coupling reaction (see, e.g. U.S. patent application Ser. No. 11/407,373), diazonium coupling reaction (see, e.g., U.S. patent application Ser. No. 12/192,588), and pegylation with a chemically active or activated derivatives of the PEG polymer (see, e.g., PCT/US09/64673). Silk fibroin can also be modified through gene modification to alter functionalities of the silk protein (see, e.g., U.S. application Ser. No. 61/224,618).

In some embodiments, the silk fibroin scaffolds can be also mixed with other biocompatible polymers to form mixed polymer scaffolds. One or more biocompatible polymers (e.g., two or more biocompatible polymers) can be added to the aqueous solution together with the silk fibroin. The biocompatible polymer that can be used herein include, but are not limited to, polyethylene oxide (PEO), polyethylene glycol (PEG), collagen, fibronectin, keratin, polyaspartic acid, polylysine, alginate, chitosan, chitin, hyaluronic acid, pectin, polycaprolactone, polylactic acid, polyglycolic acid, polyhydroxyalkanoates, dextrans, polyanhydrides, polymer, PLA-PGA, polyanhydride, polyorthoester, polycaprolactone, polyfumarate, collagen, chitosan, alginate, hyaluronic acid and other biocompatible polymers.

In some embodiments, at least one active agent described herein can be added to the silk aqueous solution before forming silk fibroin scaffold layers.

Cell Seeding

In some embodiments, the silk fibroin scaffold comprising individual layers described herein can comprise at least one mammalian cell, e.g., a human cell. In some embodiments, the silk fibroin scaffold comprising individual layers described herein can comprise a plurality of mammalian cells, e.g., human cells. Exemplary mammalian cells include, but are not limited to, fibroblasts, chondrocytes, meniscus fibrochondrocytes, stem cells, bone marrow stromal (stem) cells, embryonic stem cells, mesenchymal stem cells, induced pluripotent stem cells, differentiated stem cells, tissue-derived cells, smooth muscle cells, skeletal muscle cells, epithelial cells, endothelial cells, myoblasts, chondroblasts, osteoblasts, osteoclasts, and any combinations thereof.

Cells can be obtained from donors (allogenic) or from recipients (autologous). Cells can also be of established cell culture lines, or even cells that have undergone genetic engineering. Pieces of tissue can also be used, which may provide a number of different cell types in the same structure.

The cells can be obtained from any suitable donor, either human or animal, or from the subject into which they are to be implanted. Mammalian species include, but are not limited to, humans, monkeys, dogs, cows, horses, pigs, sheep, goats, cats, mice, rabbits, rats. In one embodiment, the cells are human cells. In other embodiments, the cells can be derived from animals such as, dogs, cats, horses, monkeys, or any other mammal.

Without wishing to be bound by theory, the number of cells seeded does not limit the final tissue (e.g., meniscus) produced, however optimal seeding can increase the rate of generation. The number of seeded cells can be optimized using dynamic seeding (Vunjak-Novakovic et al. Biotechnology Progress 1998; Radisic et al. Biotechnoloy and Bioengineering 2003).

Figure 8:
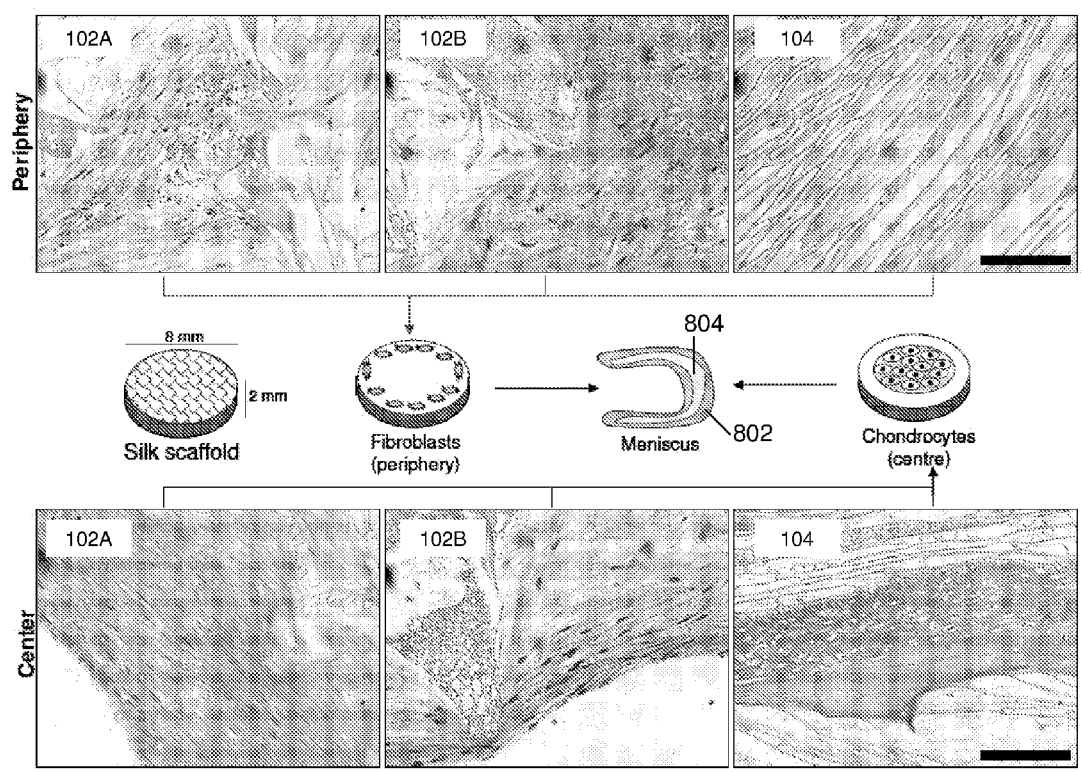
FIG. 8 shows a schematic representation showing central and peripheral cell seeding on silk scaffold layers mimicking native meniscus tissue cell organization along with histology sections showing matured tissue outcomes. Scale bar represents 100 microns.

The at least one mammalian cell can be present anywhere within the silk fibroin scaffold, e.g., within the first layer, within the second layer, and/or optionally within the third layer. In some embodiments, to mimic native meniscus fibrocartilaginous structure, different types of cells can be spatially placed in certain regions of the silk fibroin scaffold. For example, in some embodiments, one or more fibroblasts can be placed around at least a portion of the periphery 802 of the silk fibroin scaffold and/or the individual layers thereof, e.g., to create the fibrous region of the meniscus, e.g., as shown in FIG. 8. As used herein, the term "periphery" refers to at least the outer one-third volume (space) of the silk fibroin scaffold and/or the individual layers thereof, including the surface and the pores therein. In some embodiments, one or more fibroblasts can be placed around at least about 10%, at least about 20%, at least about 30%, at least about 40%, at least about 50%, at least about 60%, at least about 70%, at least about 80%, at least about 90%, at least about 95%, at least about 98%, at least about 99% or 100% of the periphery of the silk fibroin scaffold and/or the individual layers thereof. In further embodiments, one or more chondrocytes can be placed in at least a portion of the inner region 804 (or center region) of the silk fibroin scaffold and/or individual layers thereof, e.g., to represent cartilage portion of the meniscus, as shown in FIG. 8. As used herein, the term "inner region" or "center region" refers to any volume or space (including the surface and pores therein) that is not the periphery of the silk fibroin scaffold or the individual layers thereof. In some embodiments, the term "inner region" refers to the volume or space (including the surface and pores therein) surrounded by the periphery of the silk fibroin scaffold and/or the individual layers thereof. In some embodiments, one or more chondrocytes can be placed around at least about 10%, at least about 20%, at least about 30%, at least about 40%, at least about 50%, at least about 60%, at least about 70%, at least about 80%, at least about 90%, at least about 95%, at least about 98%, at least about 99% or 100% of the inner region of the silk fibroin scaffold and/or the individual layers thereof. Cells can be placed into a pre-determined region, e.g., by directly injecting the cells into the target site of the silk fibroin scaffold or any individual layers thereof, or any other methods known in the art. In some embodiments, at least one protein gradient and/or chemotactic agent gradient can be formed within the silk fibroin scaffold using the methods of forming an immobilized agent gradient within a 3-dimensional porous scaffold disclosed in the U.S. Patent Application No.: US 2007/0212730, the content of which is incorporated herein by reference in its entirety, such that two different cell types, e.g., fibroblasts and chonodrocytes can be preferentially attracted to their appropriate chemotactic agent. By way of example only, two different protein or chemotactic agents (e.g., one specific for fibroblasts, and another for chondrocytes) can be immobilized around the outer region and in the inner region of the silk fibroin scaffold, respectively, thus creating increasing concentrations of gradients moving toward opposite ends, such that fibroblasts and chondrocytes can independently direct their migration toward the chemotactic agent they preferentially favor.

In alternative embodiments, one or more stem cells, e.g., bone marrow stem cells, can be placed within at least a portion of the silk fibroin scaffold and/or the individual layers thereof. In some embodiments, one or a plurality of stem cells can be placed within at least about 10%, at least about 20%, at least about 30%, at least about 40%, at least about 50%, at least about 60%, at least about 70%, at least about 80%, at least about 90%, at least about 95%, at least about 98%, at least about 99% or 100% of the silk fibroin scaffold and/or the individual layers thereof. At least a portion of the stem cells can then be differentiated to a chondrogenic phenotype, e.g., at least about 10%, at least about 20%, at least about 30%, at least about 40%, at least about 50%, at least about 60%, at least about 70%, at least about 80%, at least about 90%, at least about 95%, at least about 98%, at least about 99%, or 100% of the stem cells can be differentiated to a chondrogenic phenotype. A skilled artisan can readily perform differentiating stem cells into a chondrogenic phenotype, e.g., exposing them to art-recognized cell differentiation factors and/or commercially-available differentiation media as described in the Methods and Materials of the EXAMPLES section. In some embodiments, before placing the stem cells into the silk fibroin scaffold, at least one or at least two protein or cell differentiation factor gradients can be formed within the silk fibroin scaffold, e.g., using the methods disclosed in the U.S. Patent Application No.: US 2007/0212730, the content of which is incorporated herein by reference in its entirety. The stem cells can then be differentiated in response to the local gradient of the cell differentiation factor. Methods for monitoring stem cell differentiation are well known in the art, e.g., measuring gene expression specific for chondrogenic phenotypes such as collagen-1-alpha-1, aggrecan, collagen-X-alpha-1, SOX9 and any other art-recognized genes, as described in the EXAMPLES.

In some embodiments, the mammalian cells can be seeded or placed into any of the separate individual layers. After seeding, the separate individual layers can be cultured independently as separate layers or they can be stacked together and cultured as a single composite unit. In some embodiments, the mammalian cells can be seeded or placed after the separate individual layers form a single composite unit.

Appropriate growth conditions for mammalian cells are well known in the art (Freshney, R. I. (2000) Culture of Animal Cells, a Manual of Basic Technique. Hoboken N.J., John Wiley & Sons; Lanza et al. Principles of Tissue Engineering, Academic Press; 2nd edition May 15, 2000; and Lanza & Atala, Methods of Tissue Engineering Academic Press; 1st edition October 2001). Cell culture media generally include essential nutrients and, optionally, additional elements such as growth factors, salts, minerals, vitamins, etc., that may be selected according to the cell type(s) being cultured. Particular ingredients may be selected to enhance cell growth, differentiation, secretion of specific proteins, etc. In general, standard growth media include Dulbecco's Modified Eagle Medium, low glucose (DMEM), with 110 mg/L pyruvate and glutamine, supplemented with 10-20% fetal bovine serum (FBS) or calf serum and 100 U/ml penicillin are appropriate as are various other standard media well known to those in the art. Growth conditions will vary dependent on the type of mammalian cells in use and tissue desired.

The growth period can be continued until the silk fibroin scaffold and/or layers have attained desired properties, e.g., until the scaffold layer has reached a particular thickness, size, strength, composition of proteinaceous components, and/or a particular cell density. Methods for assessing these parameters are known to those skilled in the art. In some embodiments, the cells can be cultured for at least about 6 hours, at least about 12 hours, at least about 24 hours, at least about 2 days, at least about 3 days, at least about 4 days, at least about 5 days, at least about 6 days, at least about 1 week, or longer.

Following a first growth period the construct can be seeded with a second population of cells, which may comprise cells of the same type as used in the first seeding or cells of a different type. The construct can then be maintained for a second growth period which may be different in length from the first growth period and may employ different growth conditions. Multiple rounds of cell seeding with intervening growth periods may be employed.

The cells that are used for methods described herein should be derived from a source that is compatible with the intended recipient. The cells are dissociated using standard techniques and seeded onto and into the scaffold. In vitro culturing optionally can be performed prior to implantation. Alternatively, the scaffold can be implanted into the subject, allowed to vascularize, then cells can be injected into the scaffold. Methods and reagents for culturing cells in vitro and implantation of a tissue scaffold are known to those skilled in the art.

The formation of meniscus tissue (fibrous- and cartilage-like tissues) can be monitored by assays well known to those in the art including, but not limited to, histology, immunohistochemistry, and confocal or scanning electron microscopy (Holy et al., J. Biomed. Mater. Res (2003) 65A:447-453).

It is another aspect of the invention that the biocompatible implant, described herein, can itself be implanted in vivo and serve as tissue substitute (e.g. to substitute for meniscus). Such implants, can require no seeding of cells, but contain a chemotatic agent or cell attachment molecules, e.g., RGD, that attracts fibroblasts or chondrocytes.

Active Agents

Silk fibroin can stabilize bioactivity of active agents, even at body temperatures. Therefore, in some embodiments, the biocompatible implant and/or the silk fibroin scaffold described herein can further comprise at least one active agent. Examples of such active agents can include, but are not limited to, TGF-β1, TGF-β2, TGF-β3, BMP-2, BMP-4, BMP-6, BMP-12, BMP-13, basic fibroblast growth factor, fibroblast growth factor-1, fibroblast growth factor-2, platelet-derived growth factor-AA, platelet-derived growth factor-BB, platelet rich plasma, IGF-I, IGF-II, GDF-5, GDF-6, GDF-8, GDF-10, vascular endothelial cell-derived growth factor, pleiotrophin, endothelin, nicotinamide, glucagon like peptide-I, glucagon like peptide-II, parathyroid hormone, tenascin-C, tropoelastin, thrombin-derived peptides, laminin, biological peptides containing cell-binding domains and biological peptides containing heparin-binding domains, therapeutic agents, and any combinations thereof.

The term "therapeutic agents" is art-recognized and refers to any chemical moiety that is a biologically, physiologically, or pharmacologically active substance that acts locally or systemically in a subject. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent can be used which are capable of being released from the silk fibroin scaffold described herein into adjacent tissues or fluids upon implantation to a subject. Examples of therapeutic agents include, but are not limited to, antibiotics, anesthetics, any therapeutic agents that promote meniscus regeneration or tissue healing, or reduce pain, infection, or inflammation, or any combinations thereof.

Additional active agents can include, but are not limited to, proteins, peptides, nucleic acid analogues, nucleotides, oligonucleotides, nucleic acids (DNA, RNA, siRNA), peptide nucleic acids, aptamers, antibodies or fragments or portions thereof, antigens or epitopes, hormones, hormone antagonists, growth factors or recombinant growth factors and fragments and variants thereof, cytokines, enzymes, antibiotics or antimicrobial compounds, anti-inflammation agent, antifungals, antivirals, toxins, prodrugs, small molecules, drugs (e.g., drugs, dyes, amino acids, vitamins, antioxidants) and combinations thereof.

Exemplary antibiotics suitable for inclusion in the silk fibroin scaffold and/or the biocompatible implant of the present invention include, but are not limited to, aminoglycosides (e.g., neomycin), ansamycins, carbacephem, carbapenems, cephalosporins (e.g., cefazolin, cefaclor, cefditoren, cefditoren, ceftobiprole), glycopeptides (e.g., vancomycin), macrolides (e.g., erythromycin, azithromycin), monobactams, penicillins (e.g., amoxicillin, ampicillin, cloxacillin, dicloxacillin, flucloxacillin), polypeptides (e.g., bacitracin, polymyxin B), quinolones (e.g., ciprofloxacin, enoxacin, gatifloxacin, ofloxacin, etc.), sulfonamides (e.g., sulfasalazine, trimethoprim, trimethoprim-sulfamethoxazole (co-trimoxazole)), tetracyclines (e.g., doxycyline, minocycline, tetracycline, etc.), chloramphenicol, lincomycin, clindamycin, ethambutol, mupirocin, metronidazole, pyrazinamide, thiamphenicol, rifampicin, thiamphenicl, dapsone, clofazimine, quinupristin, metronidazole, linezolid, isoniazid, fosfomycin, or fusidic acid.

Exemplary antibodies include, but are not limited to, abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, and zanolimumab.

Exemplary enzymes suitable for use herein include, but are not limited to, peroxidase, lipase, amylose, organophosphate dehydrogenase, ligases, restriction endonucleases, ribonucleases, DNA polymerases, glucose oxidase, and laccase.

Additional active agents to be used herein include cell growth media, such as Dulbecco's Modified Eagle Medium, fetal bovine serum, non-essential amino acids and antibiotics; growth and morphogenic factors such as fibroblast growth factor, transforming growth factors, vascular endothelial growth factor, epidermal growth factor, platelet derived growth factor, insulin-like growth factors), bone morphogenetic growth factors, bone morphogenetic-like proteins, transforming growth factors, nerve growth factors, and related proteins (growth factors are known in the art, see, e.g., Rosen & Thies, CELLULAR & MOLECULAR BASIS BONE FORMATION & REPAIR (R.G. Landes Co., Austin, Tex., 1995); anti-angiogenic proteins such as endostatin, and other naturally derived or genetically engineered proteins; polysaccharides, glycoproteins, or lipoproteins; anti-infectives such as antibiotics and antiviral agents, chemotherapeutic agents (i.e., anticancer agents), anti-rejection agents, analgesics and analgesic combinations, anti-inflammatory agents, and steroids.

Methods for Repairing a Meniscal Defect

Any biocompatible implant described herein can be implanted into a subject in need thereof for a meniscus repair or regeneration. Accordingly, methods of repairing a meniscal defect or promoting mensical regeneration in a subject are also provided herein. In one embodiment, the method comprises implanting a biocompatible implant described herein into a defect site in need of meniscus repair or regeneration.

The term "subject" includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered. In one embodiment, the subject is a mammal. In one embodiment, the subject is a human subject.

When the individual layers of the silk fibroin scaffold are separate and are not assembled together as a single unit, they can be stacked together using any of the methods described herein before implanting it into the subject. In some embodiments, the treatment method can further comprise securing the biocompatible implant in the defect site. In some embodiments, the treatment method can further comprise removing at least a portion of a defective meniscus from the subject.

In some embodiments, the treatment method can further comprise placing one or more mammalian cells described herein (e.g., chondrocytes, fibroblasts, and/or stem cells) in the defect site, e.g., after implanting the biocompatible implant into the subject, or by placing the cells into the silk fibroin scaffold before implantation.

In various embodiments, the treatment method can further comprise administering to the subject or to the defect site at least one active agent described herein.

The present invention may be defined in any of the following numbered paragraphs:
1. A biocompatible implant comprising: a silk fibroin scaffold having at least a first layer and a second layer, wherein each of the first layer and the second layer has a distinct pore size distribution and pore orientation.
2. The biocompatible implant of paragraph 1, wherein the silk fibroin scaffold further comprises at least one mammalian cell.
3. The biocompatible implant of paragraph 2, wherein the mammalian cells are human cells.
4. The biocompatible implant of any of paragraphs 2-3, wherein the mammalian cells are selected from the group consisting of fibroblasts, chondrocytes, stem cells, bone marrow cells, embryonic stem cells, mesenchymal stem cells, induced pluripotent stem cells, differentiated stem cells, tissue-derived cells, and any combinations thereof.
5. The biocompatible implant of any of paragraphs 2-4, wherein periphery of the silk fibroin scaffold comprises at least one fibroblast.
6. The biocompatible implant of any of paragraphs 2-5, wherein an inner region of the silk fibroin scaffold comprises at least one chondrocyte.
7. The biocompatible implant of any of paragraphs 2-6, wherein the silk fibroin scaffold comprise at least one stem cell.
8. The biocompatible implant of any of paragraphs 1-7, wherein the first layer comprises approximately circular pores.
9. The biocompatible implant of paragraph 8, wherein the approximately circular pores are at least partially interconnected.
10. The biocompatible implant of any of paragraphs 1-9, wherein the pore size distribution of the first layer ranges from about 100 microns to about 1000 microns, or a portion thereof.
11. The biocompatible implant of paragraph 10, wherein the pore size distribution of the first layer ranges from about 200 microns to about 700 microns, or a portion thereof.
12. The biocompatible implant of paragraph 11, wherein the pore size distribution of the first layer ranges from about 300 microns to about 600 microns, or a portion thereof.
13. The biocompatible implant of any of paragraphs 8-12, wherein the approximately circular pores are distributed within the first layer to form two or more distinct sub-layers, each sub-layer having a distinct pore size distribution.
14. The biocompatible implant of paragraph 13, wherein the sub-layer closer to the second layer has a larger pore size distribution than the other sub-layers.
15. The biocompatible implant of paragraph 14, wherein the larger pore size distribution ranges from about 500 microns to about 700 microns.
16. The biocompatible implant of any of paragraph 1-15, wherein the silk fibroin scaffold further comprises a third layer.
17. The biocompatible implant of paragraph 16, wherein the third layer comprises approximately circular pores with a pore size distribution ranging from about 500 microns to about 700 microns.
18. The biocompatible implant of any of paragraphs 1-17, wherein the second layer comprises laminar channels.
19. The biocompatible implant of paragraph 18, wherein the laminar channels are at least partially aligned.
20. The biocompatible implant of any of paragraphs 18-19, wherein the laminar channels have a pore width distribution ranging between about 30 microns and about 100 microns, or a portion thereof.
21. The biocompatible implant of paragraph 20, wherein the laminar channels have a pore width distribution ranging between about 60 microns and about 80 microns, or a portion thereof.

22. The biocompatible implant of any of paragraphs 1-21, wherein the porosity of each layer is independently at least about 30%.
23. The biocompatible implant of any of paragraphs 1-22, wherein said each layer is individually formed before stacking together into a single composite unit.
24. The biocompatible implant of paragraph 23, wherein the stacking is further supported by stitching said each layer together to form the single composite unit.
25. The biocompatible implant of paragraph 24, wherein the stitching uses at least one silk fibroin fiber.
26. The biocompatible implant of any of paragraphs 23-25, wherein the stacking is further supported by riveting.
27. The biocompatible implant of paragraph 26, wherein the riveting uses at least one silk fibroin plug to hold said each layer together to form the single composite unit.
28. The biocompatible implant of any of paragraphs 23-27, wherein the stacking is further supported with a biocompatible glue.
29. The biocompatible implant of paragraph 28, wherein the biocompatible glue is biodegradable.
30. The biocompatible implant of paragraph 28 or 29, wherein the biocompatible glue is fibrin, silk fibroin, collagen or any combinations thereof.
31. The biocompatible implant of any of paragraphs 1-30, further comprising at least one extracellular matrix.
32. The biocompatible implant of paragraph 31, wherein the extracellular matrix is produced by said at least one mammalian cell present in the silk fibroin scaffold.
33. The biocompatible implant of any of paragraphs 1-32, further comprising at least one active agent.
34. The biocompatible implant of paragraph 33, wherein the at least one active agent is selected from the group consisting of TGF-β1, TGF-β2, TGF-β3, BMP-2, BMP-4, BMP-6, BMP-12, BMP-13, basic fibroblast growth factor, fibroblast growth factor-1, fibroblast growth factor-2, platelet-derived growth factor-AA, platelet-derived growth factor-BB, platelet rich plasma, IGF-I, IGF-II, GDF-5, GDF-6, GDF-8, GDF-10, vascular endothelial cell-derived growth factor, pleiotrophin, endothelin, nicotinamide, glucagon like peptide-I, glucagon like peptide-II, parathyroid hormone, tenascin-C, tropoelastin, thrombin-derived peptides, laminin, biological peptides containing cell-binding domains and biological peptides containing heparin-binding domains, therapeutic agents, and any combinations thereof.
35. The biocompatible implant of any of paragraphs 1-34, wherein the silk fibroin scaffold is adapted for meniscus repair or regeneration.
36. The biocompatible implant of paragraph 35, wherein each layer of the silk fibroin scaffold is crescent-shaped.
37. A method of repairing a meniscal defect or promoting mensical regeneration in a subject, comprising implanting a biocompatible implant of any of paragraphs 1-36 into a defect site in need of meniscus repair or regeneration.
38. The method of paragraph 37, further comprising securing the biocompatible implant in the defect site.
39. The method of paragraph 37 or 38, further comprising removing at least a portion of a defective meniscus from the subject.
40. The method of any of paragraphs 37-39, further placing at least one mammalian cell in the defect site.
41. The method of paragraph 40, wherein the at least one mammalian cell is a chondrocyte, a fibrochondrocyte, a fibroblast, a stem cell, or any combinations thereof.
42. The method of any of paragraphs 37-41, further comprising administering at least one active agent to the subject or the defect site.
43. The method of paragraph 42, wherein the at least one active agent is selected from the group consisting of TGF-β1, TGF-β2, TGF-β3, BMP-2, BMP-4, BMP-6, BMP-12, BMP-13, basic fibroblast growth factor, fibroblast growth factor-1, fibroblast growth factor-2, platelet-derived growth factor-AA, platelet-derived growth factor-BB, platelet rich plasma, IGF-I, IGF-II, GDF-5, GDF-6, GDF-8, GDF-10, vascular endothelial cell-derived growth factor, pleiotrophin, endothelin, nicotinamide, glucagon like peptide-I, glucagon like peptide-II, parathyroid hormone, tenascin-C, tropoelastin, thrombin-derived peptides, laminin, biological peptides containing cell-binding domains and biological peptides containing heparin-binding domains, therapeutic agents, extracellular matrix and any combinations thereof.
44. A method of producing a biocompatible implant comprising:
forming a silk fibroin scaffold having at least a first layer and a second layer, wherein each of the first layer and the second layer has a distinct pore size distribution and orientation.
45. The method of paragraph 44, further comprising the step of placing at least one mammalian cell within the silk fibroin scaffold.
46. The method of paragraph 45, wherein the at least one mammalian cell is a human cell.
47. The method of paragraph 45 or 46, wherein the at least one mammalian cell is selected from the group consisting of fibroblasts, chondrocytes, stem cells, bone marrow cells, embryonic stem cells, mesenchymal stem cells, induced pluripotent stem cells, differentiated stem cells, tissue-derived cells, and any combinations thereof.
48. The method of any of paragraphs 45-47, wherein the placing step comprises placing at least a portion of a periphery of the silk fibroin scaffold with fibroblasts.
49. The method of any of paragraphs 45-48, wherein the placing step comprises placing at least a portion of the inner region of the silk fibroin scaffold with chondrocytes.
50. The method of any of paragraphs 45-49, wherein the placing step comprises placing at least a portion of the silk fibroin scaffold with stem cells.
51. The method of paragraph 50, further comprising differentiating the stem cells into a chondrogenic phenotype.
52. The method of any of paragraphs 44-51, wherein the forming step comprises forming approximately circular pores within the first layer.
53. The method of paragraph 52, wherein the pore size distribution of the first layer ranges from about 100 microns to about 1000 microns, or a portion thereof.
54. The method of paragraph 53, wherein the pore size distribution of the first layer ranges from about 200 microns to about 700 microns, or a portion thereof.
55. The method of paragraph 54, wherein the pore size distribution of the first layer ranges from about 300 microns to about 600 microns, or a portion thereof.
56. The method of any of paragraphs 52-55, wherein forming the approximately circular pores are distributed to form two or more distinct sub-layers with different pore size distributions.
57. The method of paragraph 56, wherein the sub-layer closer to the second layer has a larger pore size distribution than the other sub-layers.

58. The method of paragraph 57, wherein the larger pore size distribution ranges from about 500 microns to about 700 microns.
59. The method of any of paragraphs 44-58, wherein the forming step comprises forming laminar channels within the second layer.
60. The method of paragraph 59, wherein the laminar channels are at least partially aligned.
61. The method of any of paragraphs 59-60, wherein the laminar channels have a pore width distribution ranging between about 30 microns and about 100 microns, or a portion thereof.
62. The method of paragraph 61, wherein the laminar channels have a pore width distribution ranging between about 60 microns and about 80 microns, or a portion thereof.
63. The method of any of paragraphs 59-62, wherein the laminar channels within the second layer are formed by a freeze-drying method.
64. The method of any of paragraphs 44-64, further comprising forming at least a third layer.
65. The method of paragraph 64, wherein said at least the third layer comprises approximately circular pores with a pore size distribution of about 500 microns to about 700 microns, or a portion thereof.
66. The method of any of paragraphs 44-65, wherein the approximately circular pores are formed by a salt-leaching method.
67. The method of any of paragraphs 44-66, wherein the porosity of each layer is independently at least about 30%.
68. The method of any of paragraphs 44-67, further comprising stacking said each layer together into a single unit.
69. The method of paragraph 68, wherein the stacking is performed by stitching said each layer together to form the single unit.
70. The method of paragraph 69, wherein the stitching uses at least one silk fibroin fiber.
71. The method of any of paragraphs 68-70, wherein the stacking is performed by riveting.
72. The method of paragraph 71, wherein the riveting uses at least one silk fibroin plug to hold said each layer together to form the single unit.
73. The method of any of paragraphs 68-72, wherein the stacking is performed with a biocompatible glue.
74. The method of paragraph 73, wherein the biocompatible glue is biodegradable.
75. The method of paragraph 73 or 74, wherein the biocompatible glue is fibrin, silk fibroin, collagen or any combinations thereof.
76. The method of any of paragraphs 44-75, further comprising adding at least one active agent into the silk fibroin scaffold or the biocompatible implant.
77. The method of paragraph 76, wherein the at least one active agent is selected from the group consisting of TGF-$\beta$1, TGF-$\beta$2, TGF-$\beta$3, BMP-2, BMP-4, BMP-6, BMP-12, BMP-13, fibroblast growth factor-1, fibroblast growth factor-2, platelet-derived growth factor-AA, platelet-derived growth factor-BB, platelet rich plasma, IGF-I, IGF-II, GDF-5, GDF-6, GDF-8, GDF-10, vascular endothelial cell-derived growth factor, pleiotrophin, endothelin, nicotinamide, glucagon like peptide-I, glucagon like peptide-II, parathyroid hormone, tenascin-C, tropoelastin, thrombin-derived peptides, laminin, biological peptides containing cell-binding domains and biological peptides containing heparin-binding domains, therapeutic agents, extracellular matrix, and any combinations thereof.
78. The method of any of paragraphs 44-77, wherein the forming step further comprises configuring the silk fibroin scaffold for use in meniscus repair or regeneration.
79. The method of paragraph 78, wherein the configuring comprises fabricating said each layer of the silk fibroin scaffold in a shape of a meniscus.
80. The method of paragraph 79, wherein the shape of a meniscus is crescent-shaped.
81. The method of any of paragraphs 44-80, wherein the placing step further comprises culturing the at least one mammalian cell within the silk fibroin scaffold for a period of time.
82. The method of paragraph 81, wherein the period of time is at least about 24 hours.
83. The method of any of paragraphs 81-82, wherein the culturing step is performed before the stacking of each layer into a single unit.
84. The method of any of paragraphs 44-83, further comprising post-treatment of the silk fibroin scaffold or each layer individually.
85. The method of paragraph 84, wherein the post-treatment is selected from the group consisting of heat treatment, stretching, methanol or ethanol immersion, and any combinations thereof.
86. The method of any of paragraphs 44-85, further comprising forming an immobilized agent gradient within the silk fibroin scaffold.

As used herein, the term "comprising" means that other elements can also be present in addition to the defined elements presented. The use of "comprising" indicates inclusion rather than limitation.

Other than in the operating examples, or where otherwise indicated, all numbers expressing quantities of ingredients or reaction conditions used herein should be understood as modified in all instances by the term "about." The term "about" when used in connection with percentages may mean±1%.

The singular terms "a," "an," and "the" include plural references unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Unless otherwise explained, all technical and scientific terms used herein have the same meaning as commonly understood by one of ordinary skill in the art to which this disclosure belongs.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

All patents and other publications identified throughout the specification are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

This invention is further illustrated by the following example which should not be construed as limiting.

The contents of all references cited throughout this application, examples, as well as the figures and tables are incorporated herein by reference in their entirety.

EXAMPLES

Materials and Methods (for Examples 1-5)

Preparation of Silk Fibroin Solution.

A 9 w/v % silk fibroin solution was obtained from *Bombyx mori* silkworm cocoons that were extracted in a 0.02M $Na_2CO_3$ solution, dissolved in 9.3M LiBr solution and subsequently dialyzed against distilled water (Kim et al., 2005).

Meniscus Scaffolds Preparation.

In order to mimic heterogeneous pore orientation of natural meniscus, 3D aqueous-derived silk scaffolds were fabricated into individual layers with different pore size and orientations accordingly. Out of the total 3 layers, the first two layers were fabricated according to the salt leaching procedure described herein or in U.S. Patent Application No.: US 2010/0279112, while third layer was achieved using freeze drying method described herein or in U.S. Patent Application No.: US 2010/0279112 and Kim et al., 2005. Briefly, for salt leached method, two grams of granular NaCl particles (350-400 and 500-600 microns for first and second layers respectively) was added per 1 ml of 9 w/v % silk fibroin solution in meniscus shaped PDMS (polydimethylsiloxane, GE plastics) moulds at room temperature. Twenty-four hours later the moulds were immersed in water to extract the salt from the porous scaffolds over 2 days. Similarly, for freeze dried third scaffold layer, no salt was added instead the silk solution was frozen at −20° C. for overnight followed by lyophilization.

Chondrocyte and Fibroblast Expansion.

Adult human articular chondrocytes and primary human dermal fibroblast cells were obtained from consenting donors <35 years of age (Lonza, Walkersville, Md.). The cells were expanded in growth medium containing 90% high glucose Dulbecco's modified Eagle's medium (DMEM), 10% fetal bovine serum (FBS), 0.1 mM nonessential amino acids, 0.29 mg/ml L-glutamate, 1×PSF (100 units/ml Penicillin, 100 µg/ml Streptomycin, 0.25 µg/ml Fungizone) and 1 ng/ml beta fibroblast growth factor (bFGF, Invitrogen, Carlsbad, Calif.). Adherent cells formed numerous colonies with time, and were subsequently expanded in the ratio of 1:3. For subsequent experiments, P8 chondrocyte cells were used. Late passage cells were deliberately used as a stringent test for the fabricated silk construct to check its ability to maintain chondrocyte phenotype and ECM expression.

hMSC Isolation and Expansion.

hMSCs were obtained from bone marrow aspirates (Cambrex Bio Science Walkersville, Inc.) from a 25 yr old healthy male and processed as previously reported in Altman et al., 2002. Whole bone marrow aspirates were plated at a density of 10 µL of aspirate per centimeter squared in 185 $cm^2$ tissue culture flasks in Dulbecco's Modified Eagle Medium (DMEM) supplemented with 10% fetal bovine serum (FBS), penicillin (100 U/mL), streptomycin (100 µg/mL), 0.1 mM non-essential amino acids, and basic fibroblast growth factor (bFGF, 1 ng/mL) (Invitrogen, Carlsbad, Calif.). This medium was termed as growth medium. Cells were maintained in a humidified incubator at 37° C. with 5% $CO_2$. hMSCs were separated from hematopoietic stem cells on the basis of their adherence to tissue culture plastic; hematopoietic stem cells in suspension were removed after approximately 5 days of culture. hMSCs formed numerous colonies with time, and were subsequently expanded in the ratio of 1:3. For subsequent experiments, P7 hMSCs were used. Late passage cells were deliberately used as a stringent test to check its ability to differentiate into chondrogenic phenotype and ECM expression on the fabricated silk constructs.

Cell Seeding and Culture on Scaffold Layers: Fibroblasts and Chrondrocytes.

To produce cell-seeded meniscal equivalent constructs, scaffolds were cultured with human primary fibroblasts (periphery of scaffolds) and human primary chondrocytes (center or inner region of scaffolds) mimicking cell distribution as present in native meniscal tissues (Buma et al., 2004 and Verdonk et al., 2005). To manage the cell numbers needed, instead of crescent meniscus shape, the scaffolds were cut into discs (8 mm in diameter and 2 mm in thickness) for the study. For cell seeding, the scaffolds were disinfected, washed in sterile PBS and conditioned with DMEM for overnight before cell seeding. To monitor the response of different meniscus layers in terms of ECM deposition and cell proliferation, both cells types were individually seeded in each scaffold layers separately. To seed scaffolds, 20 µl aliquots containing $1 \times 10^6$ fibroblasts and $0.7 \times 10^6$ chondrocytes were loaded onto each scaffold separately. After allowing an additional 1 hour for cell attachment, seeded constructs were cultured in 1 mL of chemically defined medium (DMEM+ 10% FBS with 1×PSF, 0.1 µM dexamethasone, 50 µg/mL ascorbate 2-phosphate, 40 µg/mL L-proline, 100 µg/mL sodium pyruvate, 1×ITS+(6.25 µg/ml insulin, 6.25 µg/ml transferrin, 6.25 ng/ml selenous acid), 1.25 mg/ml Bovine Serum Albumin, and 5.35 µg/ml Linoleic Acid with 10 ng/mL TGF-β3 (R&D systems, Minneapolis, Minn.) in non-tissue culture treated 12-well plates.

Cell Seeding and Culture on Scaffold Layers: hMSCs.

To produce cell-seeded meniscal equivalent constructs, scaffolds were cultured with hMSCs and differentiated to chondrogenic phenotype mimicking native meniscal tissues (Buma et al., 2004 and Verdonk et al., 2005). To manage the cell numbers needed, instead of crescent meniscus shape, the scaffolds were cut into discs (5 mm in diameter and 2 mm in thickness). For cell seeding, the scaffolds were disinfected, washed in sterile PBS and conditioned with growth medium for overnight. To monitor response of different meniscus layers in terms of ECM deposition and cell proliferation, hMSCs were seeded in each scaffold layer. 20 µl aliquots containing $0.8 \times 10^6$ hMSCs were loaded onto each scaffold layer separately. After allowing an additional 2 hours for cell attachment, seeded constructs were cultured in 1 mL of growth medium for the next 3 days to allow cells attach and spread on to scaffold pores. Following attachment, scaffolds with cells were transferred to chemically defined medium chondrogenic medium containing (DMEM+10% FBS with 1×PSF, 0.1 µM dexamethasone, 50 µg/mL ascorbate 2-phosphate, 40 µg/mL L-proline, 100 µg/mL sodium pyruvate, 1×ITS+(6.25 µg/ml Insulin, 6.25 µg/ml Transferrin, 6.25 ng/ml Selenous Acid), 1.25 mg/ml Bovine Serum Albumin, and 5.35 µg/ml Linoleic Acid with 10 ng/mL TGF-β3 (R&D systems) in non-tissue culture treated 12-well plates. This chemically defined media formulation was used as it has previously been reported to both induce as well as maintain chondrogenesis of hMSCs and to promote deposition of fibrocartilaginous ECM (Baker and Mauck, 2007). Media with supplements was changed every 3 days over a 4-week period.

Real Time PCR.

For total RNA extraction, hMSCs cultured within silk-fibroin 3D scaffolds under chondrogenic conditions for 14 and 28 days were placed on ice, and were cut into small pieces using sharp dissection scissors. The cut pieces were transferred into 2-ml plastic tubes containing 1.5 ml of Trizol solution (Invitrogen, USA). After a brief incubation of 15 minutes, the treated scaffolds were centrifuged at 12000 g for 10 min at 4° C. The supernatant was transferred to a new tube and 200 µl of chloroform was added. After further incubation for 5 minutes at room temperature, the solution was gently mixed for 15 seconds, followed by another incubation for 5 minutes at room temperature. The tubes were then centrifuged for 15 minutes at 12000 g at 4° C. The upper aqueous layer was transferred to an RNeasy Plus mini-spin column (Qiagen, Germany). The RNA was washed and eluted according to the manufacturer's protocol. RNA samples were reverse-transcribed into cDNA using High capacity cDNA reverse transcription kit (Applied Biosystems, USA) according to the manufacturer's protocol.

Real-time PCR conditions were optimized and were performed with SYBR Green (Applied Biosystems, USA) in an ABI Prism® 7000 Sequence Detection System (Applied Biosystems, USA). For real time analysis, SYBR Green supermix, 5 µl of each forward and reverse primers and 5 µl cDNA template were used in a final reaction volume of 50 µl and plates were loaded using a RT loading platform. Cycling conditions included an initial denaturation step of 8 min and 45 s at 95° C., followed by 45 cycles of 30 s at 95° C., 30 s at 58° C., and 30 s at 72° C. Data collection was enabled at 72° C. in each cycle. CT (threshold cycle) values were calculated using the Relative Quantification software (Applied Biosystems). Highly purified gene-specific primers for collagen-1-alpha-1 (COL1A1_NM_000088.3), Aggrecan (ACAN_NM_0 13227.3), collagen-10-alpha-1 (COL10A1_NM_000493.3), SOX9 (NM_000346.3) and housekeeping gene GAPDH (NM_002046.3) were ordered commercially (Applied Biosystems, USA). Relative expression levels for each target gene was normalized by the Ct value of the house keeping GAPDH gene using an identical procedure ($2^{-\Delta\Delta Ct}$ formula, Perkin Elmer User Bulletin #2).

Biochemical Assays for DNA, GAG and Collagen Content.

Silk meniscal scaffold samples (with and without cells) were digested for 16 hrs with papain digestion cocktail (125 µg/ml papain, 5 mM L-cystein, 100 mM $Na_2HPO_4$, 5 mM EDTA, pH 6.2) at 60° C. for DNA and glycosaminoglycans (GAG) estimation. DNA content was measured using PicoGreen DNA assay kit as per manufacturers' protocol (Invitrogen, Carlsbad, Calif.). In brief, the papain digested samples were centrifuged and 25 µl aliquot of supernatant from each sample was added into a 96 well plate with wells containing 75 µl of 1×TE buffer. 100 µl of Quant-iT PicoGreen reagent (1:200 dilution) was added to each well followed by measurement using a fluorimeter with an excitation and emission wavelength of 480 and 528 nm respectively. A standard curve was generated using lambda phage DNA for quantitation. Total sGAG was estimated using 1,9-dimethyl-methylene blue (DMMB) assay (Whitley et al., 1989). Individual sample aliquots were mixed with DMMB reagent and absorbance measured at 525 nm wavelength. For estimation of sGAG secreted into media, spent culture media was stored at −20° C. and later assessed for sGAG content using similar protocols. GAG was estimated using a standard curve generated using shark chondroitin sulfate (Sigma, St Luis, Mo.). For total collagen estimation, the samples were digested in pepsin cocktail (1 mg/ml pepsin, pH 3.0) at 4° C. for 48 hrs. The collagen content was measured using modified Hride Tullberg-Reinert method (Tullberg-Reinert et al., 1999). In brief, individual digested samples were dried at 37° C. in 96-well plate for 24 hrs and reacted with Sirius red dye solution for 1 hr with mild shaking. The dye solution (pH, 3.5) was prepared with Sirius red dissolved in picric acid-saturated solution (1.3%; Sigma, St Luis, Mo.) to a final concentration of 1 mg/mL. The samples were washed five times with 0.01 N HCL followed by resolving dye-sample complex using 0.1 N NaOH and recording absorbance at 550 nm. Total collagen was estimated using a standard curve using bovine collagen (Sigma, St Luis, Mo.). Scaffolds without cells were taken as Blank and values subtracted in all assays to negate interference. To avoid variations from scaffold sizes and cell numbers, GAG and collagen contents were normalized against total scaffold weight and cell numbers, represented by the total DNA content measured by PicoGreen DNA assay kit (Invitrogen).

Histology and Immunocytochemistry of Constructs.

Individual scaffold layers seeded with cells were washed in PBS followed by fixation in 10% neutral buffered formalin for 24 hrs before histological analysis. Samples were dehydrated through a series of graded ethanol, embedded in paraffin and sectioned at 5 µm thickness. For histological evaluation, sections were deparaffinized, rehydrated through a series of graded ethanol, and stained. Serial sections were stained with Hematoxylin and Eosin (H&E) as well as with Safranin-O and Alcian blue for sulfated proteoglycans in the matrix. Similarly, representative constructs were immunostained with monoclonal antibodies against collagen I and II (Abcam, MA). Immunohistochemical sections were deparaffinized, hydrated, and permeabilized. The sections were then incubated for 30 min with 1% bovine serum albumin at 37° C. followed by primary antibody for 2 hrs. The sections were washed and incubated with HRP-labeled secondary antibodies (Santa Cruz) followed by standardized development in diaminobenzidine (DAB) (Vector Laboratories, CA). The sections were counterstained with hematoxylin.

Confocal Microscopy: Fibroblasts and Chondrocytes.

Fibroblast and chondrocyte cell attachment and spreading on individual *B. mori* silk fibroin scaffold layers was assessed using confocal microscopy. For microscopy, each individual scaffold layer was seeded with $1 \times 10^6$ and $0.7 \times 10^6$ human primary fibroblast and human primary chondrocytes separately, and cultured for 1 and 28 days at 37° C., 5% CO2 in medium as mentioned above to allow cells to adhere and spread on the matrix. On harvesting day, scaffolds were washed three times with PBS (pH 7.4) followed by incubation in 3.7% formaldehyde in PBS for 10 min. The samples were further washed with PBS and pre-incubated with 1% bovine serum albumin (BSA) for 30 min. The constructs were then permeabilized using 0.1% Triton X-100 for 5 min. Incubation with Rhodamine-Phalloidin for 20 min at room temperature followed by PBS washing and counterstaining with Hoechst 33342 for 30 min was performed. Images from stained constructs were obtained using a confocal laser scanning microscope (CLSM, Leica SP2 inverted microscope, Mannheim, Germany) equipped with argon (488 nm) and HeNe (534 nm) lasers; two-dimensional multichannel-image processing was performed using IMARIS software (Bitplane AG, Switzerland). Several microphotographs were taken of different samples and analyzed. Figures disclosed herein show one representative sample per group.

Confocal Microscopy: hMSC and Silk Fibroin Scaffold.

hMSC attachment and spreading on individual *B. mori* silk fibroin scaffold layers after each time point was assessed using confocal microscopy. For microscopy, each individual scaffold layer was seeded with 0.8×10⁶ hMSCs, and cultured for 1 day, 14 days, 21 days and 28 days at 37° C., 5% $CO_2$ in chondrogenic medium as mentioned above to allow cells to adhere and spread on the matrix. On the day of harvest, scaffolds were washed three times with PBS (pH 7.4) followed by incubation in 3.7% formaldehyde in PBS for 10 min. The samples were further washed with PBS and pre-incubated with 1% bovine serum albumin (BSA) for 30 min. The constructs were then permeabilized using 0.1% Triton X-100 for 5 min. Incubation with Rhodamine-Phalloidin for 20 min at room temperature followed by PBS washing and counterstaining with Hoechst 33342 for 30 min was performed. Images from stained constructs were obtained using a confocal laser scanning microscope (CLSM, Leica SP2 inverted microscope, Mannheim, Germany) equipped with argon (488 nm) and HeNe (534 nm) lasers; two-dimensional multichannel-image processing was performed using IMARIS software (Bitplane AG, Switzerland). Several microphotographs were taken of different samples and analyzed. Figures show one representative sample per group.

Mechanical Testing of Constructs.

Mechanical characterization of compressive and tensile properties of hydrated scaffolds was determined on an Instron (Norwood, Mass.) 3366 testing frame equipped with a 0.1 kN load cell. The tests for hydrated scaffolds were carried out in 0.1 (M) PBS at 37° C. The scaffolds were hydrated at least 1 day before tests. To test compressive property, silk scaffolds punched out in 4 mm diameter and 3 mm height discs. All tests were accessed with a conventional open-sided (non-confined) configuration and were performed using a displacement control mode at a rate of 5 mm/min. After the compression tests, the compressive stress and strain were graphed based on the measured cross-sectional area and sample height (nominal ~4-5 mm, measured automatically at 0.02N tare load), respectively. On the other hand, the tensile properties of the silk scaffolds (approximately, 20 mm×5 mm×1 mm) were measured with a crosshead speed of 0.1% strain $s^{-1}$ and a nominal tare load of 0.02 N applied at 0.3% strain. The dimension of the wet specimens was measured before test. Gauge length was set 14 mm. The yield strength and the compressive modulus were determined from the compressive curves. Also, the tensile strength, modulus, and strain were obtained from the tensile curves. The elastic modulus was calculated based on a linear regression fitting of a small strain section that precedes an identifiable plateau region in both tests. From the compressive curves, the compressive yield strength was determined using an offset-yield approach. A line was drawn parallel to the modulus line, but offset by 0.5% of the initial sample gauge length. The corresponding stress value at which the offset line crossed the stress-strain curve was defined as the compressive yield strength of the scaffold, and is an estimate of the linear elastic and collapse plateau transition point. From the tensile curves, tensile strain (elongation %) was determined as extension normalized to gauge length and ultimate tensile strength was verified as stress where specimen was broken.

Statistical Analysis.

All quantitative experiments are run at least in triplicate and results are expressed as mean±standard deviation for n=4 unless specified. Statistical analysis of data was performed by one-way analysis of variance (ANOVA). Differences between groups of $p \leq 0.05$ or $*p<0.05$ are considered statistically significant and $p \leq 0.01$ or $**p<0.01$ as highly significant.

Example 1

Gross Morphology and Stacking of Engineered Silk Meniscal Constructs

Native meniscus pore heterogeneity was mimicked within silk scaffolds as individual layers using an all aqueous method (FIG. 1). In some embodiments, the fabricated scaffold layers can be rigid and compact due to relatively high (9 wt %) silk content. Scanning electron microscopic (SEM) pictures revealed that the top two layers fabricated using salt leaching method had circular pores in the size range of about 350-about 400 and about 500-about 600 microns, respectively. The pores were highly interconnected with smaller pores. However, the bottom third layer fabricated using freeze-drying method showed laminar channels with pore width ranging between 60-80 microns. The fabricated scaffolds were shaped like native meniscus (wedge shaped) and three individual layers were stacked on top of each other to form a single unit mimicking meniscus multiporosity (FIG. 1). FIG. 2 demonstrates exemplary methods that can be adopted to merge these individual layers into one single unit for graft applications. In one embodiment, the method includes individually seeding cells in each of these silk fibroin layers, growing them under ambient conditions for cells to homogeneously distribute followed by stacking them before use.

Example 2

Cell Attachment and Proliferation on Individual Silk Scaffold Layers

Figure 9A:
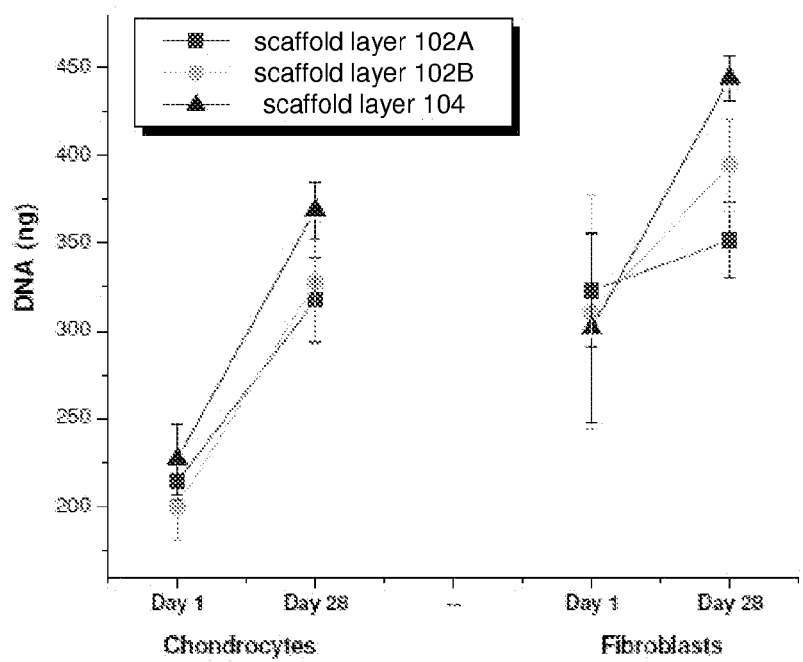
FIGS. 9A to 9D show biochemical assay results estimated in 3 scaffolds layers individually seeded with primary human chondrocytes and fibroblasts in chondrogenic medium after day 1 and 28.

Confocal microscopy was used to evaluate fibroblast and chondrocyte cell proliferation and attachment onto individual silk meniscus scaffold layers. At day 1, cells appeared clustered and attached onto walls of scaffolds in their early stage of seeding. Further, cell spreading was observed to be minimal at day 1 in both cases (fibroblasts and chondrocytes) as the scaffold pore lumens can be clearly seen (FIGS. 3A to 3I, 4A to 4C). In comparison, after day 28 of seeding and culture, the cells had filled the scaffold pore voids and spread out actin filaments. In all three meniscal scaffold layers the cells (fibroblast and chondrocytes) were evenly distributed and showed confluence (FIGS. 3A to 3I, 4D to 4F). Further, PicoGreen DNA assay results showed that the chondrocytes proliferated with an increase of approximately ~48%, ~64% and ~38% compared to initial cell numbers (day 28 vs. day 1) in the case of $1^{st}$, $2^{nd}$ and $3^{rd}$ layers, respectively. The fibroblasts showed nearly ~10%, ~27% and ~47% rise in cell numbers, respectively, for 1-3 layers after 28 days of culturing in chondrogenic media (FIG. 9A).

Example 3

Histology and Immunocytochemistry of Individual Meniscus Scaffold Layers

Figure 5A:
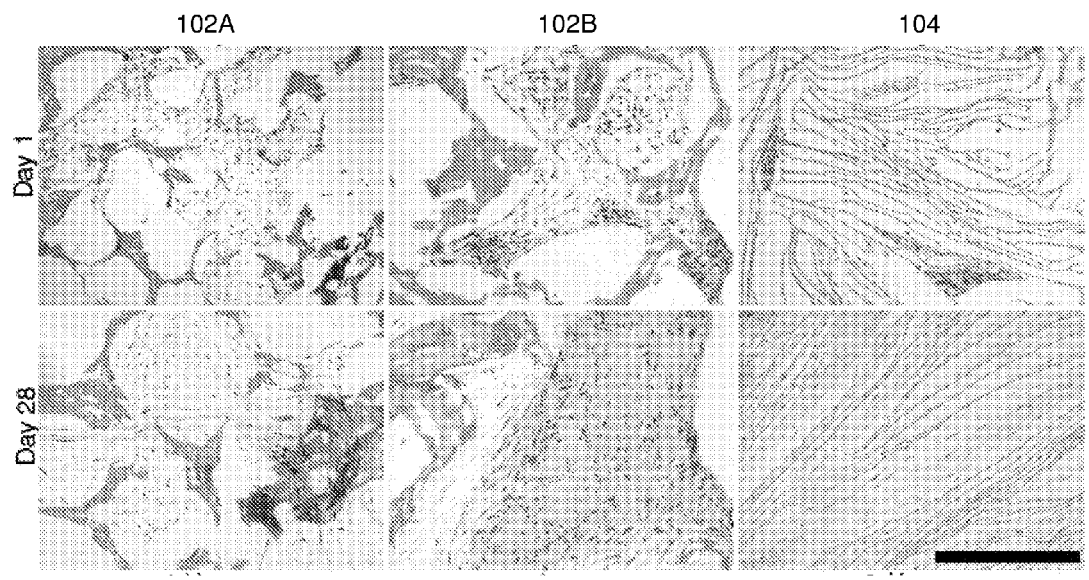
FIGS. 5A to 5C show histology sections showing primary human fibroblast cell growth and extracellular matrix (ECM) deposition on individual 3D silk meniscus scaffold layers in chondrogenic medium. Hematoxylin and eosin staining (FIG. 5A); Alician blue staining (FIG. 5B) and Saffranin O staining (FIG. 5C). Scale bar represents 300 microns.
Figure 5B:
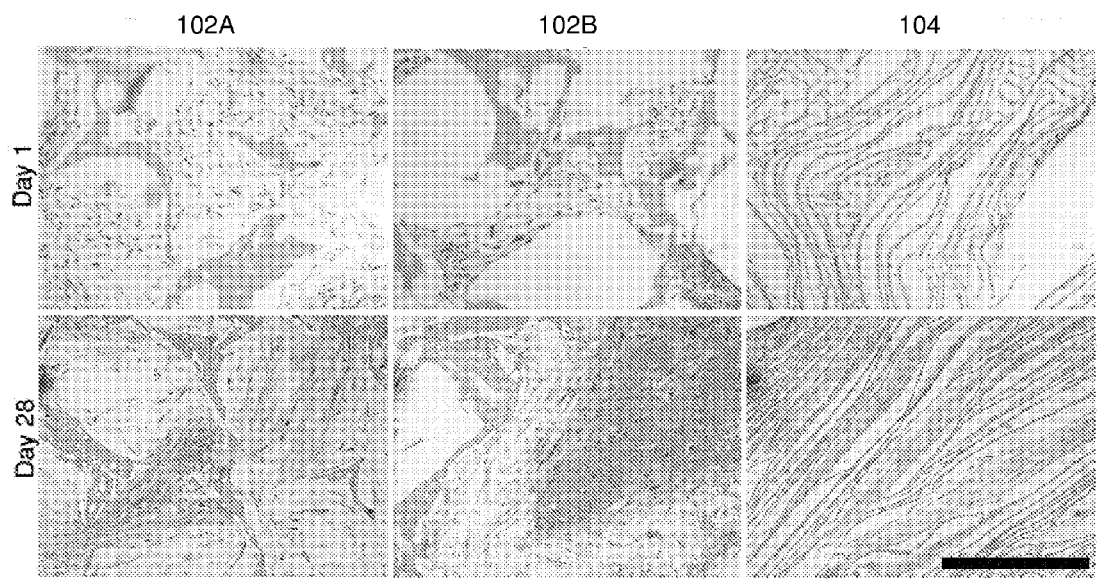
Figure 5C:
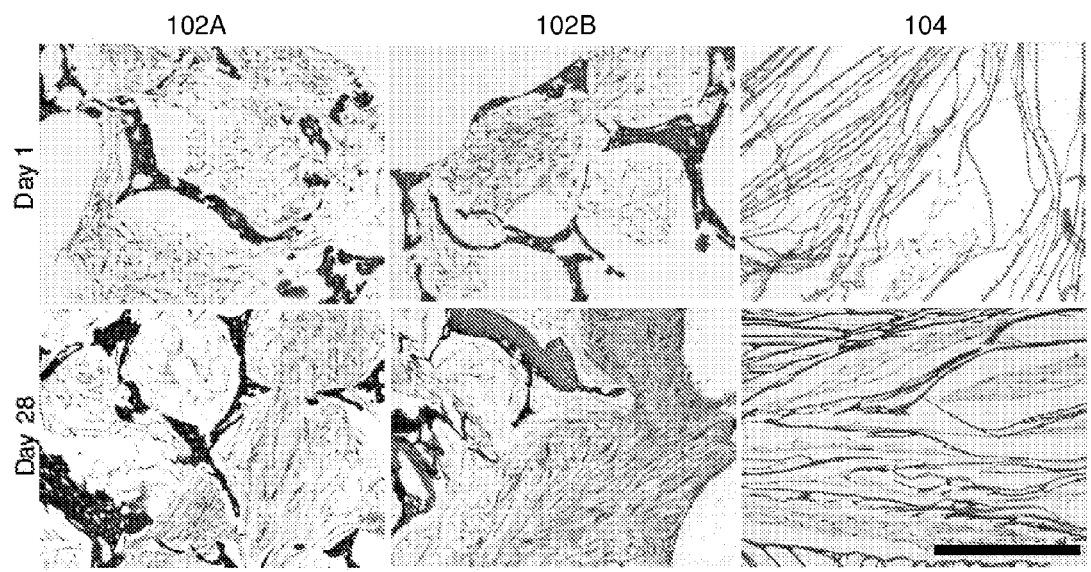
Figure 6A:
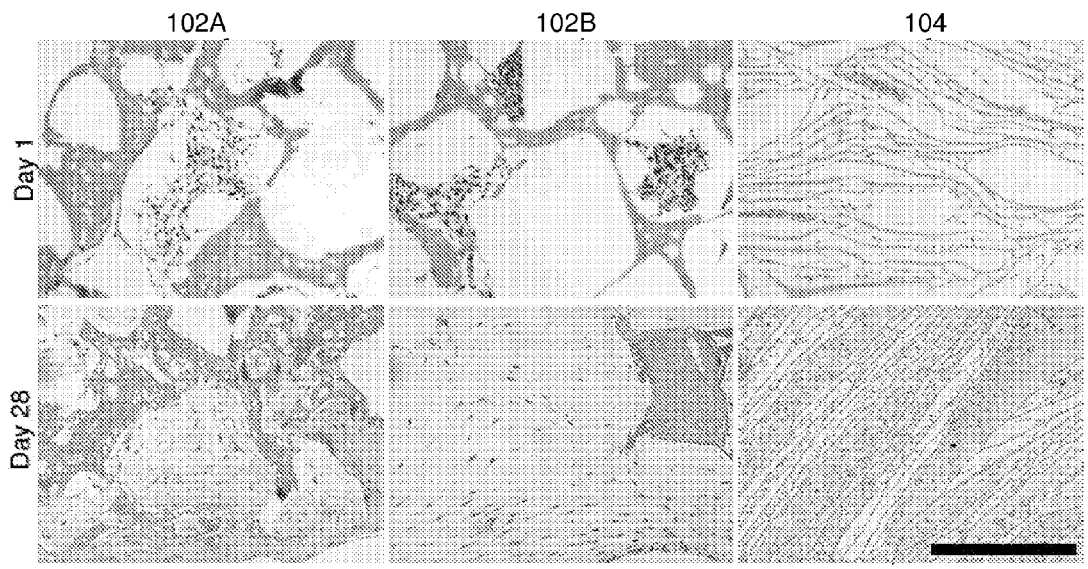
FIGS. 6A to 6C show histology sections showing primary human chondrocyte cell growth and ECM deposition on individual 3D silk meniscus scaffold layers in chondrogenic medium. Hematoxylin and eosin staining (FIG. 6A); Alician blue staining (FIG. 6B) and Saffranin O staining (FIG. 6C). Scale bar represents 300 microns.
Figure 6B:
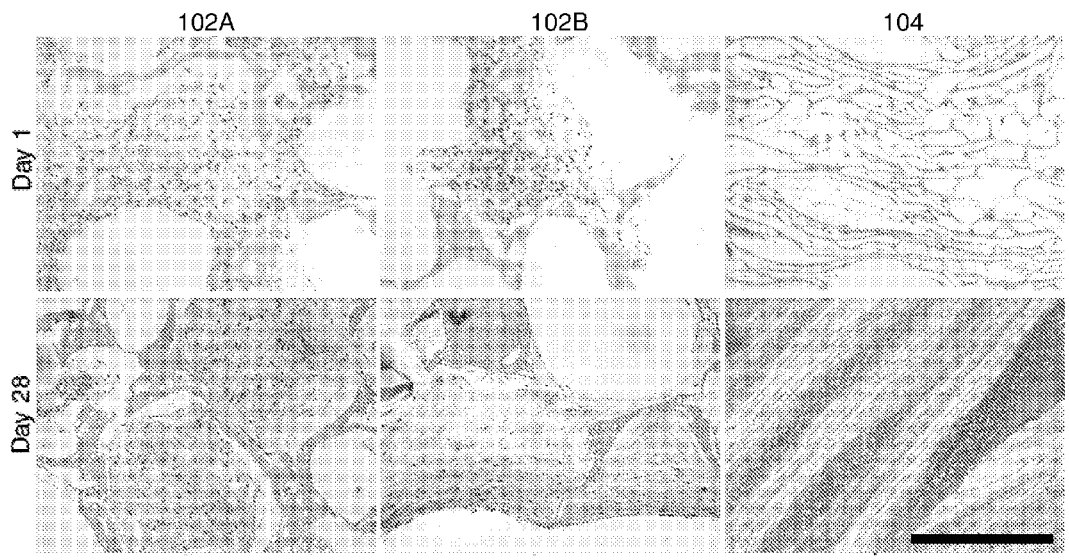
Figure 6C:
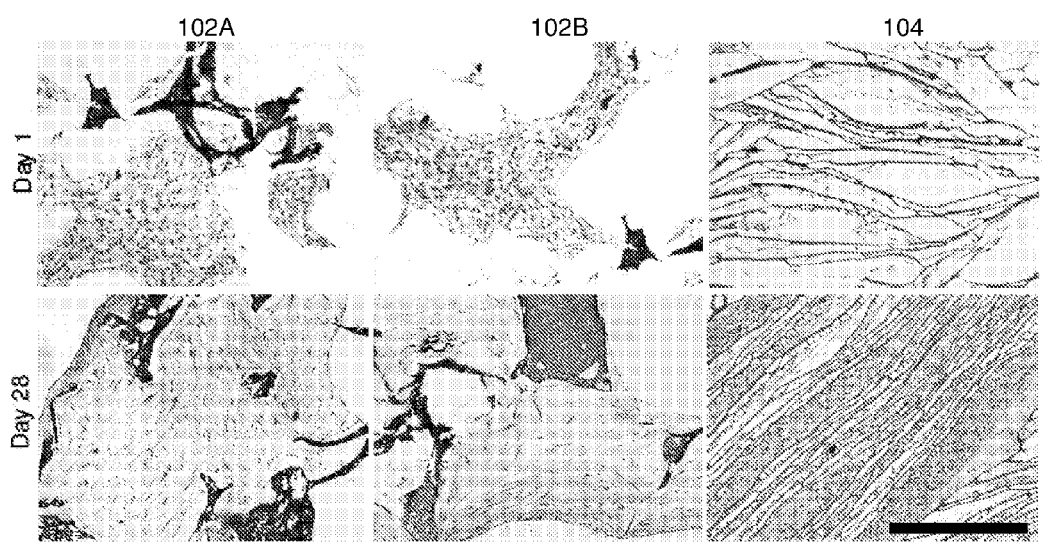

Histology sections of individual meniscus scaffold layers revealed accumulation of sGAG and collagen with time (day 28 vs day 1) in all three layers. Compared to day 1, samples for day 28 stained deeper and higher for Alician blue, Saffranin O and H & E in all three layers for both cell types (FIGS. 5A to 5C, 6A to 6C). For Alician blue, chondrocytes showed intense blue color indicating presence of abundant sGAG. Particularly for the laminar $3^{rd}$ scaffold layer, the cells stained intense deep blue indicating matured chondrocyte phenotype (FIGS. 6B, 8). For fibroblast, the staining was lighter compared to chondrocytes, but showed positive blue color on culturing in chondrogenic medium (FIGS. 5B, 8). Similarly, Saffranin O staining confirmed GAG accumulation within scaffold pores in all layers. In case of Saffranin O staining, faint positive staining of fibroblast cells was observed compared to intense staining of chondrocytes (FIG. 5C). H & E staining revealed cell attachment and distribution within each scaffold pore/layer indicating growth and proliferation (FIGS. 5A to 5C, 6A to 6C). In some embodiments, cells were not confluent and appeared scattered onto scaffold pores on day 1, but later became confluent and completely filled the void spaces upon prolonged culturing on day 28.

Figure 7A:
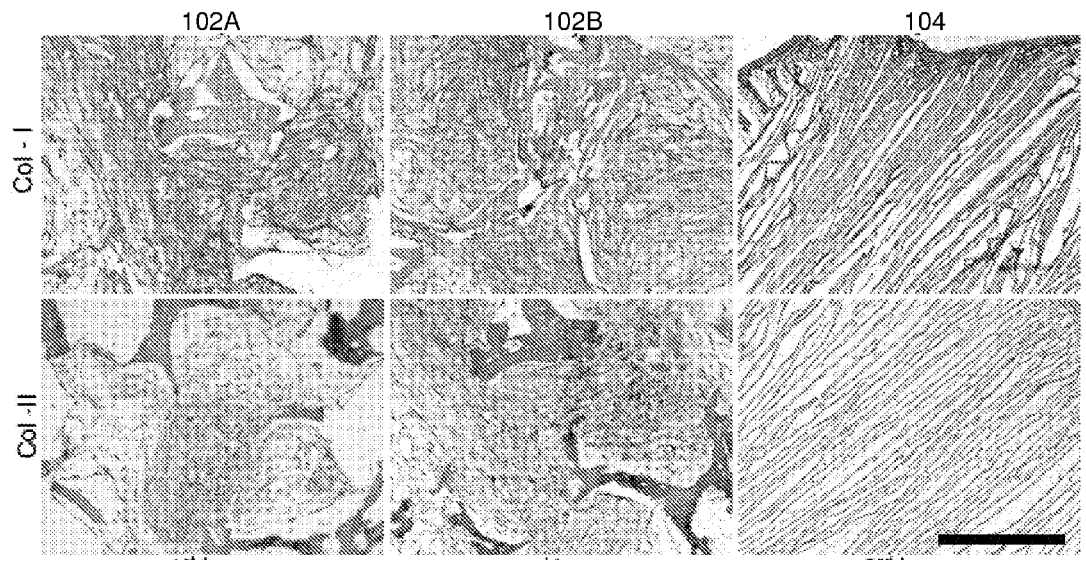
FIGS. 7A and 7B show silk fibroin scaffold histology sections showing immunostaining for collagen I and II. Fibroblast cells (FIG. 7A) and chondrocytes (FIG. 7B) cultured on different scaffold layers cultured for 28 days using chondrogenic medium. Scale bar represents 300 microns.
Figure 7B:
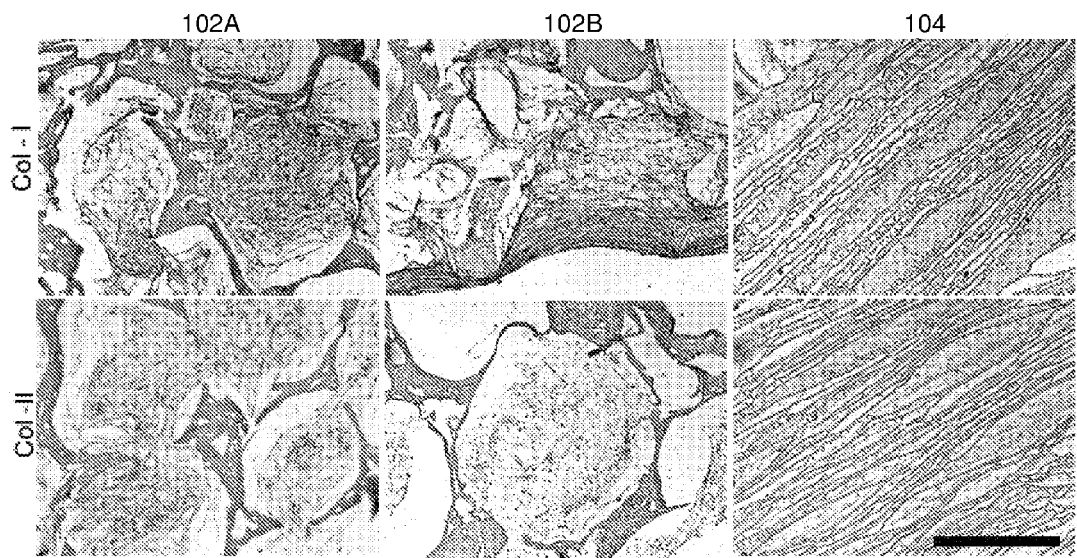

Immunocytochemistry staining revealed deposition of collagen I and II within scaffold layers. For both fibroblast and chondrocytes, collagen I deposition was abundant on day 28 (FIGS. 7A and 7B). For collagen II deposition, fibroblasts stained almost negative when compared to the chondrocytes showing higher depositions (FIGS. 7A and 7B). In all scaffold layers, the collagen depositions were homogenously distributed with complete filling of the pores.

Example 4

Biochemical Analysis of Individual Meniscus Scaffold Layers

Figure 9B:
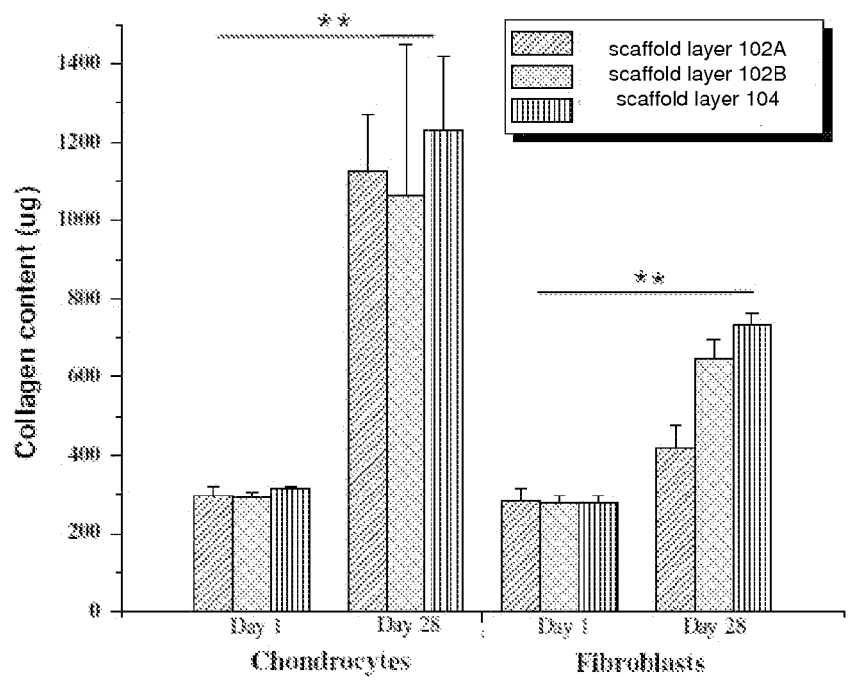
Figure 9C:
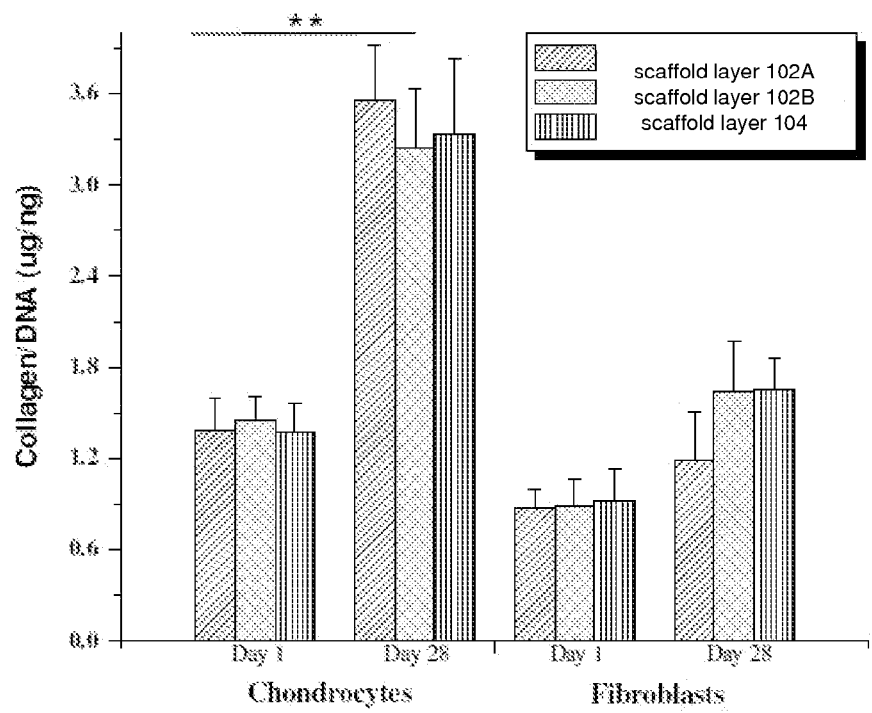

Histology and immunocytochemistry data was supported by biochemical analysis data indicating the presence of a mature chondrocytic phenotype within the scaffold layers. Both collagen and sGAG amount increased with time ($p \leq 0.01$) (day 28 vs day 1) (FIGS. 9A-9D, 10A-10D). Total collagen amount in chondrocytes increased approximately ~280%, ~266% and ~294% in $1^{st}$-$3^{rd}$ scaffold layers, respectively, when compared to day 1 ($p \leq 0.01$) (FIG. 9B). This was higher in comparison to fibroblasts which showed approximately ~47%, ~135% and ~164% increase in total collagen amount in all three layers, respectively, at the same time ($p \leq 0.01$) (FIG. 9B). The total amount of sGAG (scaffold+media) increased approximately by ~209%, ~207% and ~330% for chondrocytes when compared to ~180%, ~230% and ~160%, respectively, for fibroblasts for $1^{st}$-$3^{rd}$ layer (FIG. 10A). However, the total amount of sGAG deposited was comparatively much lower in fibroblast cells (40 μg-100 μg) as compared to chondrocytes (5 μg-33 μg) after 28 days of culturing ($p \leq 0.01$) (FIG. 10A). Substantial amount (~30-40%) of total detected sGAG was secreted into the medium while culturing these chondrocytes in chondrogenic medium (FIGS. 10A, 10D).

Figure 10A:
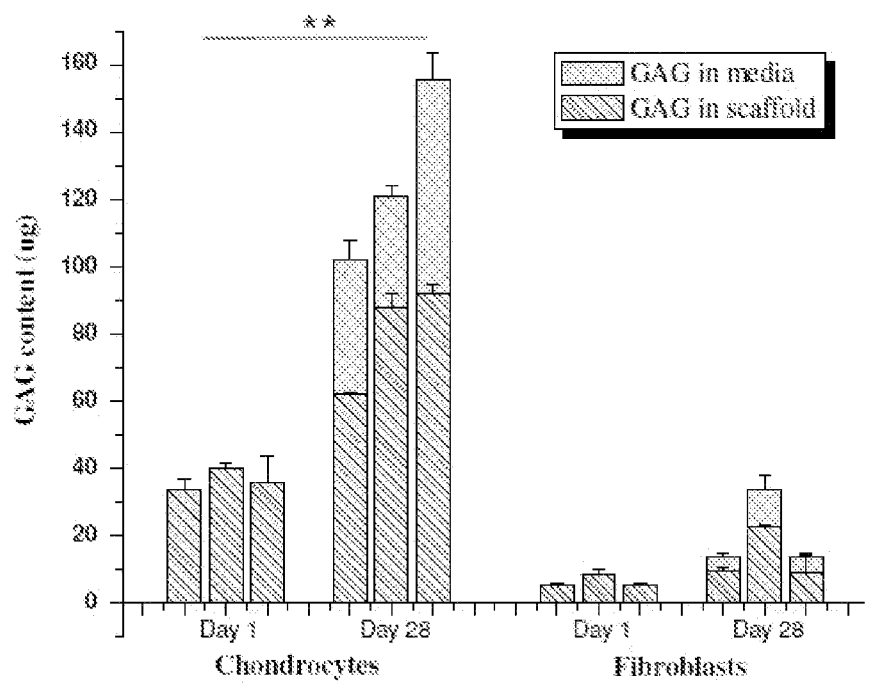
FIGS. 10A to 10D show biochemical assay results estimated in 3 scaffold layers individually seeded with primary human chondrocytes and fibroblasts in chondrogenic medium after day 1 and 28.
Figure 10B:
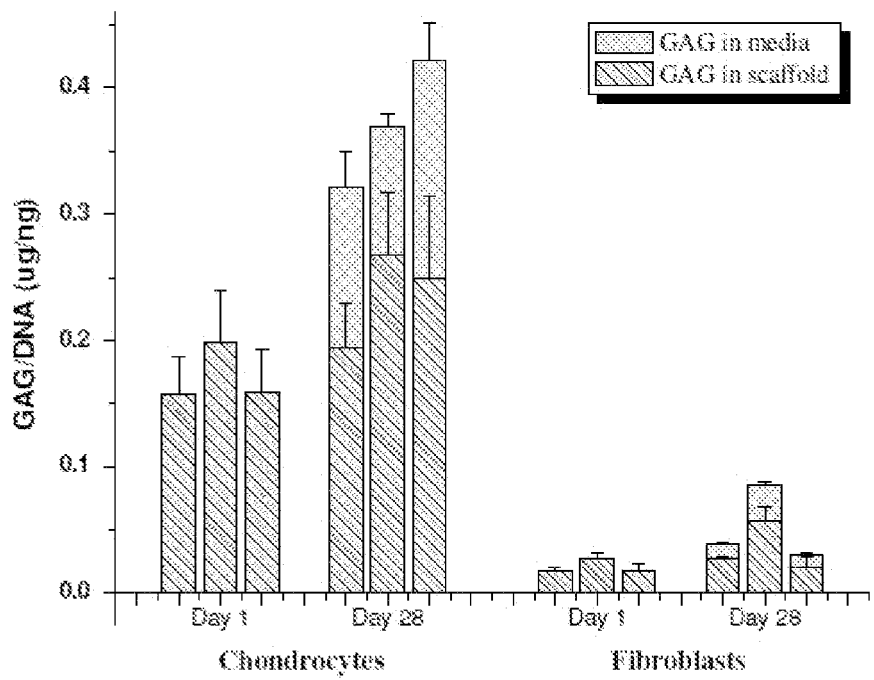

To minimize discrepancy from cell numbers due to cell seeding difference within the three scaffold layer groups and cell types, total collagen content was presented by normalizing it with DNA amount from the same day. The normalized collagen per unit DNA content increased ~1.5 fold in case of chondrocytes in all layers when compared to ~0.5 fold for fibroblasts, respectively, though the relative amount was much lesser in fibroblasts after day 28 ($p \leq 0.01$) (FIG. 9C). Similarly, total sGAG per unit DNA (present in media and deposited in scaffolds) after 28 days of culturing, increased by ~2.1 fold in case of chondrocytes when compared to ~0.3 fold for fibroblast cells ($p \leq 0.01$) (FIG. 10B). Compared to deposited sGAG within scaffolds, secreted GAG was ~30-40% of the total amount in all three silk layers (FIGS. 10A, 10B). To assess sGAG production profiles by these cells, sGAG content was estimated in chondrogenic medium from each layer and each cell type for 28 days (FIG. 10D). Chondrocyte cells reached maximum sGAG production within the first 2 weeks and after this time the amounts were constant. This trend was observed for all three silk meniscus layers. However, for fibroblasts, the amount was lesser.

Figure 9D:
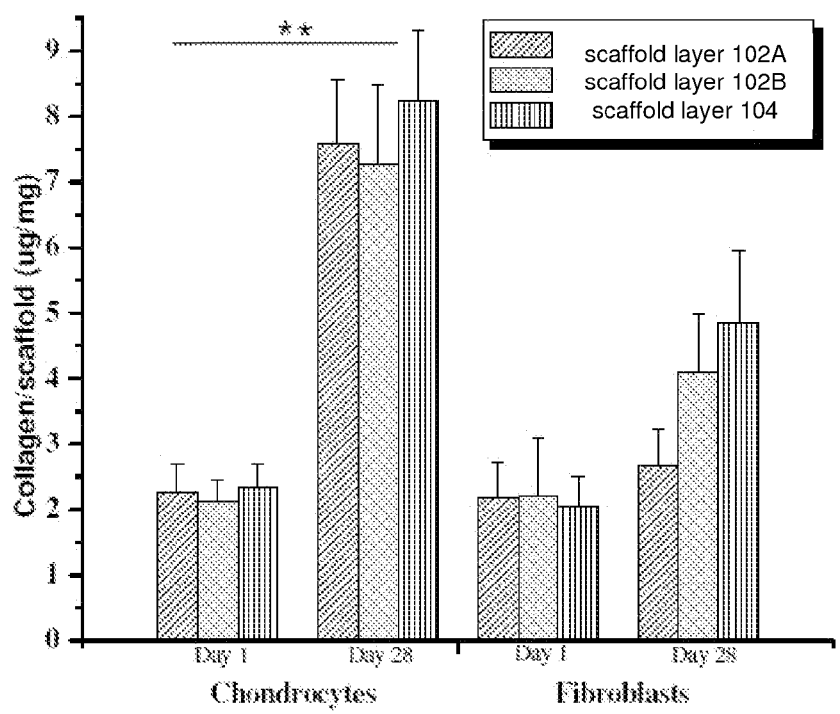
Figure 10C:
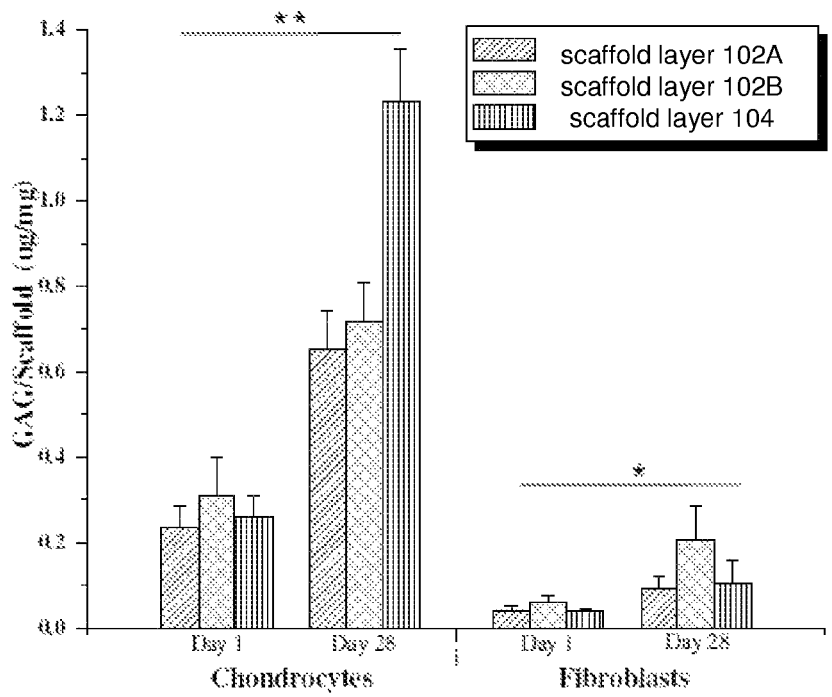
Figure 10D:
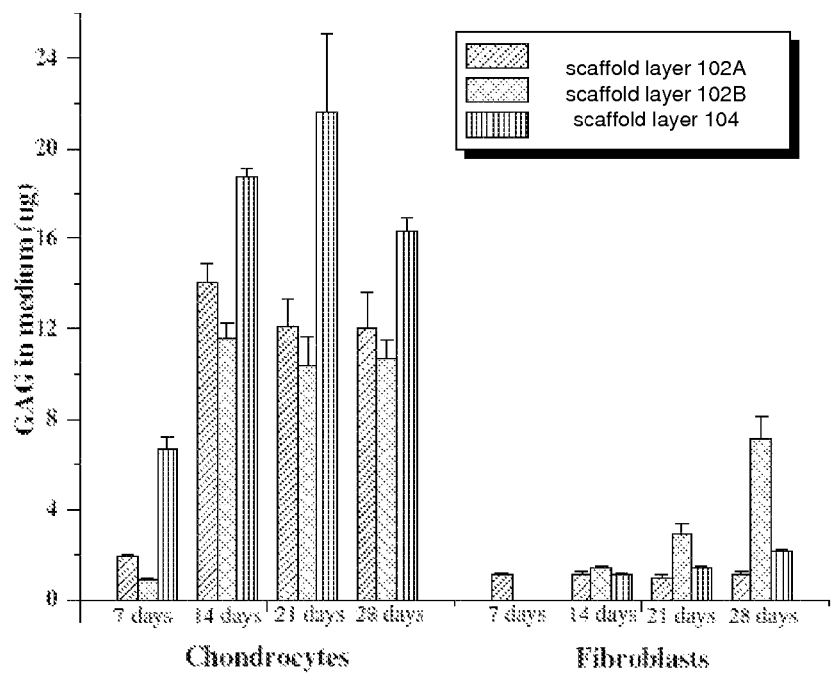

To assess the effect of different silk layer morphology and matrix features on ECM deposition, total collagen and sGAG amount was normalized as per unit scaffold mass (FIG. 9D, 10C). Collagen amount was independent of the layer morphology resulting in similar collagen deposition at day 28 (FIGS. 9B, 9C, and 9D). There was ~3.5 fold increase of the collagen amount per unit mass of silk fibroin scaffold in case of chondrocytes while ~1.5 fold increase in fibroblasts (day 28 vs day 1) ($p \leq 0.01$) (FIG. 9D). However, in the case of sGAG, an increase in GAG amount (~4.6 fold) was observed for the $3^{rd}$ layer with laminar morphology seeded with chondrocytes when compared to the first two circular porous layers (~2.5 fold) after day 28 (FIG. 10C).

Example 5

Mechanical Evaluation of Silk Meniscus Layers

Mechanical evaluation in terms of both compressive and tensile properties was carried for all three individual silk layers to assess its utility in mimicking natural meniscus tissue. The compressive modulus ranged between 293.78±47.56 kPa, 347.58±62.39 kPa and 164.80±14.24 kPa for 350 μm-400 μm ($1^{st}$), 500 μm-600 μm ($2^{nd}$) and 60 μm-80 μm ($3^{rd}$) scaffolds layers respectively (Table 1). Similarly, compressive strength was 67.23±27.30 kPa, 75.62±15.76 kPa and 70.44±09.07 kPa, respectively, for the $1^{st}$-$3^{rd}$ scaffold layers. Following tensile testing, both the $1^{st}$ and $2^{nd}$ layers were similar in terms of modulus with values approximately in the range of 1.3 MPa with elongation of 40% (Table 1). In comparison, the bottom 3rd layer showed lower values, ~0.26 MPa for tensile modulus, with elongation % observed to be much higher at 90% when compared to the first two silk fibroin layers.

TABLE 1

Mechanical properties of individual silk fibroin scaffold layers

| Silk scaffold layer | Tensile Modulus (MPa) | % Elongation | Compressive Modulus (kPa) | Compressive Strength (kPa) |
|---|---|---|---|---|
| 350-500 ($1^{st}$ layer) | 1.30 ± 0.29 | 42.56 ± 06.91 | 293.78 ± 47.56 | 67.23 ± 27.30 |
| 500-600 ($2^{nd}$ layer) | 1.41 ± 0.41 | 39.90 ± 07.59 | 347.58 ± 62.39 | 75.62 ± 15.76 |
| 60-80 ($3^{rd}$ layer) | 0.26 ± 0.08 | 90.62 ± 21.59 | 164.80 ± 14.24 | 70.44 ± 09.07 |

The success of a cell-based, polymeric tissue engineered meniscus graft model relies mainly on its ability to function as a single 3D support matrix mimicking its native structure to help graft integration, support cell growth and function to produce tissue-specific ECM matrix (Temenoff and Mikos, 2000, Coutts et al., 2001). Currently, the only available clinical option for total meniscus replacement was the use of an allograft meniscus. However, due to drawbacks related to the use of allogenic material, including shape incongruency, disease transmission and a limited availability of donor menisci, current meniscus research efforts focus on tissue engineering of the lost/defective part using different cell-sources, growth-factors, scaffolds or a combination thereof (Baker and Mauck, 2007; Baker et al., 2009; Mauck et al., 2007, Angele et al., 2007). A better understanding of the native meniscus tissue morphology, form and function has helped design optimum culture conditions for meniscus cell growth and differentiation. However, recapitulating the native meniscus tribiology structure and function in an in vitro tissue engineered model has been challenging (Fairbank, 1948; Petersen and Tillmann, 1998; Sweigart and Athanasiou, 2001; Proctor et al., 1989; Buma et al., 2004). In accordance with one or more embodiments of the invention, described herein is fabrication of 3D multiporous, multilamellar tissue engineered meniscus, mimicking native meniscus tribiology structure for future graft applications (Petersen and Tillmann, 1998).

To construct a viable tissue engineered meniscal construct mimicking native tissue, primary human cells were selected as the cell source and *Bombyx mori* cocoon silk as the biopolymer (due to its well reported unique mechanical properties, excellent biocompatibility, cell-controlled degradability and versatile processability along with its applications in biomedical fields (Altman et al., 2002, 2003; Zhang et al., 2009; Hofmann et al., 2006; Wang et al., 2005, 2006 a, b; Meinel et al., 2004 a, b). Peterson and Tillmann et al. (1998) has indicated that meniscus has a heterogeneous tribiology layered structure. Accordingly, three individual silk scaffolds layers of different porosities and pore orientations were fabricated. The first (top) and second (middle) silk meniscus layer, each of 2 mm thick fabricated using salt leached method, represents the heterogeneous pore distribution within a native meniscus having pores of ~350 microns-~400 microns and ~500 microns-~600 microns, respectively (FIG. 1). The meniscus model of Peterson and Tillmann indicates very fine mesh-like pores on the upper layers which are smaller than the top silk fibroin layer described herein (Petersen and Tillmann, 1998). Next, it was sought to determine whether, with seeded cells grown over time in the presence of growth factors, native ECM can be deposited on top and within these bigger pores, forming a fine porous mesh similar to native tissue (FIGS. 1, 3A-3I, 4A-4I). Further, the fabricated porous silk layers (with bigger pores) can aid in cell migration and finally forming a gradient of ECM mesh sizes by virtue of their different pore sizes, mimicking native tissue architecture over time. In addition, being the backbone and having high mechanical properties, silk fibroin layers can contribute high mechanical strength to the construct, resisting in vivo shear forces in future implantations (Altman et al., 2003). The fabrication method described herein is in contrast to reported spinning mesh fiber forming methods for meniscus engineering recapitulating native meniscus top mesh network (Baker and Mauck, 2007; Baker et al., 2009). The fabrication method of using initial bigger pores described herein have further allowed optimum nutrient passage throughout the construct, which can be essential for cell growth and survival after initial cell seeding. A very fine mesh-like network can be detrimental for cell survival and migration if created from day 0, hindering nutrient passage. Further, the third (bottom) silk layer with laminar channels of ~60 microns-~80 microns was fabricated to act as a template to allow seeded cells to grow, proliferate and align within these channels (FIG. 1). In some embodiments, the laminar channels acting as a template can aid aligning deposited collagen and other ECM in a laminar morphology similar to that of the native meniscus mimicking the aligned collagen bundles in laminar orientation contributing to high intrinsic tensile and compressive properties (Sweigart and Athanasiou, 2001; Tissakht and Ahmed, 1995; Petersen and Tillmann, 1998). The confocal images showed that cells (both fibroblast and chondrocytes) formed a mesh like network within pores and aligned structures within linear laminas (FIGS. 3A-3I, 4A-4I). Cells deposited their ECM (mainly collagen and GAG) over time, mimicking native tissue morphology and arrangement (mesh and laminar), as further confirmed by histology sections (FIGS. 5A-5C, 6A-6C, 7A-7B).

In addition to regeneration of native meniscus tribiology structure, mimicking its fibrocartilaginous cellular phenotype was also important to engineer a functional meniscus graft. To recapitulating native meniscus fibrocartilaginous structure and the spatially separated cellular phenotype, primary human fibroblasts were seeded as concentric rings on the outside to recreate the vascular fibrous region, while chondrocytes were seeded in the inner concentric zone to represent the avascular cartilage (McDevitt and Webber, 1990; Ghadially et al., 1983; O'Connor, 1976; Petersen and Tillmann, 1998). Fibroblast and chondrocytes were seeded individual in each scaffold layers and cultured for 28 days to evaluate cell proliferation, ECM production from each layer and cell type (FIG. 8). The confocal images showed that the cells (both fibroblast and chondrocytes) became confluent within the scaffold pores and laminas, and had good actin development throughout (FIGS. 3A-3I, 4A-4I). The individual silk fibroin layers supported cell proliferation with time based on the DNA content (FIG. 9A). However, fibroblasts showed half the proliferation (average DNA amount in all three layers) when compared to chondrocytes at day 28, possibly due to difference in initial cell seeding numbers at day 1 (FIG. 9A). Fibroblasts due to their higher initial cell seeding number became confluent early, inhibiting further cell proliferation and hence resulting in lower DNA values when compared to chondrocytes possibly having enough free surfaces to proliferate and grow. Intense staining to sGAG confirmed maintenance of chondrocytic phenotype and enhanced proteoglycans production with time within all individual layered silk structures (inner zone) (FIGS. 6B, 8). The importance of this result is further realized as the late passage cells (P8) were used for the experiment, indicating support of the matrix to maintain chondrocyte phenotype even for late passage cells. This is similar to native meniscus, where proteoglycans make for 2-3% of the dry weight and are mainly concentrated in the inner cartilaginous region of the meniscus (avascular zone) (Adams and Hukins, 1992; McDevitt and Webber, 1990; Buma et al., 2004). The bottom laminar meniscal layer showed more compact mature cartilage phenotype with intense alician blue and saffranin O staining when compared to the top and middle layers seeded with chondrocytes (FIG. 6B). This was possibly due to close proximity of cells growing in between laminar channels of narrow passage (60-80 microns) allowing more subcellular interactions when compared to cells in top and middle layers separated by pores of few hundred microns (FIGS. 3A-3I, 4A-4I). Importance of cellular interactions and proximity can further be realized on cell shape of growing chondrocytes, as they appear more elongated within the bigger pores but show a more compact polygonal morphology with presence of lacunae, similar to mature cells, within the 3rd (bottom) laminar layers (FIG. 8). Without wishing to be bound by theory, as the cells grow within bigger pores, they separated from each other (during initial seeding) and had to attach to the far pore walls ends, thus resulting in stretched morphology in contrast to cells within narrow passages and close proximity in the case of the third silk layer (FIGS. 3A-3I, 4A-4I). Based on the ECM content, the bottom laminar layer produced higher sGAG when compared to the other two top layers ($p<0.01$) (FIGS. 10A-10C). It was sought to determine whether initial cell seeding number and substratum size and morphology can impact chondrocyte morphology (Baker and Mauck, 2007;

Baker et al., 2009; Wang et al., 2006 b). However, based on the intense Alician blue, saffranin O staining and proteoglycan assay results, the chondrocytes maintained their phenotype with time, with sGAG (both deposited and secreted into medium) and collagen production in presence of chondrogenic medium with TGF-b3 (FIGS. 5A-5C, 6A-6C, 9A-9D, 10A-10D). Cultured primary fibroblasts showed positive results to sGAG (Alician blue and Saffranin O), though with low intensity staining, when compared to chondrocytes, possibly due to the presence of TGF-b in chondrogenic medium, which might have induced sGAG production (FIGS. 5B, 8).

Based on the biochemical assay results (FIG. 9B), increased total collagen amount further indicate maintenance of a growth microenvironment within the pores and lamina of all individual silk fibroin layers for the cells to grow and secrete ECM similar to native meniscus ($p<0.01$). Immunostaining results showed enhanced production of collagen I and II by cultured chondrocytes at day 28, within the inner (avascular) zone of all silk meniscus layers and analogous to the biochemical composition of the native meniscus tissue (FIGS. 7A and 7B) (Adams and Hukins, 1992). Further, an increase in type I collagen at day 28, along with type II collagen expression, reflects a reversal of any dedifferentiation events that might have occurred due to the higher passage number of the cells used, since P8 cells were used. In comparison, cultured fibroblasts showed positive for collagen I and negative for collagen II staining in the outer peripheral zone, a feature similar to previous studies on native meniscus (Cheung, 1987).

The meniscus is a load-bearing structure where mechanical properties are critical in order to withstand in vivo stresses. Without wishing to be bound by theory, possibly due to difference in pore wall thickness of constructs (within different layers), a marginally higher compressive modulus for second scaffold layer was observed as compared to the first layer while lowest values were observed in the case of the third layer (Table 1). Bigger pores having lower total pores per unit volume can result in thicker walls due to the same protein amount when compared to smaller pores. The silk meniscus layers described herein had higher compressive moduli when compared to the reported axial (83.4 kPa) and radial (76.1 kPa) compressive moduli for native human medial meniscus (Chia and Hull, 2008). Further, when compared with human medial meniscus at physiological strain rate, the silk constructs, in accordance with one or more embodiments of the invention, were nearly ⅓ for the first and second layer and ⅙ for the third layer, when compared to reported values of 718 kPa and 605 kPa, respectively, for axial and radial compressive moduli (Chia and Hull, 2008). Similarly, considering the anterior (1,048 kPa) and posterior (329 kPa) modulus values for native human meniscus, silk constructs provided herein as one or more embodiments showed values which were approximately ⅓ for top two layers and ⅙ for the bottom layer (Chia and Hull, 2008). Further analysis and compared with reported aggregate modulus values at the anterior (160±40 kPa) and posterior (100±30 kPa) of native human meniscus, the silk constructs according to one or more embodiments described herein showed higher values (Sweigart et al., 2004). Regarding tensile properties, values of approximately 1.3 MPa for the first two silk layers with 40% elongation was observed (Table 1). The third bottom layer showed lower values of 260 kPa, but higher elongation of 90% possibly due to its dense laminar morphology with thinner walls. However, the observed values were higher as compared to the previous (180 kPa-300 kPa) reported results using unseeded PLLA scaffolds (Gunja et al., 2009). It is believed that the final values is to be enhanced to match native meniscus tissue following cell seeding and ECM deposition on this layers as already observed and reported by others on constructs with and without cells (Baker and Mauck, 2007; Baker et al., 2009).

For transplantation and/or in vivo applications, graft integration is an important factor for success. In an effort to combine all three individual cell-seeded scaffold layers into one functional graft unit, three individual strategies can be adopted depending on situations. When grown in a composite stack, ECM developed after cell growth and migration within layers would help merge these layers into one single unit over time (a week or two depending on cell seeding density) (FIG. 2). However, to aid the process and hold the individual layers together, external stitching with silk threads can be considered, e.g., to prevent dislodging (FIG. 2). Further, in an attempt to quickly assemble these individual pieces into one functional unit, a rivet approach can also be considered, such as by using silk cylindrical pieces pushed into punched holes in the layers (FIG. 2). This method can help the entire construct to hold together. These stacking strategies can be used when instantaneous grafting with previously cell-laden or empty constructs is required.

Presented herein is a multi-layered silk fibroin scaffold that mimics native meniscus tissue structure and function. In some embodiments, the biomechanics of the construct can be modified in the presence of the cells and deposited ECM over time, e.g., in long-term culture. In some embodiments, other cell types including stem cells and meniscus fibrochondrocytes can be used in the silk fiborin scaffold as described herein. The multi-layered silk fibroin scaffold according to one or more embodiments as described herein can be evaluated in an in vivo model for functional outcome and integration.

The results presented herein demonstrate the fabrication of a wedge shaped multilamellar/multiporous silk meniscus scaffold with desirable mechanical properties and directed tissue growth. These individual layers supported robust cell growth (e.g., higher cellularization) with aligned ECM depositions and/or neo-tissue matrix reorganization. The inventors have demonstrated that colonizing fibroblast and chondrocytes in the silk fibroin scaffold or individual layer can form spatially separated ECM similar to native like tissues.

Example 6

Gross Morphology and hMSC Attachment on Silk Meniscus Layers

Figure 11A:
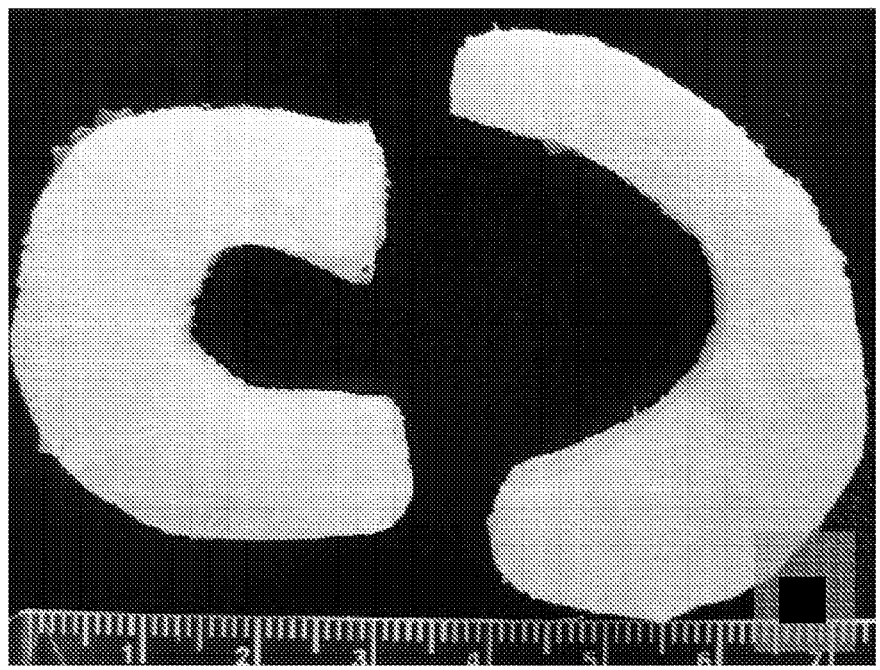
FIGS. 11A to 11D show images of regenerated silk scaffolds according to one embodiment of the invention for functional meniscus engineering.
Figure 11B:
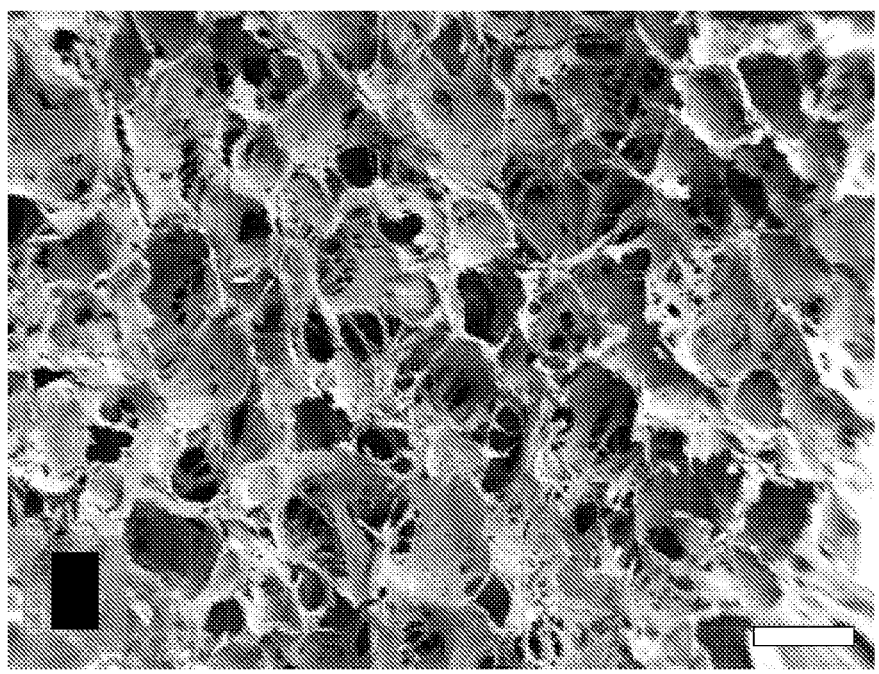
Figure 11C:
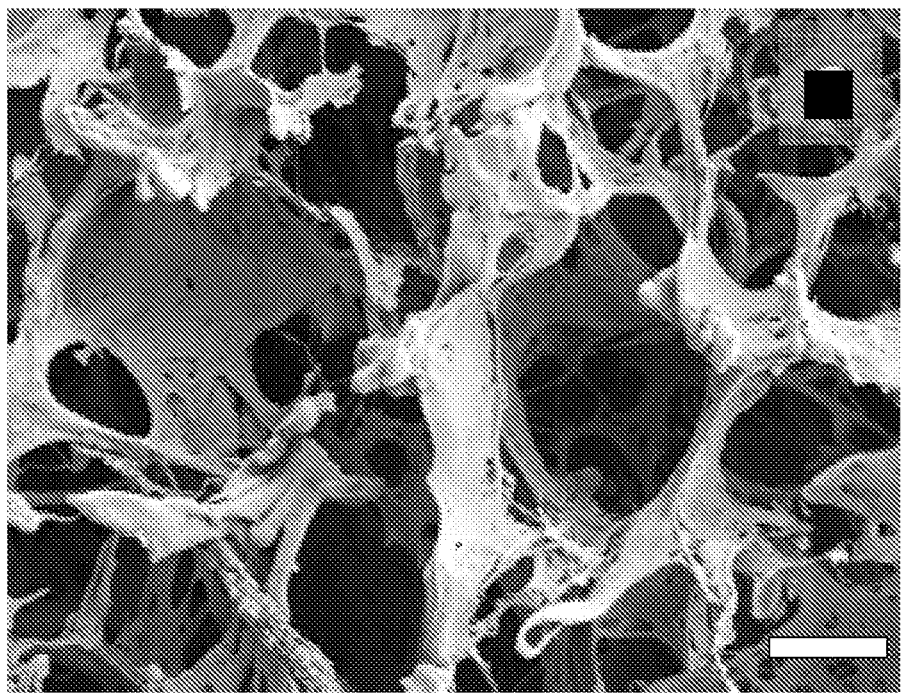
Figure 11D:
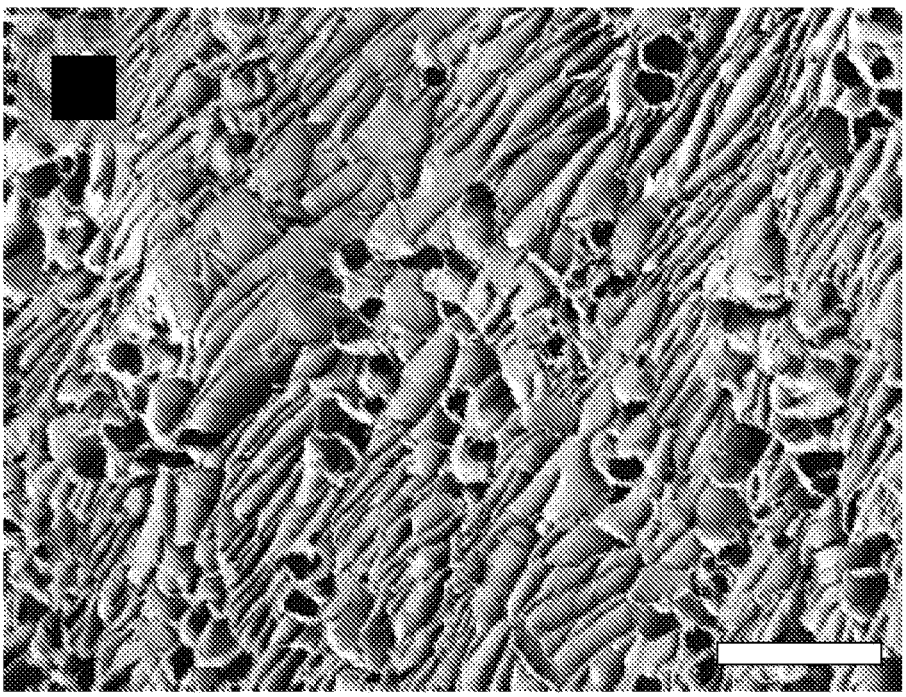
Figure 12A:
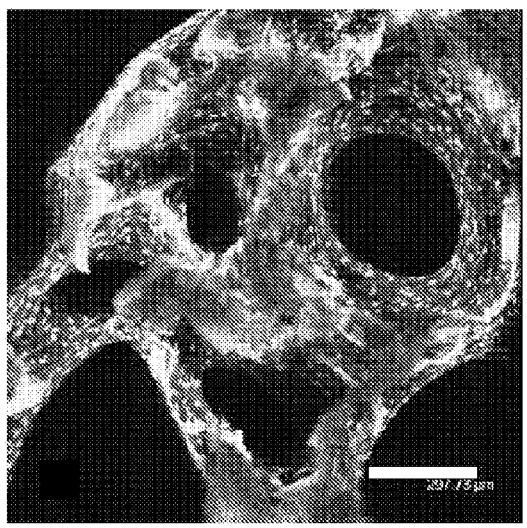
FIGS. 12A to 12L show confocal images of human bone marrow stem cell (hMSCs) showing attachment, growth and proliferation on individual 3D meniscus silk scaffold layers in chondrogenic medium. Initial cell attachment on day 1 (FIGS. 12A, 12E, and 12I); confluent cells covering scaffold pores on day 7 (FIGS. 12B, 12F, and 12J); actin forming fine meshwork on day 14 (FIGS. 12C, 12G, and 12K); and magnified images showing cell alignment and spreading within pores and laminas (FIGS. 12D, 12H, and 12I). Top 102A scaffold layer is represented by FIGS. 12A to 12D; middle 102B layer (FIGS. 12E to 12H) and bottom 104 layer (FIGS. 12I to 12L). Scale bar represents 300 microns.
Figure 12B:
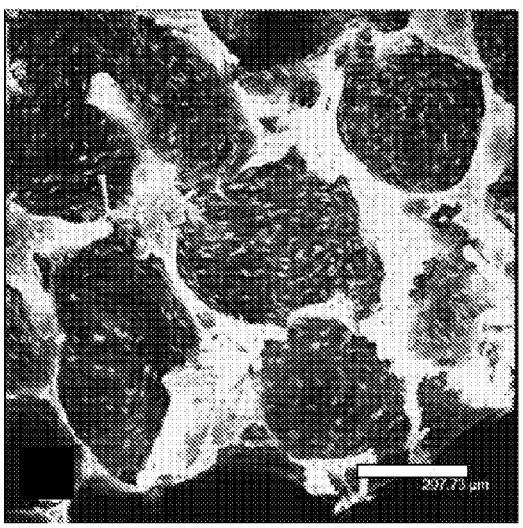
Figure 12C:
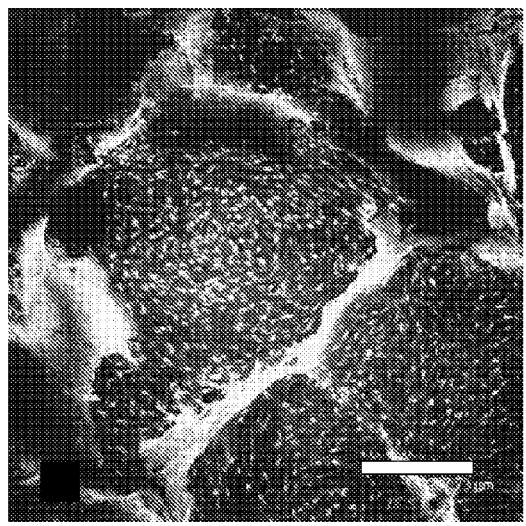
Figure 12D:
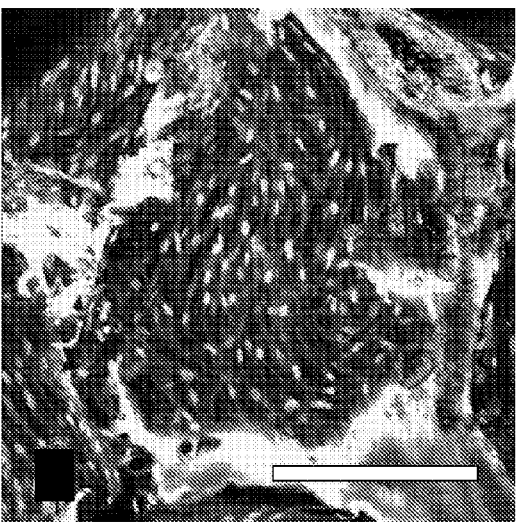
Figure 12E:
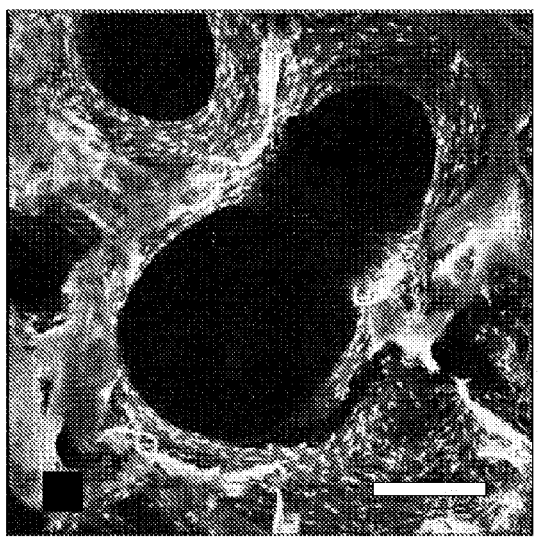
Figure 12F:
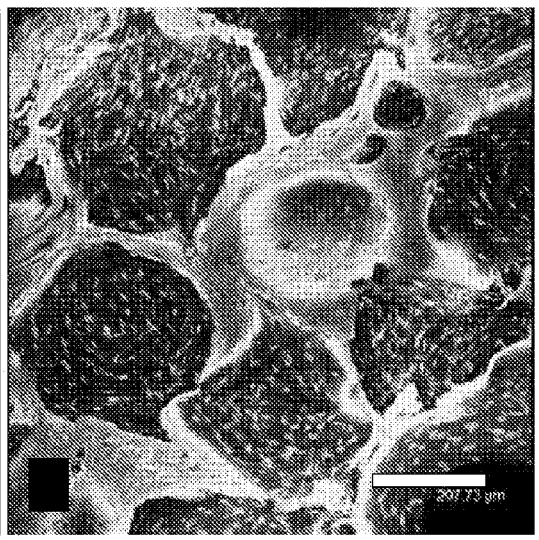
Figure 12G:
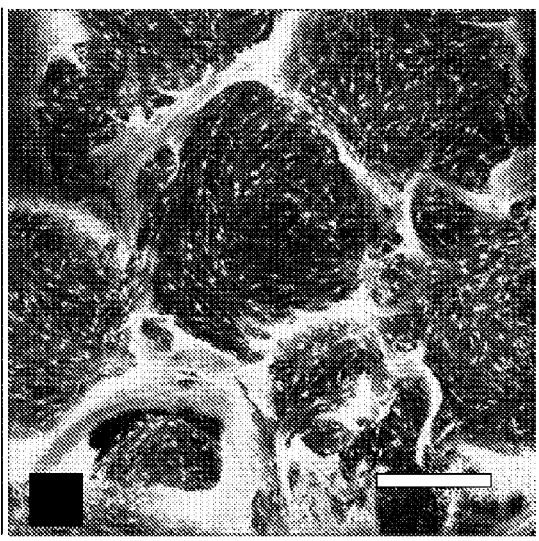
Figure 12H:
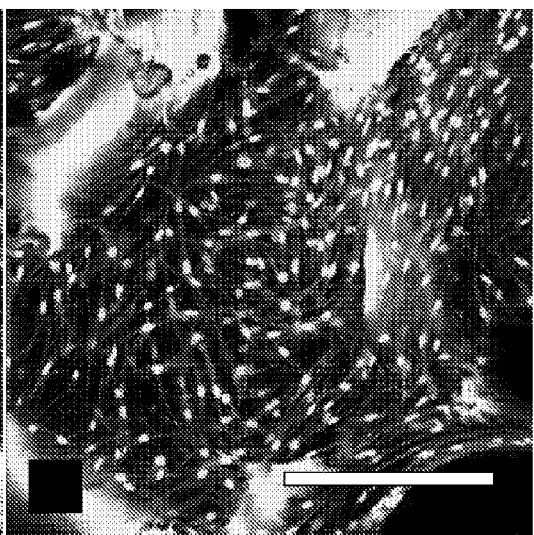
Figure 12I:
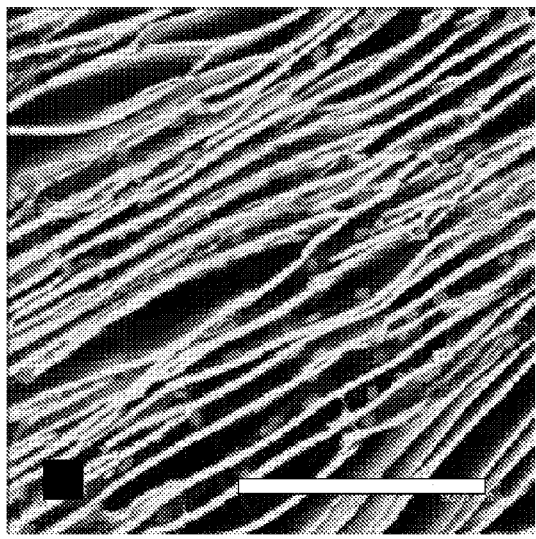
Figure 12J:
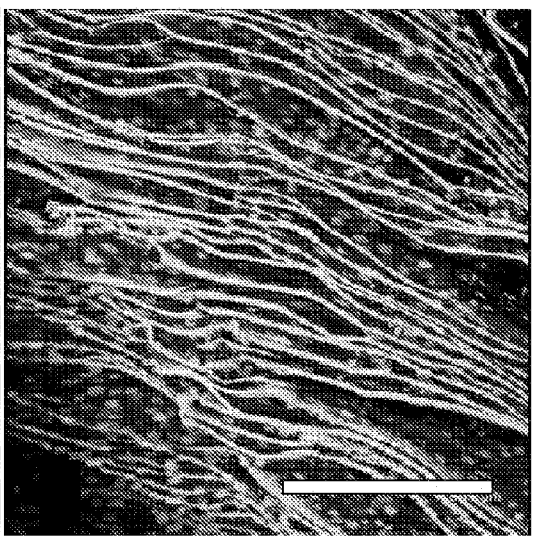
Figure 12K:
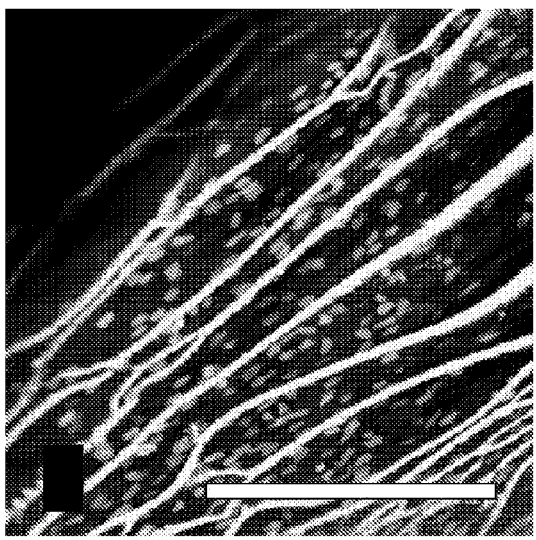
Figure 12L:
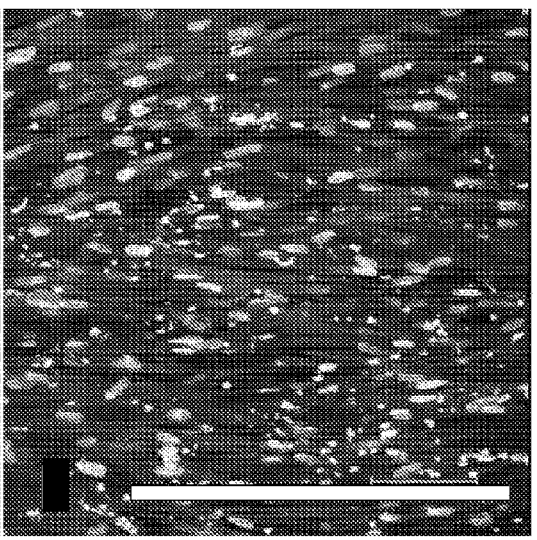
Figure 15A:
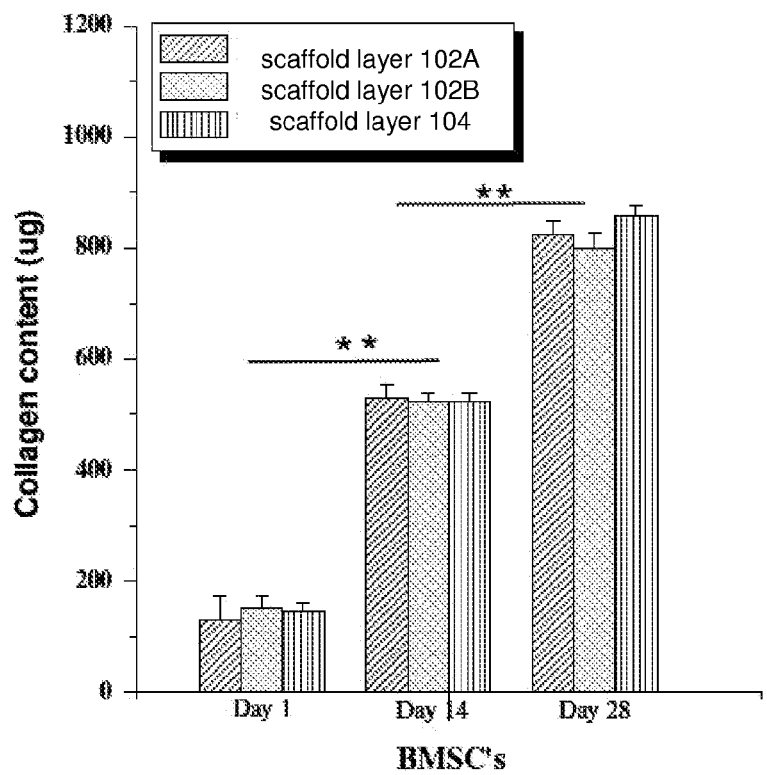
FIGS. 15A to 15D show biochemical assay results estimated in 3 scaffolds layers individually seeded with hMSCs in chondrogenic medium after day 1, 14 and 28.
Figure 15B:
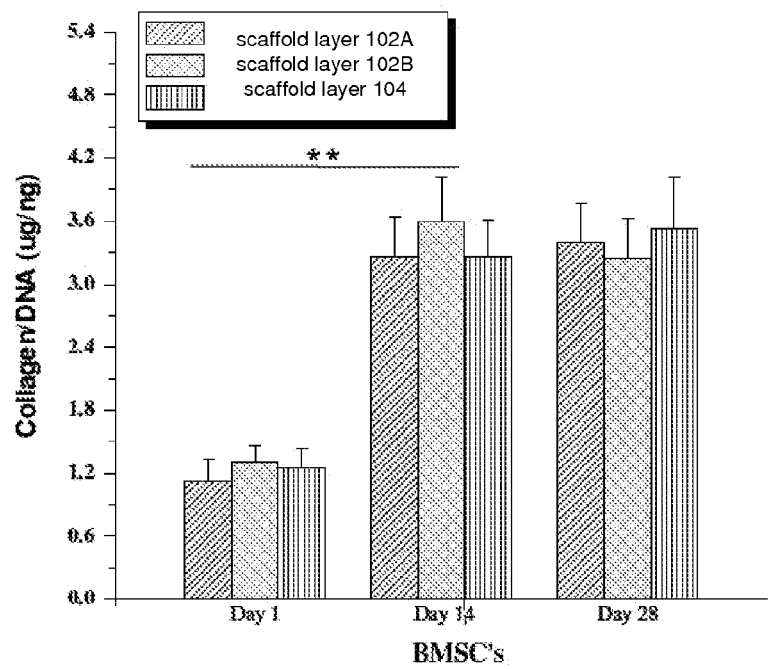

To mimic native meniscus tribiology structure and function in an in vitro wedge shaped silk meniscus model, three layered silk scaffolds having uniform interconnected pores and lamina were fabricated as shown in FIGS. 11A-11D. A gradient of pore size was fabricated using salt leaching method for the first two layers (top and middle) having circular pores in the range of about 350 microns-about 400 microns and about 500 microns-about 600 microns respectively (FIGS. 11B and 11C). While the third (bottom) layer having a laminar morphology was fabricated using freeze drying method with laminar or channel width ranging between about 60 microns-about 80 microns (FIG. 11D). The fabricated scaffolds were wedge shaped (shaped like native meniscus) and three individual layers were stacked on top of each other to form a single unit mimicking meniscus multiporosity (FIG. 11A). The confocal images showed that hMSCs attached and proliferated onto individual silk meniscus scaffold layers (FIGS. 12A to 12L). At day 1, cells appeared clustered and attached onto the walls of the scaffolds. Cell spreading was limited at day 1—the scaffold pore lumen can be clearly observed (FIGS. 12A, 12E, 12I). In comparison, cells completely filled the voids of scaffold pores and spread out actin filaments as early as on day 7. In all three individual silk meniscus layers, cells appeared dense and evenly distributed, and attained confluence (FIGS. 12A to 12L). PicoGreen DNA assay showed that hMSCs proliferated with an increase of approximately ~39%, ~25% and ~36% of their initial cell number at day 14 in the case of $1^{st}$, $2^{nd}$ and $3^{rd}$ layers, respectively (FIG. 15D). While at day 28, hMSCs showed nearly ~108%, ~111% and ~106% proliferation, respectively for 1-3 layers on culturing in chondrogenic media (FIG. 15D). The hMSCs appeared to form intricate meshwork with their actin filaments within scaffold pores for the first two layers while they appeared dense and compact within third bottom scaffold layer having almost linear actin arrangement (FIGS. 12D, 12H, 12L).

Example 7

Histology and Immunocytochemistry of hSMC-Seeded Silk Meniscus Scaffold

Figure 13A:
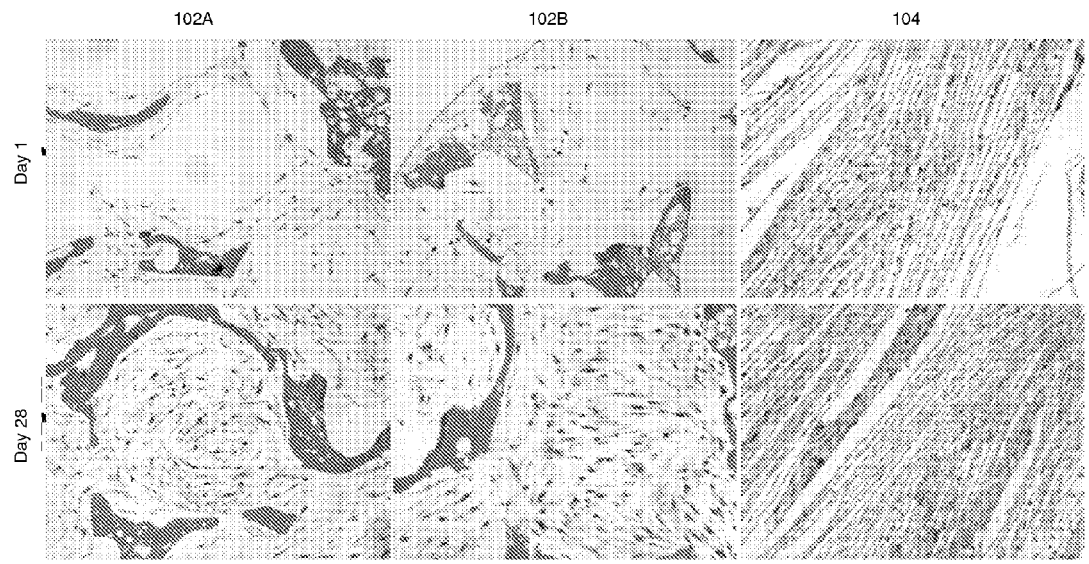
FIGS. 13A to 13 C show histology sections showing hMSC cell growth and ECM deposition on individual 3D silk meniscus scaffold layers in chondrogenic medium. Hematoxylin and eosin staining (FIG. 13A); Alician blue staining (FIG. 13B) and Saffranin O staining (FIG. 13C). Scale bar represents 300 microns.
Figure 13B:
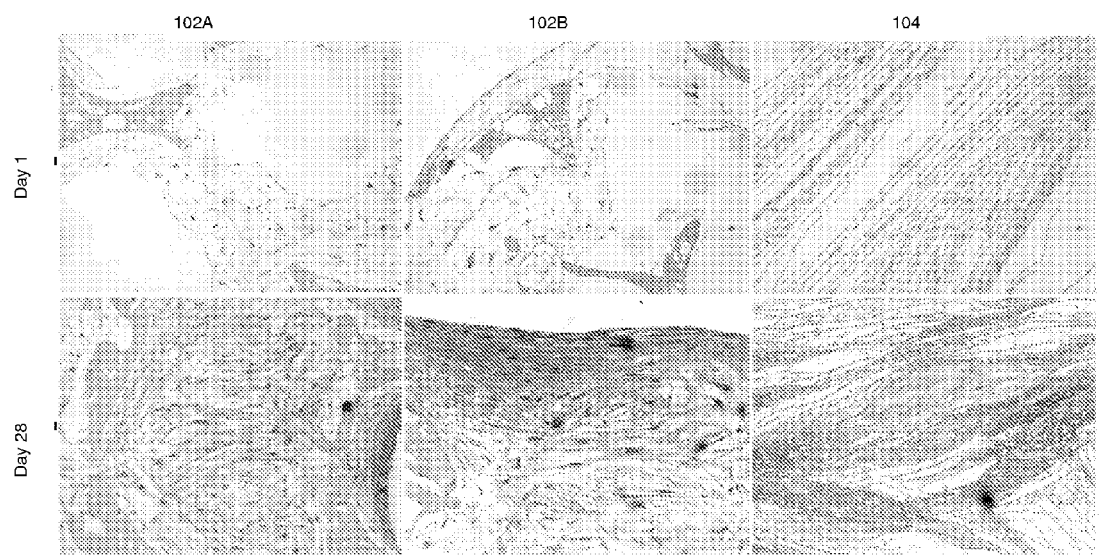
Figure 13C:
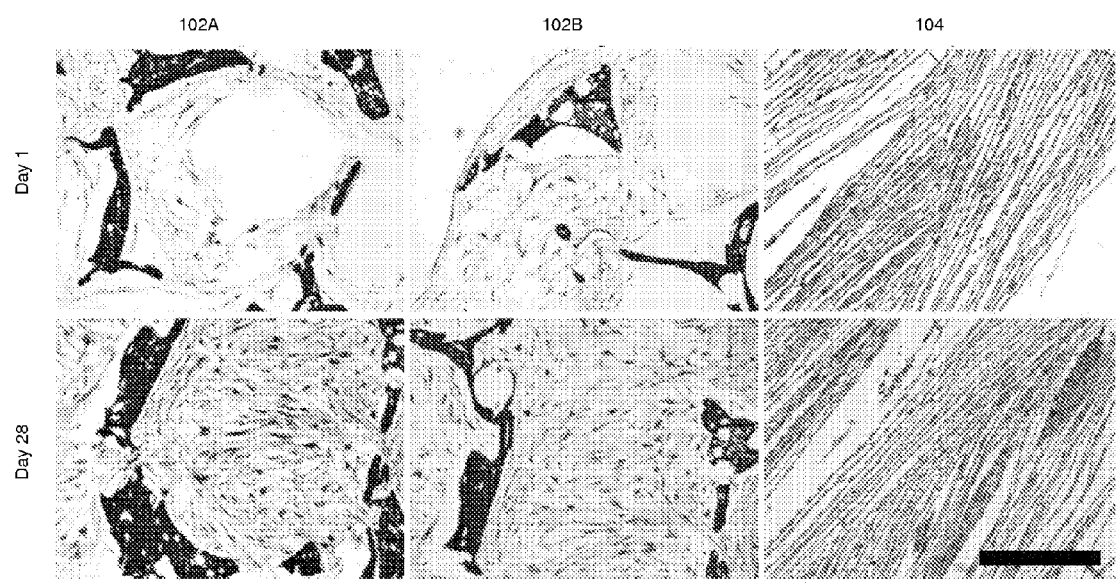
Figure 14A:
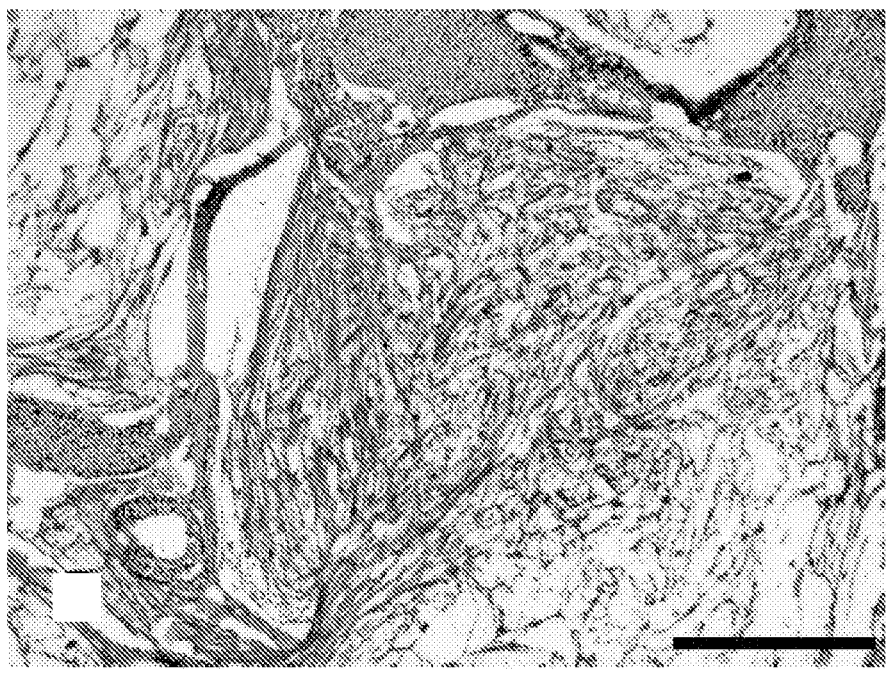
FIGS. 14A to 14F show silk fibroin scaffold histology sections showing immunostaining for collagen type I (FIGS. 14A to 14C) and collagen type II (FIGS. 14D to 14F). hMSCs cultured on different scaffold layers for 28 days using chondrogenic medium. Top 102A scaffold layer is represented by (FIGS. 14A and 14D); middle 102B layer (FIGS. 14B and 14E) and bottom 104 layer (FIGS. 14C and 14F). Scale bar represents 150 microns.
Figure 14B:
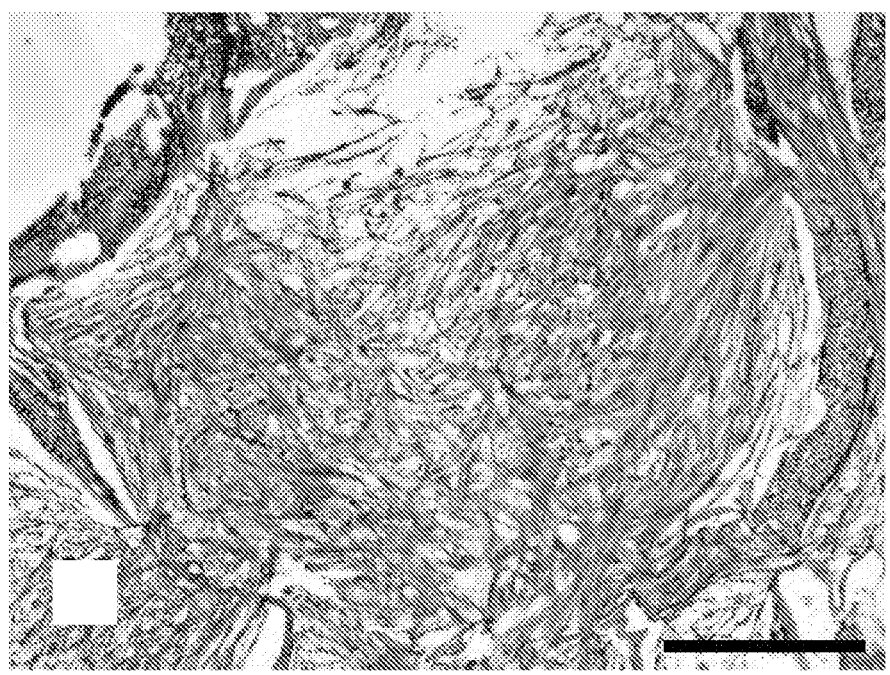
Figure 14C:
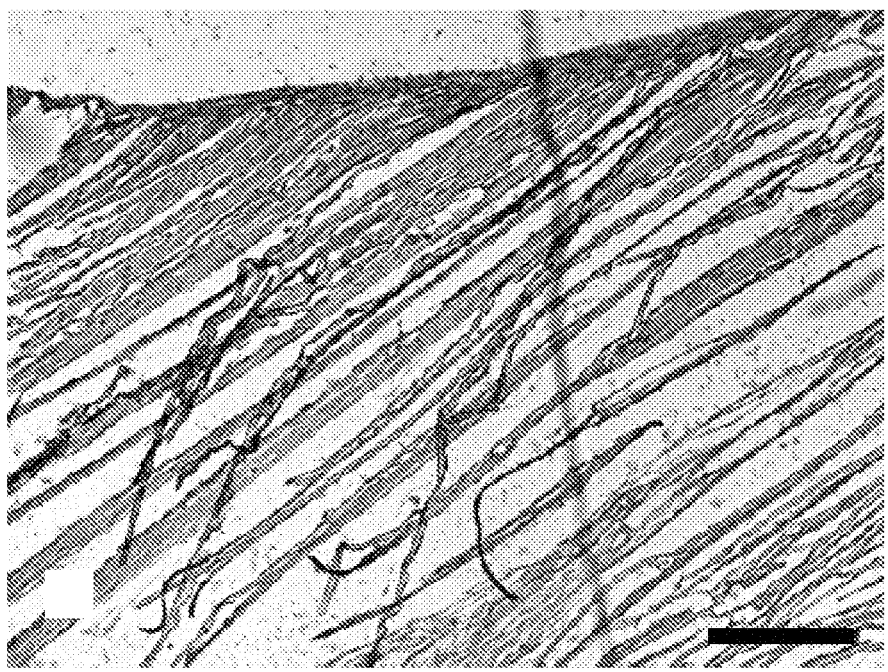
Figure 14D:
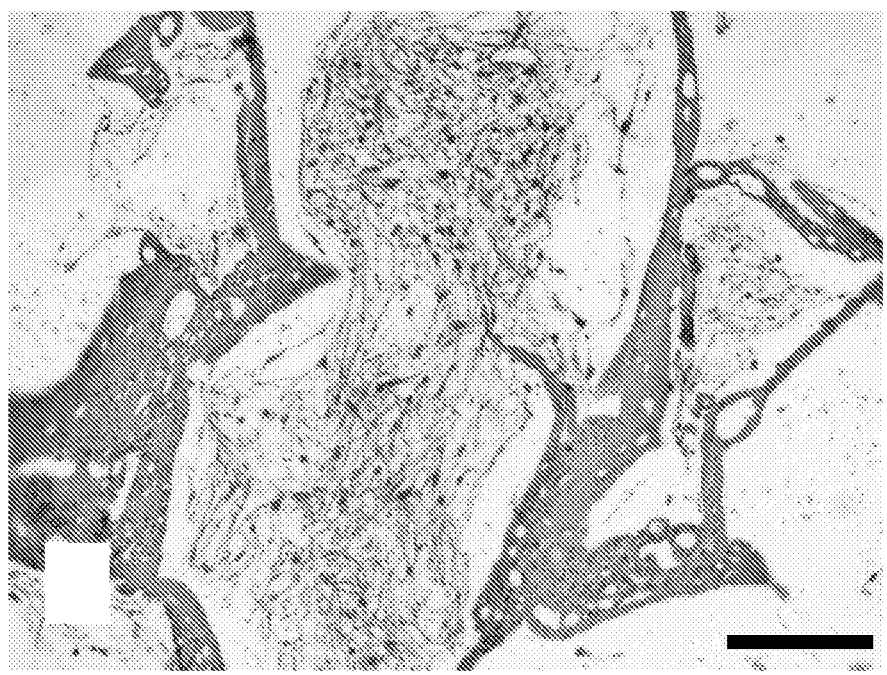
Figure 14E:
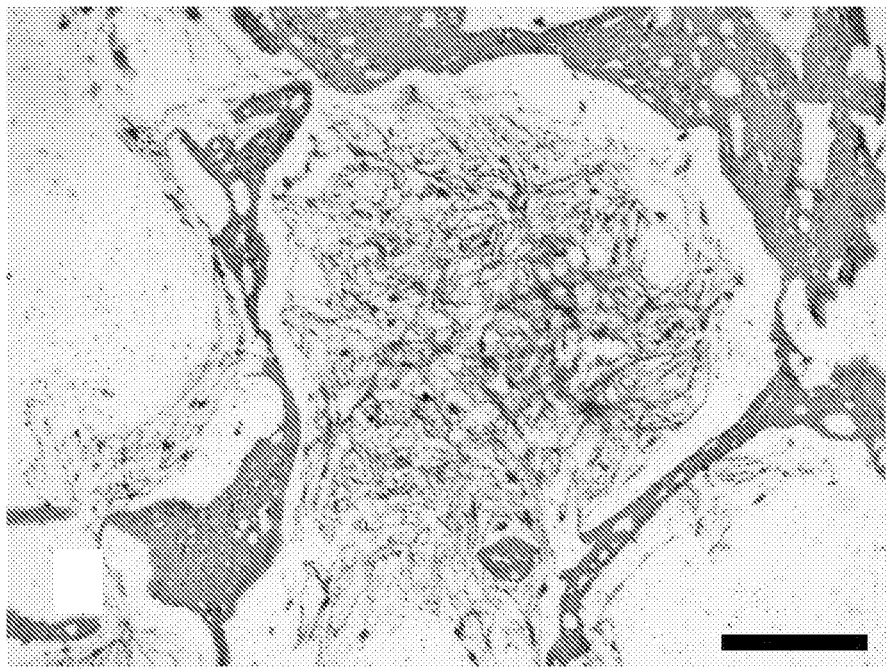
Figure 14F:
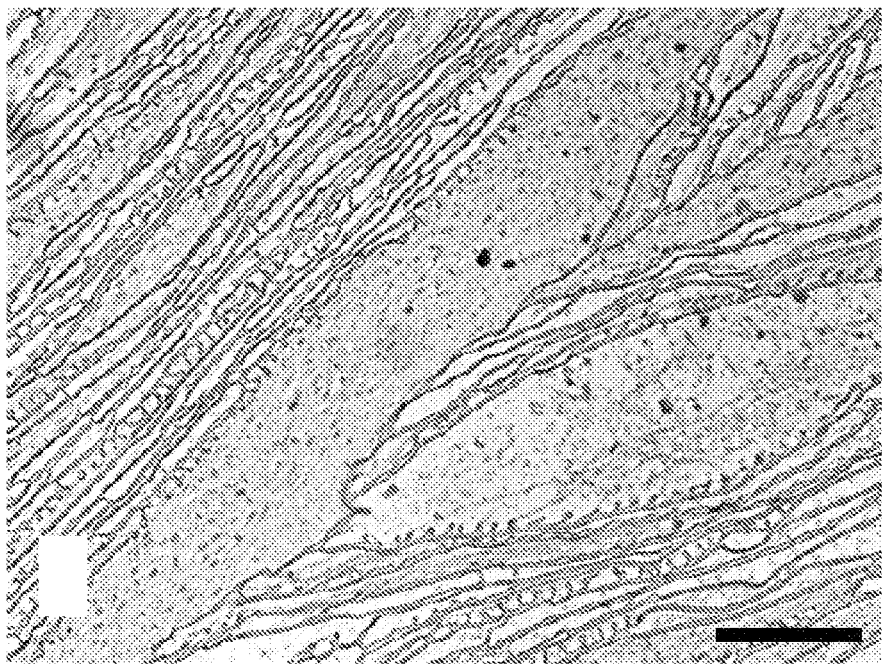

Histology sections of individual silk meniscus scaffold layers revealed accumulation of sGAG and collagen with time (day 28 vs day 1) (FIGS. 13A-13C, 14A-14F). For Alician blue, Saffranin O and H & E, scaffolds showed intense staining on day 28 as compared to day 1 for hMSCs growing in chondrogenic medium (FIGS. 13A, 13B, 13C). Particularly for Alician blue staining, hMSCs showed intense blue color, a hallmark for abundant sGAG deposition, indicating differentiation towards chondrogenic lineage. In comparison to the top and middle porous layers, the third bottom laminar scaffold layer with differentiating hMSCs showed more compact and intense deep blue staining, indicating matured chondrocyte phenotype (FIG. 13B). For the top and middle layers, though alician blue staining was comparable and intense as the bottom third layer, the cells appeared less compact when culturing in chondrogenic medium (FIGS. 12A-12L, 13A-13C, 14A-14F). Similarly, intense Saffranin O stains confirmed sGAG accumulation within all scaffold layers, indicating differentiation of hMSCs towards chondrocytes at day 28. Further, H&E staining revealed cell attachment and distribution within each scaffold layer indicating growth and proliferation with time (FIG. 13A). In all cases, cells appeared scattered throughout scaffold pores/layers on day 1, but attained confluence by filling void spaces on day 28.

Immunocytochemistry staining revealed presence of collagen type I and II deposition within silk scaffold layers at day 28. Differentiating hMSCs showed abundant collagen type I and/or collagen type II deposition on day 28 in all silk layers (FIGS. 14A-14F). Further collagen depositions distributed homogenously throughout the pores.

Example 8

Biochemical Analysis of hMSC-Seeded Individual Meniscus Scaffold

Histology and immunocytochemistry data was further supported by biochemical analysis data confirming differentiation of hMSCs into a mature chondrocytic phenotype within the scaffold meniscus layers. Both the collagen and sGAG amount increased with time ($p \leq 0.01$) (day 28 vs day 1) (FIGS. 15A-15D, 16A-16D). Total collagen amount in differentiating hMSCs increased approximately ~271% (520 μg) and ~492% (820 μg) at day 14 and 28 respectively, in all three scaffold layers when compared to day 1 (140 μg) ($p \leq 0.01$) (FIGS. 15A-15D). No statistically significant difference in the total collagen content was observed between the three individual scaffold layers at the three time points. Similarly, the total sGAG content (scaffold+media) increased approximately by ~50% (30 μg) and ~176% (93 μg) in chondrogenic medium at the end of day 14 and 28 respectively, when compared to day 1 (5 μg) for all silk scaffold layers, irrespective of the difference in morphology ($p \leq 0.01$) (FIGS. 15A-15D). Substantial amount (~40-50%) of total detected sGAG was secreted into the medium over time while culturing these differentiating cells in chondrogenic medium (FIGS. 16A-16D). At day 14, estimated sGAG amount in medium was approximately ~13 μg, which increased to ~47 μg at the end of day 28 ($p \leq 0.01$) (FIGS. 16A-16D).

Figure 16A:
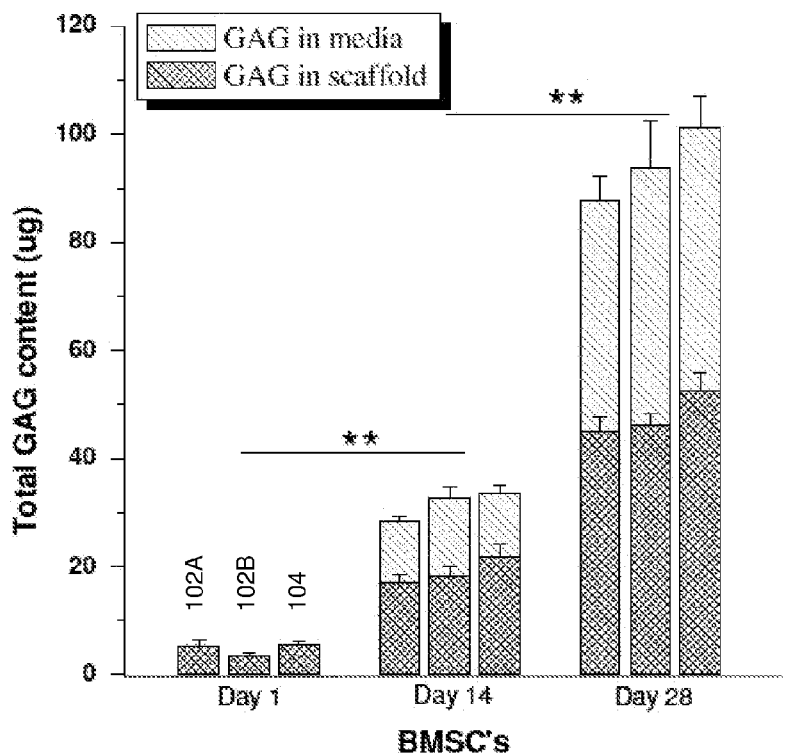
FIGS. 16A to 16D show biochemical assay results estimated in 3 scaffold layers individually seeded with hMSCs in chondrogenic medium after day 1, 14 and 28.
Figure 16B:
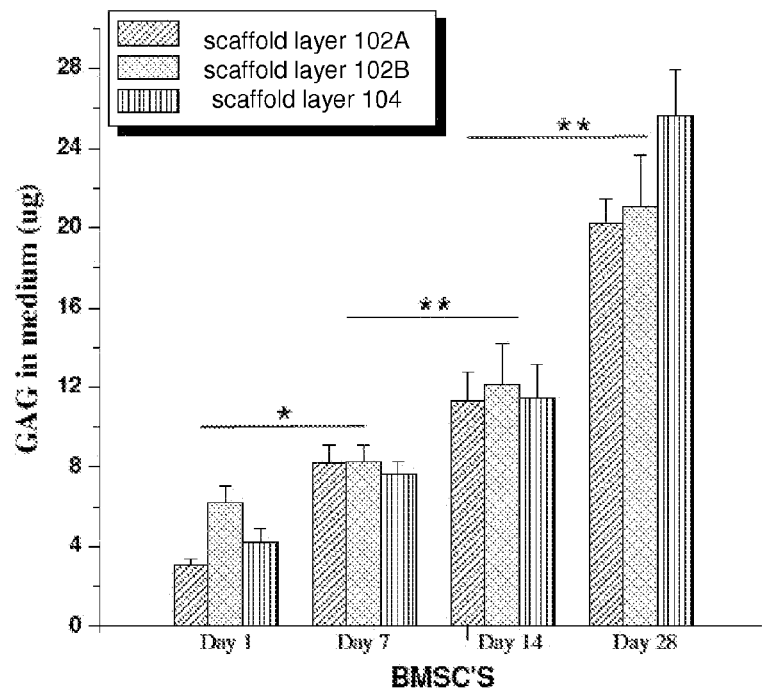
Figure 16C:
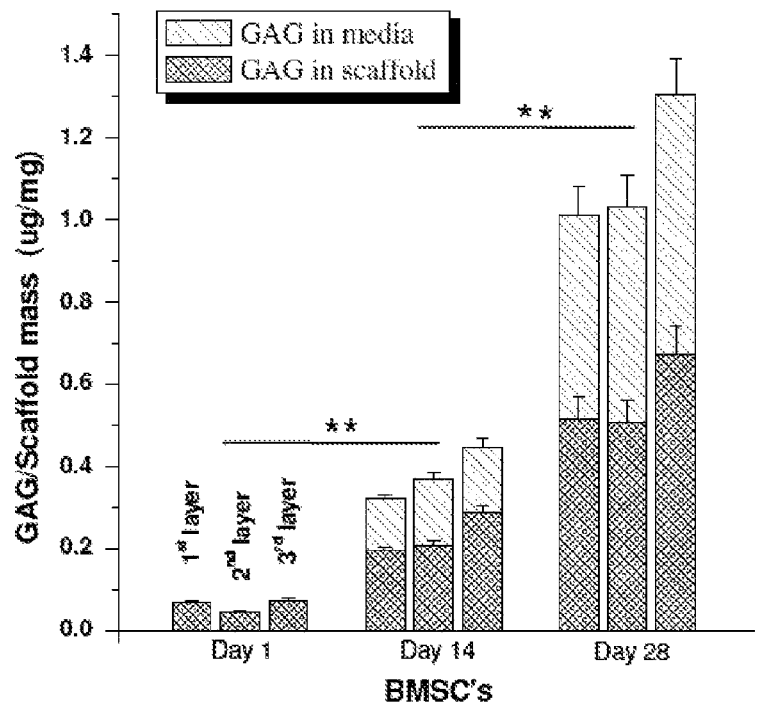
Figure 16D:
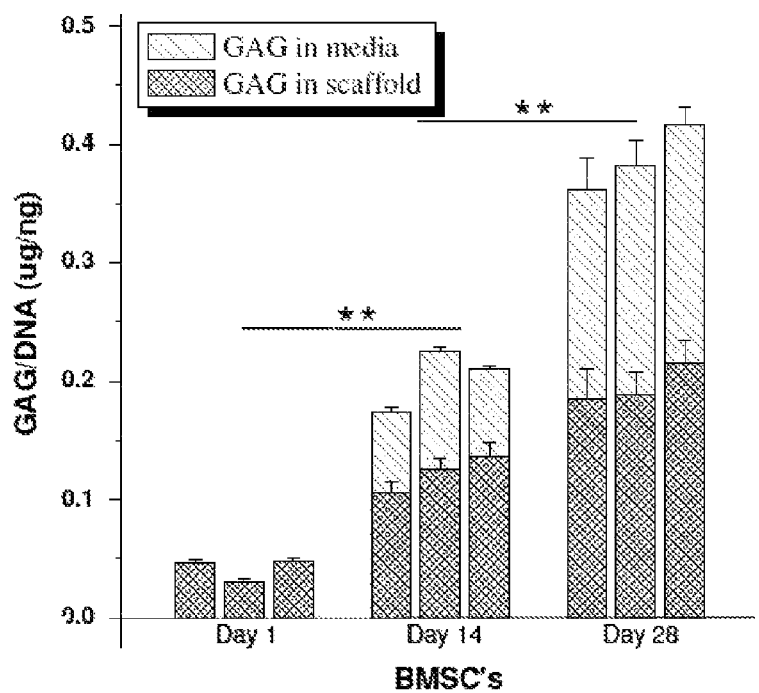

To minimize discrepancy within individual scaffold layer groups due to different initial cell seeding, total collagen and sGAG content was presented by normalizing it with total DNA amount from the same day. The normalized collagen content per unit DNA increased ~1.75 fold (3.3 μg/ng) at day 14 in all layers when compared to day 1 (1.2 μg/ng) ($p \leq 0.01$), although the relative amount was constant at day 28 ($p \leq 0.01$) (FIG. 15B). Individual scaffold layers showed no statistically different values for collagen per unit DNA in either of the days. Similarly, total sGAG per unit DNA (present in media and deposited in scaffolds) after 28 days of culturing, increased by ~9.75 fold (0.39 μg/ng) in the case of differentiating hMSCs as compared to ~3.2 fold (0.128 μg/ng) after day 14 ($p < 0.01$) (FIG. 16D). Compared to the deposited sGAG within scaffolds, secreted GAG in medium was ~30-50% of the total content in all the three silk fibroin layers (FIGS. 16A-16D). To assess sGAG secretion by hMSCs, the sGAG amount was estimated in chondrogenic medium from individual silk scaffold layers for 28 days (FIG. 16B). Differentiating hMSCs slowly enhanced their sGAG production with time, indicting the onset of differentiation events leading towards the attainment of a matured chondrocyte phenotype. Maximum sGAG production was reached at day 28, amounting to ~20 μg-25 μg when compared to ~3 μg-6 μg, ~7 μg-8 μg and ~12 μg on day 7, 14 and 21, respectively (FIG. 6A). This trend was observed for all three silk meniscus layers without any statistical difference in between layers.

Figure 15C:
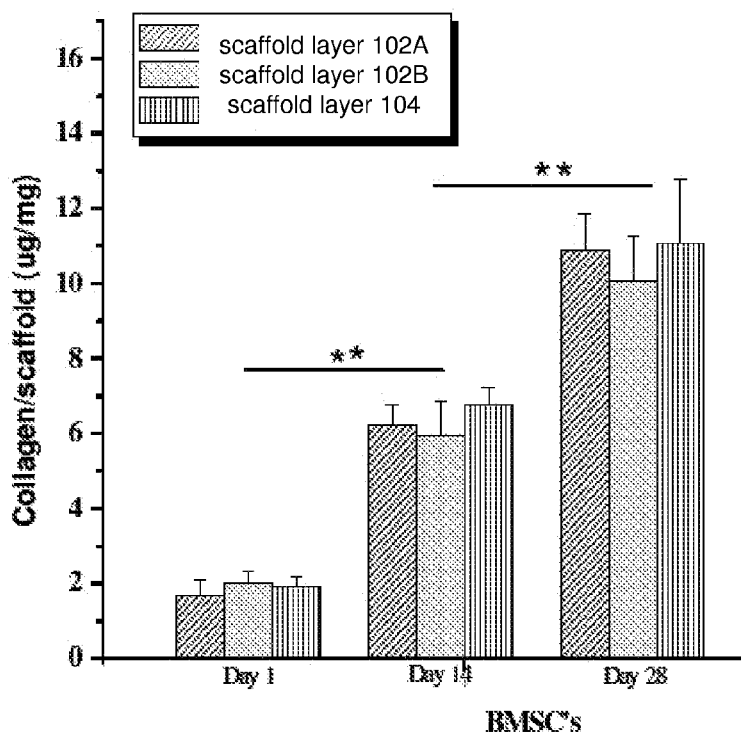
Figure 15D:
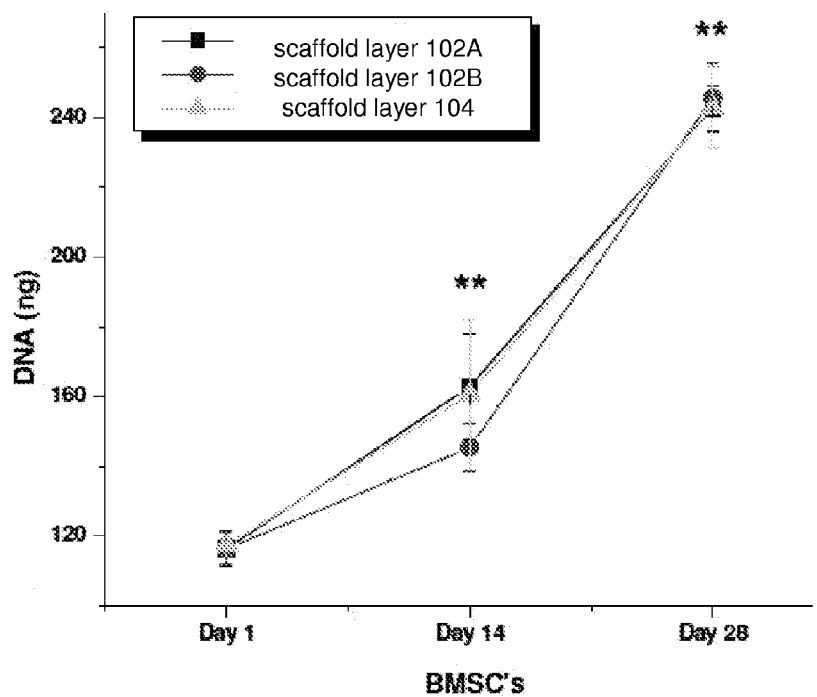

To monitor the effect of individual scaffold mass, volume and morphology on hMSCs differentiation and maturation as well as on ECM deposition (if any), total collagen and sGAG amount was normalized as per unit scaffold mass (FIG. 15C). Upon normalization, total collagen amount was independent of unit scaffold mass and morphology in individual layers, resulting in similar collagen deposition at day 1, 14 and 28 (FIG. 15C). However, there was a constant increase in total collagen content amounting to approximately ~6 μg/mg and ~11 μg/mg scaffold at the end of day 14 and 28 when compared to ~2 μg/mg scaffold at day 1 ($p \leq 0.01$) (FIG. 15C). Similarly, upon normalization, no significant difference in sGAG amount was observed for differentiating hMSCs per unit scaffold within individual silk scaffold layers at day 1, 14 and 28. However, similar to the total collagen content, the sGAG amount also increased with time both in medium and within scaffolds amounting to ~0.35 μg/mg-0.45 μg/mg and ~1 μg/mg-1.3 μg/mg scaffold at day 14 and 28 respectively, as compared to ~0.04 μg/mg-0.06 μg/mg scaffold at day 1 (FIG. 16C).

Example 9

Real Time Gene Expression of hMSCs within Meniscus Scaffold

Figure 17A:
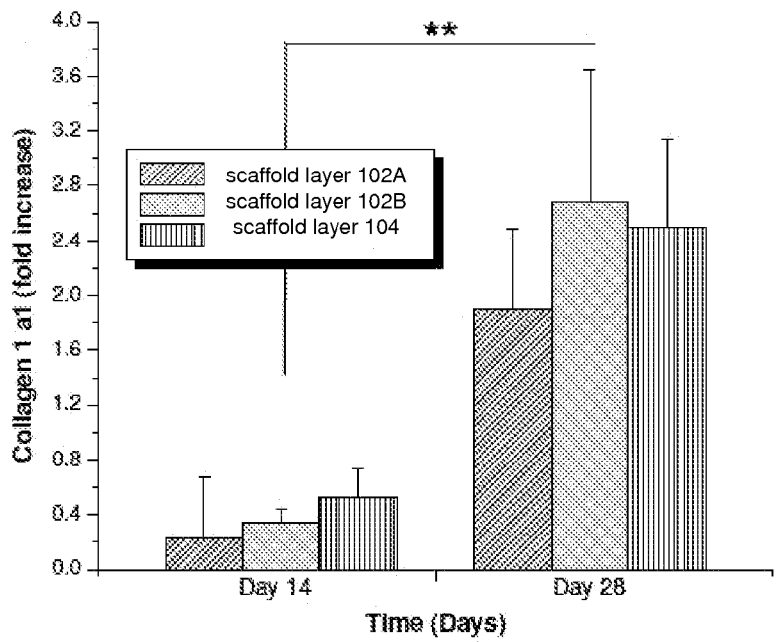
FIGS. 17A to 17D show results of real time gene expression results of differentiating hMSCs within individual scaffold layers in chondrogenic medium after day 14 and 28.
Figure 17B:
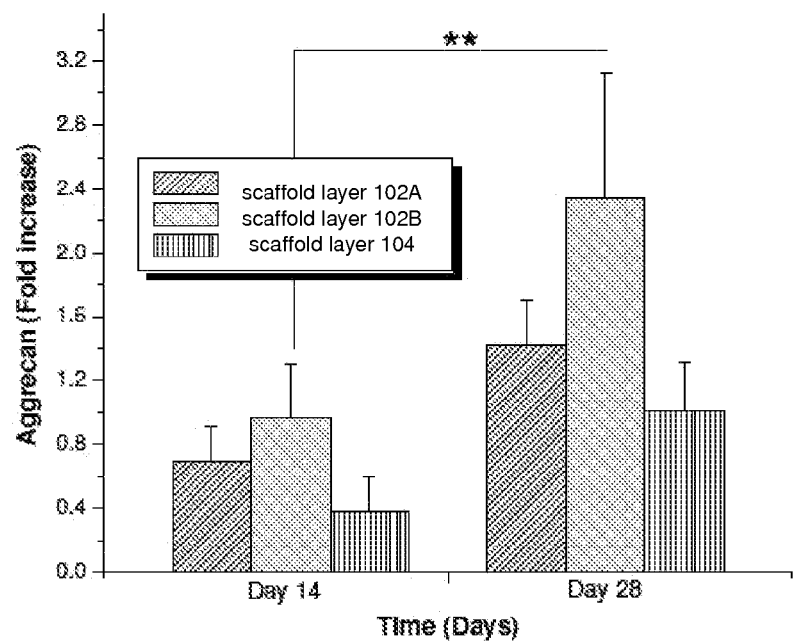
Figure 17C:
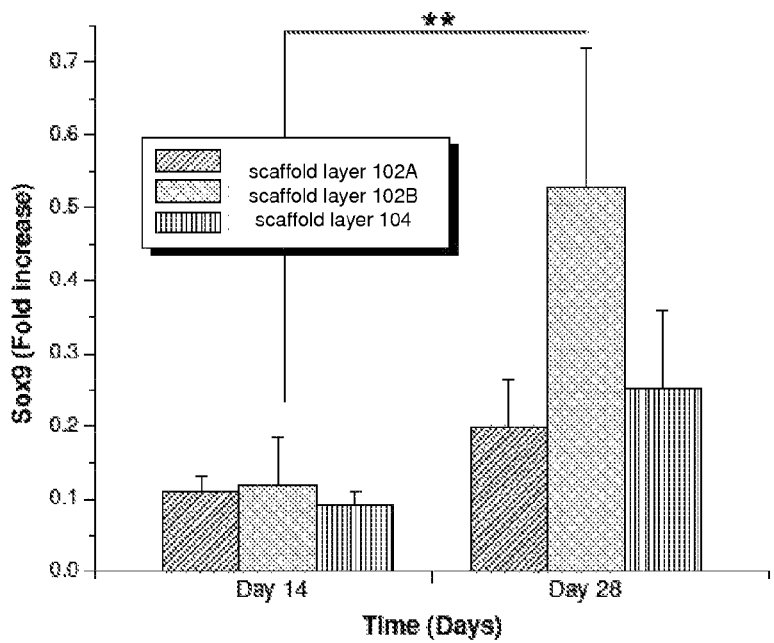
Figure 17D:
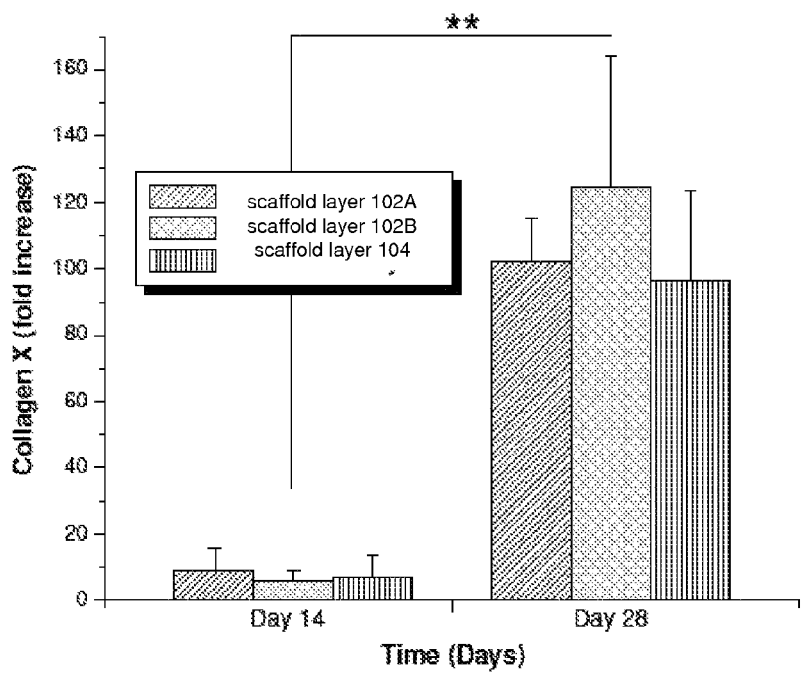

To further support biochemical results and confirm chondrogenic differentiation of hMSCs to produce mature meniscus like tissue, real-time RT-PCR was carried out for cartilage specific genes. When culturing hMSCs in chondrogenic medium for 28 days, there was an up-regulation of all chondrogenic marker genes with time, indicating in vitro chondrogenesis in silk scaffolds irrespective of individual layer and scaffold morphology. Further, expression of collagen 1-α-1, a major constituent of native meniscus cell phenotype, increased nearly 5-fold at day 28 when compared to day 14 ($p \leq 0.01$) (FIG. 17A). Similarly, expression of Sox9 and aggrecan genes, considered hallmark for matured chondrocyte phenotype, enhanced with time, reaching maximum at day 28 ($p \leq 0.01$) (FIGS. 17B, 17C). However, an increase in expression of collagen X gene was also marked within silk scaffolds with time ($p \leq 0.01$) (FIG. 17D).

Meniscus allograft/autograft transplantation represents a potential tissue engineering solution for the symptomatic, meniscus deficient patients to substitute for lost meniscal tissue, to prevent cartilage degeneration, to relieve pain and to improve function. To design and fabricate native-like meniscus tissue constructs, 3D multiporous, multilamellar meniscus scaffolds seeded with hMSCs were engineered, mimicking native meniscus tribiology morphology for future graft applications (FIGS. 11A-11D). Apart from recreating native like meniscus tribiology in vitro 3D model as proposed by Petersen and Tillmann (1998), hMSC-scaffold interactions and changes related to hMSCs differentiation towards matured chondrocytes due to varied morphological features within these silk constructs were evaluated herein.

In contrast to the available clinical option of allograft meniscus, which is often related with disadvantages including shape incongruency, disease transmission and limited donor availability, a custom design of the lost/defective part using different cell-sources, growth-factors, scaffolds and their combinations, together with the possibility of using autologous cells, makes the research of tissue engineered meniscus advantageous and exciting (Baker and Mauck, 2007; Baker et al., 2009; Mauck et al., 2007, Angele et al., 2007). In the fabricated silk constructs according to one or more embodiments provided herein, the porous scaffold framework having pores of 350 microns-400 microns and 500 microns-600 microns can provide mechanical support to the growing cells for ECM deposition over time, thus making a similar fine meshwork as in the Petersen and Tillmann's model (1998). Further, the highly interconnected pores support growing hMSCs to migrate, and nutrient and wastes to flow in and out into the outside medium (FIGS. 11A-11D, 12A-12L). The construct design as provided herein is an important development over the previous studies reporting a lack of cell migration into the inner core of the construct due to smaller pores for migrating cells and increased cell death in the inner core regions due to media transport hindrance (Baker and Mauck, 2007; Baker et al., 2009). The Picogreen assay results showed doubling of hMSCs within all the scaffold layers, including the third bottom layer (with smaller laminar channels), indicating that the cells were differentiated within the layers and proliferated to double their initial seeding numbers, a sign of growth microenvironment within pores and laminas of the construct (FIGS. 15A-15D).

Due to the higher intrinsic mechanical properties of silk fibroin, the outer scaffold structure can aid resisting high in vivo shear forces during future implantation studies (Altman et al., 2003). Similarly, due to initial difference in the scaffold pore size in the top two layers, a difference in ECM network was observed as hMSCs tend to reorient and reorganize as per available pore size, as further confirmed from the confocal and histology images of the scaffold mimicking the top and middle native meniscus architecture (FIGS. 12A-12L). It has been previously reported that high intrinsic tensile and compressive properties of meniscus tissues are attributed by the aligned and linearly organized collagen fibers lying at the bottom of the construct (Sweigart and Athanasiou, 2001; Tissakht and Ahmed, 1995; Petersen and Tillmann, 1998). To reorganize hMSC-deposited collagen similar to native meniscus, laminar silk groves of 60 microns-80 microns were fabricated to act as templates to allow seeded hMSCs to grow, proliferate and align within these channels (FIGS. 11A-11D, 12A-12L). Differentiating hMSCs deposited their ECM (mainly collagen and GAG) over time, mimicking native tissue morphology and arrangement (mesh and laminar), as confirmed from the confocal and histology sections (FIGS. 12A-14F).

In addition to regeneration of a native meniscus tribiology structure, mimicking its fibrocartilaginous cellular phenotype is essential for engineering clinically-functional meniscus grafts. Recapitulation of native-like meniscus fibrocartilaginous structure was achieved within the scaffold layers described herein seeded with hMSCs differentiated towards mature chondrocytic lineage using specific media and factors. The confocal images showed that the silk scaffolds as described herein was biocompatible, where confluent hMSCs occupied void scaffold pores with good actin filament development and spreading, a sign of normal growth and development (FIGS. 12A-12L). Similarly, enhanced cell proliferation within the scaffolds layers based on the DNA content supported cell compatibility issues of these constructs for future graft applications ($p \leq 0.01$) (FIG. 15D). Further, the use of late passage hMSCs (P7) for the experiments presented herein do not seem to critically affect chondrogenic differentiation (based on biochemical and gene expression studies) towards mature chondrocytic phenotype to attain features similar to native meniscus. Accordingly, these in vitro silk meniscus constructs can successfully support late passage cells for growth and differentiation. Intense staining of sGAG in the histology sections confirmed differentiation of seeded hMSCs to mature chondrocyte phenotype with enhanced proteoglycan production within all individual layered silk layers comparable to native like tissue where proteoglycans make for 2-3% of the dry weight and form the cartilaginous zone of the meniscus ($p \leq 0.01$) (Adams and Hukins, 1992; McDevitt and Webber, 1990; Buma et al., 2004) (FIGS. 13A-13C). GAGs can play an all important role in the maintenance of optimal visco-elastic behavior, compressive stiffness, and tissue hydration due to its high water content (~78%), thus facilitating a smooth frictionless movement of the menisci over the articular surfaces of the tibia and femur (Ghosh and Taylor, 1987, Setton et al., 1999). The importance of cellular and cell-scaffold interactions in differentiation events can be realized from the cell shape of growing hMSCs, as they appear more elongated within the bigger pores but show a more compact morphology similar to mature chondrocytes when observed within the $3^{rd}$ (bottom) laminar layers (FIGS. 12A-14F). This is further supported by intense alician blue and saffranin O staining of the bottom layer along with higher ECM amount. The bottom laminar layer also produced higher sGAG as compared to the other two top layers with time in presence of chondrogenic medium with TGF-b3 ($p \leq 0.01$) (FIGS. 13B, 13C). Not limiting by the theory, due to limited space available in the bottom layer as compared to bigger pores in top and middle layers, cells can interact more closely not only within themselves but also with the surrounding scaffold, resulting in the observed morphological changes.

Increased total collagen amount supported hMSCs growing and ECM depositions within pores and laminas of all individual silk layers, as similar to native like meniscus (p≤0.01). Knee meniscal fibrocartilaginous tissue has been reported to contain mainly water (72%), collagens (22%) and glycosaminoglycans (0.8%) (Proctor et al, 1989; Herwig et al, 1984). Of the total collagen content, Type I collagen accounts for over 90% and the remaining 10% of meniscal collagens are Type II, III and V collagen (Eyre and Wu, 1983; McDe'vitt and Webber, 1990). The immuno staining presented herein showed similar ratios of collagen type I and II within the silk scaffolds according to one or more embodiments of the invention, where collagen I was more abundant when compared to collagen type II, a feature similar to native meniscus (FIGS. 14A-14F) (Adams and Hukins, 1992, Eyre and Wu, 1983; McDe'vitt and Webber, 1990). Further, the presence of numerous collagen type I bundles oriented in a circumferential direction similar to the orientations in native meniscus, as observed at day 28, particularly in the bottom third layer (FIGS. 14C, 14F), can impart strong tensile properties, thus preventing radial extrusion of the meniscus and maintaining the structural integrity during load bearing events (Ghosh and Taylor, 1987, Setton et al., 1999, Sweigart and Athanasiou, 2001; Tissakht and Ahmed, 1995; Petersen and Tillmann, 1998).

Gene expression within all silk scaffold layers further supported hMSC differentiation and applicability of these constructs for potential meniscus engineering. Transcript levels of cartilage-related ECM gene markers such as Col-1-α1, aggrecan (AGC), Col-X, and Sox 9 were markedly induced or significantly up-regulated in hMSC-silk scaffold cultured in chondrogenic medium supplemented with TGF-b3 (FIGS. 17A-17D). As the major constituent of native meniscus (Eyre and Wu, 1983; McDe'vitt and Webber, 1990), up-regulation of collagen type I gene further supports the biochemical assay results presented herein. Similarly, Sox9, a key transcription factor for chondrogenic differentiation and cartilage formation, up-regulated and is believed to precede the up-regulation of cartilage-specific genes during in vitro chondrogenesis (Chimal-Monroy et al., 2003, Sekiya et al., 2000). In the silk meniscus constructs described herein, the expression of Sox9 agreed with higher aggrecan expression indicating its induction (FIGS. 17B, 17C). During the differentiation event, Collagen type X expression increased significantly. The gene collagen type X has been previously reported to encode the alpha chain of type X collagen, a short chain collagen expressed by maturation to hypertrophic chondrocytes during endochondral ossification (Koga et al., 2007, Nehrer et al., 1999, Sellers et al., 1997). Similar observations were reported by Wang et al., showing that increasing the initial cell seeding numbers can achieve a reversal of the effect (Wang et al., 2006 b). In some embodiments, increasing the initial cell seeding number as described herein can be used in the meniscus silk fibroin scaffold. In some embodiments, the silk fibroin scaffold can comprise the vascular and avascular zones as present in native meniscus.

In accordance with one embodiment of the invention, presented herein is the fabrication of a wedge shaped multilamellar/multiporous silk meniscus scaffold seeded with hMSCs, wherein the hMSCs can be differentiated towards mature chondrocytic phenotype, mimicking native-like tissue structure. The scaffold layers can act as guided templates for neo-tissue formation and allow deposited ECM to reorganize. Further, cultured hMSCs showed higher cellularization with aligned ECM depositions, based on the higher collagen and proteoglycans levels, accompanied by higher gene expression levels. Such findings support chondrocytic differentiation within fabricated silk constructs as described herein. In one embodiment, no significant difference in ECM deposition and cell growth was observed within different scaffold layers, except for observed cell morphology changes. Biochemical studies over time can be important for improved mechanics for in vivo applications. The fabricated silk meniscus presented herein can be used for meniscal defects repair, a prevalent and otherwise untreatable orthopaedic condition.

REFERENCES

For Examples 1-5

M. Englund, E. M. Roos, L. S. Lohmander, Impact of type of meniscal tear on radiographic and symptomatic knee osteoarthritis: a sixteen-year follow up of meniscectomy with matched controls, Arthritis Rheum. 48 (2003) 2178-2187.
T. J. Fairbank, Knee joint changes after meniscectomy, J. Bone Joint Surg. Br. 30B (1948) 664-670.
F. Chatain, P. Adeleine, P. Chambat, et al., A comparative study of medial versus lateral arthroscopic partial meniscectomy on stable knees: 10-year minimum follow-up, Arthroscopy 19 (2003) 842-849.
B. J. Cole, T. R. Carter, S. A. Rodeo, Allograft meniscal transplantation: background, techniques, and results, Instr. Course Lect. 52 (2003) 383-396.
Wolf Petersen and Bernhard Tillmann. Collagenous fibril texture of the human knee joint menisci. Anat Embryol (1998) 197:317-324
O'Connor B L. The histological structure of dog knee menisci with comments on its possible significance. Am J Anat 1976; 147:407-417.
Proctor C S, Schmidt M B, Whipple R R, Kelly M A, Mow V C. Material properties of the normal medial bovine meniscus. J Orthop Res 1989; 7:771-82.
Herwig J, Egner E, Buddecke E. Chemical changes of human knee joint menisci in various stages of degeneration. Ann Rheum Dis 1984; 43:635-40
Eyre D R, Wu J J. Collagen of fibrocartilage: a distinctive molecular phenotype in bovine meniscus. FEBS Lett 1983; 158:265-70.
McDevitt C A, Webber R J. The ultrastructure and biochemistry of meniscal cartilage. Clin Orthop 1990; 252:8-18.
Cheung H S. Distribution of type I, II, III and V in the pepsin solubilized collagens in bovine menisci. Connect Tissue Res 1987; 16:343-56.
Verdonk R, Kohn D. Harvest and conservation of meniscal allografts. Scand J Med Sci Sports 1999; 9:158-9
Buma P, Ramrattan N N, van Tienen T G, Veth R P H. Tissue engineering of the meniscus. Biomaterials 2004; 25:1523-32.
Kohn D, Verdonk R, Aagaard H, Seil R, Dienst M. Meniscal substitutes-animal experience. Scand J Med Sci Sports 1999; 9:141-5.
Ghadially F, Lalonde J, Wedge J. Ultrastructure of normal and torn menisci of the human knee joint. J Anat 1983; 136: 773-91.
Peretti G M, Gill T J, Xu J W, Randolph M A, Morse K R, Zaleske D J. Cell-based therapy for meniscal repair: a large animal study. Am J Sports Med 2004; 32: 146-158.
Izuta Y, Ochi M, Adachi N, Deie M, Yamasaki T, Shinomiya R. Meniscal repair using bone marrow derived mesenchymal stem cells: experimental study using green fluorescent protein transgenic rats. Knee 2005; 12:217-223
Port J, Jackson D W, Lee T Q, Simon T M. Meniscal repair supplemented with exogenous fibrin clot and autogenous cultured marrow cells in the goat model. Am J Sports Med 1996; 24:547-555.

Stone, K R.; Rodkey, W G.; Webber, R J.; McKinney, L A.; Steadman, J R. Development of a prosthetic meniscal replacement. In: Mow, V C.; Arnoczky, S P.; Jackson, D W., editors. Knee meniscus: basic and clinical foundations. Raven Press, Ltd.; New York: 1992. p. 165-173.

Cook J L, Fox D B, Malaviya P, Tomlinson J L, Kuroki K, Cook C R, Kladakis S. Longterm Outcome for Large Meniscal Defects Treated With Small Intestinal Submucosa in a Dog Model. Am J Sports Med 2006; 34:32-42. (a)

Brendon M. Baker and Robert L. Mauck. The Effect of Nanofiber Alignment on the Maturation of Engineered Meniscus Constructs. Biomaterials. 2007 April; 28(11): 1967-1977.

Setton L A, Guilak F, Hsu E W, Vail T P. Biomechanical factors in tissue engineered meniscal repair. Clin Orthop 1999; 5254-72.

Sweigart M A, Athanasiou K A. Toward tissue engineering of the knee meniscus. Tissue Eng 2001; 7:111-29.

Kobayashi M, Chang Y S, Oka M. A two year in vivo study of polyvinyl alcohol-dihydrogel (PVA-H) artificial meniscus. Biomaterials 2005; 26: 3243-8.

Kelly B T, Robertson W, Potter H G, Deng X H, Turner A S, Lyman S, et al. Hydrogel meniscal replacement in the sheep knee e preliminary evaluation of chondroprotective effects. Am J Sports Med 2007; 35:43-52 van Tienen T G, Heijkants R G, Buma P, de Groot J H, Pennings A J, Veth R P. Tissue ingrowth and degradation of two biodegradable porous polymers with different porosities and pore sizes. Biomaterials 2002; 23:1731-8.

Heijkants R G, van Calck R V, De Groot J H, Pennings A J, Schouten A J, van Tienen T G, et al. Design, synthesis and properties of a degradable polyurethane scaffold for meniscus regeneration. J Mater Sci Mater Med 2004; 15:423-7.

Cook J L, Fox D B, Malaviya P, Tomlinson J L, Farr J, Kuroki K, et al. Evaluation of small intestinal submucosa grafts for meniscal regeneration in a clinically relevant posterior meniscectomy model in dogs. J Knee Surg 2006; 19:159-67. (b)

B. M. Baker, A. S, Nathan, G. Russell Huffman, and R. L. Mauck. Tissue engineering with meniscus cells derived from surgical debris. Osteoarthritis and Cartilage (2009) 17, 336-345.

Tissakht, M., and Ahmed, A. M. Tensile stress-strain characteristics of the human meniscal material. J. Biomech. 28, 411, 1995.

P. C. M. Verdonk, R. G. Forsyth, J. Wang, K. F. Almqvist, R. Verdonk, E. M. Veys and G. Verbruggen. Characterisation of human knee meniscus cell phenotype. OsteoArthritis and Cartilage (2005) 13, 548-560

Whitley, C. B., Ridnour, M. D., Draper, K. A., Dutton, C. M., and Neglia, J. P. Diagnostic test for mucopolysaccharidosis. I. Direct method for quantifying excessive urinary glycosaminoglycan excretion. Clin Chem. 35, 374, 1989.

Tullberg-Reinert, H., and Jundt, G. In situ measurement of collagen synthesis by human bone cells with a sirius red-based colorimetric microassay: effects of transforming growth factor beta2 and ascorbic acid 2-phosphate. Histochem. Cell Biol. 112, 271, 1999.

Grande D A, Halberstadt C, Naughton G, Schwartz R, Manji R. Evaluation of matrix scaffolds for tissue engineering of articular cartilage grafts. J Biomed Mater Res 1997; 34:211-20.

Freed L E, Marquis J C, Nohria A, Emmanual J, Mikos A G, Langer R. Neocartilage formation in vitro and in vivo using cells cultured on synthetic biodegradable polymers. J Biomed Mater Res 1993; 27:11-23. a Freed L E, Vunjak-Novakovic G, Langer R. Cultivation of cellpolymer cartilage implants in bioreactors. J Cell Biochem 1993; 5 1:257-64. b Paige K T, Cima L G, Yaremchuk M J, Schloo B L, Vacanti J P, Vacanti C A. De novo cartilage generation using calcium alginatechondrocyte constructs. Plast Reconstr Surg 1996; 97:168-78 discussion 179-80.

Marijnissen W J, van Osch G J, Aigner J, van der Veen S W, Hollander A P, Verwoerd-Verhoef H L, Verhaar J A. Alginate as a chondrocyte-delivery substance in combination with a non-woven scaffold for cartilage tissue engineering. Biomaterials 2002; 23:1511-7.

Ma H L, Hung S C, Lin S Y, Chen Y L, Lo W H. Chondrogenesis of human mesenchymal stem cells encapsulated in alginate beads. J Biomed Mater Res 2003; 64A:273-81.

Cancedda R, Dozin B, Giannoni P, Quarto R. Tissue engineering and cell therapy of cartilage and bone. Matrix Biol 2003; 22: 81-91.

Athanasiou K A, Niederauer G G, Agrawal C M. Sterilization, toxicity, biocompatibility and clinical applications of polylactic acid/polyglycolic acid copolymers. Biomaterials 1996; 17:93-102.

Wakitani S, Goto T, Pineda S J, Young R G, Mansour J M, Caplan A I, Goldberg V M. Mesenchymal cell-based repair of large, fullthickness defects of articular cartilage. J Bone Surg Am 1994; 76:579-92.

Meinel L, Hofmann S, Karageorgiou V, Zichner L, Langer R, Kaplan D, Vunjak-iNovakovic G. Engineering cartilage-like tissue using human mesenchymal stem cells and silk protein scaffolds. Biotechnol Bioeng 2004; 88:379-91. a Meinel L, Karageorgiou V, Hofmann S, Fajardo R, Snyder B, Li C, Zichner L, Langer R, Vunjak-Novakovic G, Kaplan D L. Engineering bone-like tissue in vitro using human bone marrow stem cells and silk scaffolds. J Biomed Mater Res 2004; 71A:25-34. b Mauck R L, Martinez-Diaz G J, Yuan X, Tuan R S. Regional variation in meniscal fibrochondrocyte multi-lineage differentiation potential: implications for meniscal repair. Anat Rec 2007; 290:48-58.

Adams M E, Hukins D W L. The extracellular matrix of the meniscus. In: Mow V C, Arnoczky S P, Jackson D W, Eds. Knee Meniscus: Basic and Clinical Foundations. New York: Raven Press, Ltd.; 1992:15-28

Chia and Hull. Compressive moduli of the human medial meniscus in the axial and radial directions at equilibrium and at a physiological strain rate. J Orthop Res. 2008 July; 26(7):95 1-6.

Sweigart et al., Intraspecies and Interspecies Comparison of the Compressive Properties of the Medial Meniscus. Annals of Biomedical Engineering, 32, 2004:1569-1579

Gunja et al., Effects of co-culture of meniscal cells and articular chondrocytes on PLLA scaffolds. Biotec Bioeng 103, 2009:800-816

Coutts R D, Healey R M, Ostrander R, Sah R L, Goomer R, Amiel D. Matrices for cartilage repair. Clin Orthop Relat Res 2001; 391(Suppl): S271-79.

Temenoff J S, Mikos A G, Review: tissue engineering for regeneration of articular cartilage. Biomaterials 2000; 21: 43 1-40.

Altman G H, Diaz F, Jakuba C, Calabro T, Horan R L, Chen J, Lu H, Richmond J, Kaplan D L. Silk-based biomaterials. Biomaterials 2003; 24:40 1-16.

Altman G H, Horan R L, Lu H H, Moreau J, Martin I, Richmond J C, Kaplan D L. Silk matrix for tissue engineered anterior cruciate ligaments. Biomaterials 2002; 23:413 1-41.

Zhang X, Reagan M R, Kaplan D L. Electrospun silk biomaterial scaffolds for regenerative medicine. Adv Drug Deliv Rev. 2009 Oct. 5; 61(12):988-1006.

Wang Y, Kim H J, Vunjak-Novakovic G, Kaplan D L. Stem cell-based tissue engineering with silk biomaterials. Biomaterials. 2006 December; 27(36):6064-82. a Meinel L, Hofmann S, Karageorgiou V, Zichner L, Langer R, Kaplan D, Vunjak-iNovakovic G. Engineering cartilage-like tissue using human mesenchymal stem cells and silk protein scaffolds. Biotechnol Bioeng 2004; 88:379-91. a Meinel L, Karageorgiou V, Hofmann S, Fajardo R, Snyder B, Li C, Zichner L, Langer R, Vunjak-Novakovic G, Kaplan D L. Engineering bone-like tissue in vitro using human bone marrow stem cells and silk scaffolds. J Biomed Mater Res 2004; 71A:25-34. b Wang Y, Kim U J, Blasioli D J, Kim H J, Kaplan D L. In vitro cartilage tissue engineering with 3D porous aqueous-derived silk scaffolds and mesenchymal stem cells. Biomaterials 26 (2005) 7082-7094.

Wang Y, Blasioli D J, Kim H J, Kim H S, Kaplan D L. Cartilage tissue engineering with silk scaffolds and human articular chondrocytes. Biomaterials. 2006 September; 27(25):4434-42. b Hofmann S, Knecht S, Langer R, Kaplan D L, Vunjak-Novakovic G, Merkle H P, Meinel L. Cartilage-like tissue engineering using silk scaffolds and mesenchymal stem cells. Tissue Eng. 2006 October; 12(10):2729-38.

Peter Angele, Brian Johnstone, Richard Kujat, Johannes Zellner, Michael Nerlich, Victor Goldberg, Jung Yoo. Stem cell based tissue engineering for meniscus repair. Journal of Biomedical Materials Research Part A; 2007: 85A: 445-455

Wang Y, Rudym D D, Walsh A, Abrahamsen L, Kim H J, Kim H S, Kirker-Head C, Kaplan D L. In vivo degradation of three-dimensional silk fibroin scaffolds. Biomaterials. 2008 August-September; 29(24-25):3415-28

Horan R L, Antle K, Collette A L, Wang Y, Huang J, Moreau J E, Volloch V, Kaplan D L, Altman G H. In vitro degradation of silk fibroin. Biomaterials. 2005 June; 26(17):3385-93

Numata K, Cebe P, Kaplan D L. Mechanism of enzymatic degradation of beta-sheet crystals. Biomaterials. 2010 April; 3 1(10):2926-33.

Sun-Woong Kang, Sun-Mi Son, Jae-Sun Lee, Eung-Seok Lee, Kwon-Yong Lee, Sang¬ Guk Park, Jung-Ho Park, Byung-Soo Kim. Regeneration of whole meniscus using meniscal cells and polymer scaffolds in a rabbit total meniscectomy model. J Biomed Mater Res 77A: 659-67 1, 2006

Kim, U. J., Park, J., Kim, H. J., Wada, M., and Kaplan, D. L. Three-dimensional aqueous-derived biomaterial scaffolds from silk fibroin. Biomaterials 26, 2775, 2005.

REFERENCES

For Examples 6-9

M. Englund, E. M. Roos, L. S. Lohmander, Impact of type of meniscal tear on radiographic and symptomatic knee osteoarthritis: a sixteen-year follow up of meniscectomy with matched controls, Arthritis Rheum. 48 (2003) 2178-2187.

T. J. Fairbank, Knee joint changes after meniscectomy, J. Bone Joint Surg. Br. 30B (1948) 664-670.

Wolf Petersen and Bernhard Tillmann. Collagenous fibril texture of the human knee joint menisci. Anat Embryol (1998) 197:317-324

Proctor C S, Schmidt M B, Whipple R R, Kelly M A, Mow V C. Material properties of the normal medial bovine meniscus. J Orthop Res 1989; 7:771-82.

Herwig J, Egner E, Buddecke E. Chemical changes of human knee joint menisci in various stages of degeneration. Ann Rheum Dis 1984; 43:635-40

Eyre D R, Wu J J. Collagen of fibrocartilage: a distinctive molecular phenotype in bovine meniscus. FEBS Lett 1983; 158:265-70.

McDevitt C A, Webber R J. The ultrastructure and biochemistry of meniscal cartilage. Clin Orthop 1990; 252:8-18.

Verdonk R, Kohn D. Harvest and conservation of meniscal allografts. Scand J Med Sci Sports 1999; 9:158-9

Buma P, Ramrattan N N, van Tienen T G, Veth R P H. Tissue engineering of the meniscus. Biomaterials 2004; 25:1523-32.

Kohn D, Verdonk R, Aagaard H, Seil R, Dienst M. Meniscal substitutes-animal experience. Scand J Med Sci Sports 1999; 9:141-5.

Peretti G M, Gill T J, Xu J W, Randolph M A, Morse K R, Zaleske D J. Cell-based therapy for meniscal repair: a large animal study. Am J Sports Med 2004; 32: 146-158.

Izuta Y, Ochi M, Adachi N, Deie M, Yamasaki T, Shinomiya R. Meniscal repair using bone marrow derived mesenchymal stem cells: experimental study using green fluorescent protein transgenic rats. Knee 2005; 12:217-223

Port J, Jackson D W, Lee T Q, Simon T M. Meniscal repair supplemented with exogenous fibrin clot and autogenous cultured marrow cells in the goat model. Am J Sports Med 1996; 24:547-555.

Stone, K R.; Rodkey, W G.; Webber, R J.; McKinney, L A.; Steadman, J R. Development of a prosthetic meniscal replacement. In: Mow, V C.; Arnoczky, S P.; Jackson, D W., editors.

Knee meniscus: basic and clinical foundations. Raven Press, Ltd.; New York: 1992. p. 165-173.

Cook J L, Fox D B, Malaviya P, Tomlinson J L, Kuroki K, Cook C R, Kladakis S. Long-term Outcome for Large Meniscal Defects Treated With Small Intestinal Submucosa in a Dog Model. Am J Sports Med 2006; 34:32-42. (a)

Brendon M. Baker and Robert L. Mauck. The Effect of Nanofiber Alignment on the Maturation of Engineered Meniscus Constructs. Biomaterials. 2007 April; 28(11): 1967-1977.

Setton L A, Guilak F, Hsu E W, Vail T P. Biomechanical factors in tissue engineered meniscal repair. Clin Orthop 1999; 5254-72.

Sweigart M A, Athanasiou K A. Toward tissue engineering of the knee meniscus. Tissue Eng 2001; 7:111-29.

Kobayashi M, Chang Y S, Oka M. A two year in vivo study of polyvinyl alcohol-hydrogel (PVA-H) artificial meniscus. Biomaterials 2005; 26: 3243-8.

Kelly B T, Robertson W, Potter H G, Deng X H, Turner A S, Lyman S, et al. Hydrogel meniscal replacement in the sheep knee e preliminary evaluation of chondroprotective effects. Am J Sports Med 2007; 35:43-52 van Tienen T G, Heijkants R G, Buma P, de Groot J H, Pennings A J, Veth R P. Tissue ingrowth and degradation of two biodegradable porous polymers with different porosities and pore sizes. Biomaterials 2002; 23:1731-8.

Heijkants R G, van Calck R V, De Groot J H, Pennings A J, Schouten A J, van Tienen T G, et al. Design, synthesis and properties of a degradable polyurethane scaffold for meniscus regeneration. J Mater Sci Mater Med 2004; 15:423-7.

Cook J L, Fox D B, Malaviya P, Tomlinson J L, Farr J, Kuroki K, et al. Evaluation of small intestinal submucosa grafts for meniscal regeneration in a clinically relevant posterior meniscectomy model in dogs. J Knee Surg 2006; 19:159-67. (b)

B. M. Baker, A. S, Nathan, G. Russell Huffman, and R. L. Mauck. Tissue engineering with meniscus cells derived from surgical debris. Osteoarthritis and Cartilage (2009) 17, 336-345.

Tissakht, M., and Ahmed, A. M. Tensile stress-strain characteristics of the human meniscal material. J. Biomech. 28, 411, 1995.

P. C. M. Verdonk, R. G. Forsyth, J. Wang, K. F. Almqvist, R. Verdonk, E. M. Veys and G. Verbruggen. Characterisation of human knee meniscus cell phenotype. OsteoArthritis and Cartilage (2005) 13, 548-560

Whitley, C. B., Ridnour, M. D., Draper, K. A., Dutton, C. M., and Neglia, J. P. Diagnostic test for mucopolysaccharidosis. I. Direct method for quantifying excessive urinary glycosaminoglycan excretion. Clin Chem. 35, 374, 1989.

Tullberg-Reinert, H., and Jundt, G. In situ measurement of collagen synthesis by human bone cells with a sirius red-based colorimetric microassay: effects of transforming growth factor beta2 and ascorbic acid 2-phosphate. Histochem. Cell Biol. 112, 271, 1999.

Adams M E, Hukins D W L. The extracellular matrix of the meniscus. In: Mow V C, Arnoczky S P, Jackson D W, Eds. Knee Meniscus: Basic and Clinical Foundations. New York: Raven Press, Ltd.; 1992:15-28

Altman G H, Diaz F, Jakuba C, Calabro T, Horan R L, Chen J, Lu H, Richmond J, Kaplan D L. Silk-based biomaterials. Biomaterials 2003; 24:40 1-16.

Altman G H, Horan R L, Lu H H, Moreau J, Martin I, Richmond J C, Kaplan D L. Silk matrix for tissue engineered anterior cruciate ligaments. Biomaterials 2002; 23:413 1-41.

Zhang X, Reagan M R, Kaplan D L. Electrospun silk biomaterial scaffolds for regenerative medicine. Adv Drug Deliv Rev. 2009 Oct. 5; 61(12):988-1006.

Wang Y, Kim H J, Vunjak-Novakovic G, Kaplan D L. Stem cell-based tissue engineering with silk biomaterials. Biomaterials. 2006 December; 27(36):6064-82. a Meinel L, Hofmann S, Karageorgiou V, Zichner L, Langer R, Kaplan D, Vunjak-Novakovic G. Engineering cartilage-like tissue using human mesenchymal stem cells and silk protein scaffolds. Biotechnol Bioeng 2004; 88:379-91. a Meinel L, Karageorgiou V, Hofmann S, Fajardo R, Snyder B, Li C, Zichner L, Langer R, Vunjak-Novakovic G, Kaplan D L. Engineering bone-like tissue in vitro using human bone marrow stem cells and silk scaffolds. J Biomed Mater Res 2004; 71A:25-34. b Wang Y, Kim U J, Blasioli D J, Kim H J, Kaplan D L. In vitro cartilage tissue engineering with 3D porous aqueous-derived silk scaffolds and mesenchymal stem cells. Biomaterials 26 (2005) 7082-7094.

Wang Y, Blasioli D J, Kim H J, Kim H S, Kaplan D L. Cartilage tissue engineering with silk scaffolds and human articular chondrocytes. Biomaterials. 2006 September; 27(25):4434-42. b Hofmann S, Knecht S, Langer R, Kaplan D L, Vunjak-Novakovic G, Merkle H P, Meinel L. Cartilage-like tissue engineering using silk scaffolds and mesenchymal stem cells. Tissue Eng. 2006 October; 12(10):2729-38.

Wang Y, Rudym D D, Walsh A, Abrahamsen L, Kim H J, Kim H S, Kirker-Head C, Kaplan D L. In vivo degradation of three-dimensional silk fibroin scaffolds. Biomaterials. 2008 August-September; 29(24-25):3415-28

Horan R L, Antle K, Collette A L, Wang Y, Huang J, Moreau J E, Volloch V, Kaplan D L, Altman G H. In vitro degradation of silk fibroin. Biomaterials. 2005 June; 26(17):3385-93

Numata K, Cebe P, Kaplan D L. Mechanism of enzymatic degradation of beta-sheet crystals. Biomaterials. 2010 April; 3 1(10):2926-33.

Kim, U. J., Park, J., Kim, H. J., Wada, M., and Kaplan, D. L. Three-dimensional aqueous-derived biomaterial scaffolds from silk fibroin. Biomaterials 26, 2775, 2005.

Krause, W. R., Pope, M. H., Johnson, R. J., and Wilder, D. G. Mechanical changes in the knee after meniscectomy. J. Bone Joint Surg Am. 58, 599, 1976

Cox, J. S., Nye, C. E., Schaefer, W. W., and Woodstein, I. J. The degenerative effects of partial and total resection of the medial meniscus in dogs' knees. Clin. Orthop. 109, 178, 1975.

Radin E L, de Lamotte F, Maquet P. Role of the menisci in the distribution of stress in the knee. Clin Orthop 1984; 185: 290-294.

Boyd, K. T., and Myers, P. T. Meniscus preservation: Rationale, repair techniques and results. Knee 10, 1, 2003

Muraglia A, Cancedda R, Quarto R. Clonal mesenchymal progenitors from human bone marrow differentiate in vitro according to a hierarchical model. J Cell Science 2000; 113:1161-6.

Pittenger M F, Mackay A M, Beck S C, Jaiswal R K, Douglas R, Mosca J D, Moorman M A, Simonetti D W, Craig S, Marshak D R. Multilineage potential of adult human mesenchymal stem cells. Science 1999; 284:143-7.

Ghosh P, Taylor T K. The knee joint meniscus. A fibrocartilage of some distinction. Clin Orthop Relat Res 1987; (224):52-63.

Setton L A, Guilak F, Hsu E W, et al. Biomechanical factors in tissue engineered meniscal repair. Clin Orthop Relat Res 1999; (367 Suppl):254-72.

Koga H, Muneta T, Ju Y J, Nagase T, Nimura A, Mochizuki T, et al. Synovial stem cells are regionally specified according to local microenvironments after implantation for cartilage regeneration. Stem Cells 2007; 25:689-96.

Nehrer S, Spector M, Minas T. Histologic analysis of tissue after failed cartilage repair procedures. Clin Orthop Relat Res 1999; 365:149-62.

Sellers R S, Peluso D, Morris E A. The effect of recombinant human bone morphogenetic protein-2 (rhBMP-2) on the healing of full-thickness defects of articular cartilage. J Bone Joint Surg Am 1997; 79: 1452-63

Chimal-Monroy, J., Rodriguez-Leon, J., Montero, J. A., Ganan, Y., Macias, D., Merino, R., and Hurle, J. M. Analysis of the molecular cascade responsible for mesodermal limb chondrogenesis: Sox genes and BMP signaling. Dev. Biol. 257, 292, 2003.

Sekiya, I., Tsuji, K., Koopman, P., Watanabe, H., Yamada, Y., Shinomiya, K., Nifuji, A., and Noda, M. SOX9 enhances aggrecan gene promoter/enhancer activity and is up-regulated by retinoic acid in a cartilage-derived cell line, TC6. J. Biol. Chem. 275, 10738, 2000.

What is claimed is:

1. A biocompatible implant comprising: a silk fibroin scaffold having at least a first layer and a second layer, wherein the first layer is characterized as having a pore size distribution between about 100 and about 1,000 microns in diameter and comprises two sub-layers, wherein a first sub-layer has a larger pore size distribution than a second sub-layer, and the second layer comprises laminar channels.

2. The biocompatible implant of claim 1, wherein the silk fibroin scaffold further comprises at least one mammalian cell.

3. The biocompatible implant of claim 2, wherein the mammalian cells are human cells.

4. The biocompatible implant of claim 2, wherein the mammalian cells are selected from the group consisting of fibroblasts, chondrocytes, stem cells, bone marrow cells, embryonic stem cells, mesenchymal stem cells, induced pluripotent stem cells, differentiated stem cells, tissue-derived cells, and any combinations thereof.

5. The biocompatible implant of claims 2-4, wherein periphery of the silk fibroin scaffold comprises at least one fibroblast.

6. The biocompatible implant of claim 2, wherein an inner region of the silk fibroin scaffold comprises at least one chondrocyte.

7. The biocompatible implant of claim 2, wherein the silk fibroin scaffold comprise at least one stem cell.

8. The biocompatible implant of claim 1, wherein the first layer comprises approximately circular pores.

9. The biocompatible implant of claim 8, wherein the approximately circular pores are at least partially interconnected.

10. The biocompatible implant of claim 1, wherein the pore size distribution of the first layer ranges from about 200 microns to about 700 microns, or a portion thereof.

11. The biocompatible implant of claim 10, wherein the pore size distribution of the first layer ranges from about 300 microns to about 600 microns, or a portion thereof.

12. The biocompatible implant of claim 1, wherein the first sub-layer is closer to the second layer than the second sub-layer.

13. The biocompatible implant of claim 1, wherein the larger pore size distribution ranges from about 500 microns to about 700 microns.

14. The biocompatible implant of claim 1, wherein the silk fibroin scaffold further comprises a third layer.

15. The biocompatible implant of claim 14, wherein the third layer comprises pores with a pore size distribution ranging from about 10 microns to about 1,000 microns.

16. The biocompatible implant of claim 1, wherein the laminar channels are at least partially aligned.

17. The biocompatible implant of claim 1, wherein the laminar channels have a pore width distribution ranging between about 30 microns and about 100 microns, or a portion thereof.

18. The biocompatible implant of claim 17, wherein the laminar channels have a pore width distribution ranging between about 60 microns and about 80 microns, or a portion thereof.

19. The biocompatible implant of claim 1, wherein the porosity of each layer is independently at least about 30%.

20. The biocompatible implant of claim 1, wherein said each layer is individually formed before stacking together into a single composite unit.

21. The biocompatible implant of claim 1, further comprising at least one extracellular matrix.

22. The biocompatible implant of claim 1, further comprising at least one active agent, wherein the at least one active agent is selected from the group consisting of TGF-$\beta$1, TGF-$\beta$2, TGF-$\beta$3, BMP-2, BMP-4, BMP-6, BMP-12, BMP-13, basic fibroblast growth factor, fibroblast growth factor-1, fibroblast growth factor-2, platelet-derived growth factor-AA, platelet-derived growth factor-BB, platelet rich plasma, IGF-I, IGF-II, GDF-5, GDF-6, GDF-8, GDF-10, vascular endothelial cell-derived growth factor, pleiotrophin, endothelin, nicotinamide, glucagon like peptide-I, glucagon like peptide-II, parathyroid hormone, tenascin-C, tropoelastin, thrombin-derived peptides, laminin, biological peptides containing cell-binding domains and biological peptides containing heparin-binding domains, therapeutic agents, and any combinations thereof.

23. The biocompatible implant of claim 1, wherein the silk fibroin scaffold is adapted for meniscus repair or regeneration.

24. The biocompatible implant of claim 23, wherein each layer of the silk fibroin scaffold is crescent-shaped.

25. The biocompatible implant of claim 23, wherein the silk fibroin scaffold is wedge-shaped.

26. The biocompatible implant of claim 1, wherein the thickness of each layer is between about 0.1 mm and 5 mm.

* * * * *